US007419990B2

(12) United States Patent
Sings et al.

(10) Patent No.: US 7,419,990 B2
(45) Date of Patent: Sep. 2, 2008

(54) PIPERIDINE DERIVATIVES AS MELANOCORTIN-4 RECEPTOR AGONISTS

(75) Inventors: Heather Sings, West Windsor, NJ (US); Feroze Ujjainwalla, Scotch Plains, NJ (US)

(73) Assignee: Merck & Co., Inc., Rahway, NJ (US)

( * ) Notice: Subject to any disclaimer, the term of this patent is extended or adjusted under 35 U.S.C. 154(b) by 244 days.

(21) Appl. No.: 10/560,290

(22) PCT Filed: Jul. 16, 2004

(86) PCT No.: PCT/US2004/022911

§ 371 (c)(1),
(2), (4) Date: Dec. 12, 2005

(87) PCT Pub. No.: WO2005/009950

PCT Pub. Date: Feb. 3, 2005

(65) Prior Publication Data

US 2006/0128963 A1  Jun. 15, 2006

Related U.S. Application Data

(60) Provisional application No. 60/489,313, filed on Jul. 22, 2003.

(51) Int. Cl.
*A61K 31/445* (2006.01)
*C07D 401/06* (2006.01)
(52) U.S. Cl. .................. 514/326; 514/316; 514/317; 514/318; 540/597; 546/194; 546/207; 546/208
(58) Field of Classification Search .............. 514/326, 514/212, 316, 317, 318; 546/208, 194, 207; 540/597
See application file for complete search history.

(56) References Cited

U.S. PATENT DOCUMENTS 6,166,037 A    12/2000  Budhu et al.
6,818,658 B2 * 11/2004  Ujjainwalla et al. ......... 514/326

FOREIGN PATENT DOCUMENTS

WO   WO 02/067869   9/2002
WO   WO 02/068387   9/2002
WO   WO 02/068388   9/2002
WO   WO 03/009847   2/2003

OTHER PUBLICATIONS

Banno et al. "The melanocortin agonist . . . " Petides 25, p. 1279-1286 (2004).*
Obici et al. "Central melanocortin receptor . . . " J. Clin. Invest. 108, p. 1079-1085 (2001).*
Pierroz et al. "Effects of acute . . . " diabetes, 51, p. 1337-1345 (2002).*
Pochopin et al. "Amino acid derivatives . . . " Int. J. Pharm. 121, p. 157-167 (1995).*

Kopelman, Nature, vol. 404 (2000), pp. 635-643, "Obesity as a medical problem".
Huszar et al., Cell, vol. 88 (1997), pp. 131-141, "Targeted disruption of the melanocortin-4 receptor results in obesity in mice".
Kask et al., Biochem. & Biophys. Res. Comm., vol. 245 (1998), pp. 90-93, "Selected antagonist for the melanocortin 4 receptor (HSO014) increases food intake in free-feeding rats".
Chen et al., Cell, vol. 91 (1997), pp. 789-798, "Exocrine gland dysfunction in MC5-R-deficient mice . . . ".
Giraudo et al., Brain Res., vol. 809 (1998), pp. 302-306, "Feeding effects of hypothalamic injection of melanocortin 4 receptor ligands".
Hill et al. Science, vol. 280 (1998), pp. 1371-1374, "Environmental contributions to the obesity epidemic".
Corcos et al., Society for Neuroscience Abstracts, vol. 23 (1997), Abstract No. 267.9, p. 673, "HP 228 is a potent agonist of melanocortin receptor 4, and significantly attenuates obesity and diabetes in Zucker fatty rats".
Peptides: Frontiers of Peptide Science, Proceedings of the 15th American Peptide Symposium, Jun. 14-19, 1997, Nashville, TN.
Wessels et al., J. of Urology, vol. 160 (1998), pp. 389-393, "Synthetic melanotropic peptide initiates erections in men with psychogenic erectile dysfunction . . . ".
Dorr et al., Life Sciences, vol. 58, No. 20 (1996), pp. 1777-1784, "Evaluation of melanotan-II, a superpotent cyclic melanotropic peptide in a pilot phase-I clinical study".
Wessells et al., Urology, vol. 56 (2000), pp. 641-646, "Effect of an alpha-melanocyte stimulating hormone analog on penile erection and sexual desire in men with organic erectile dysfunction".
Graul, Drugs News & Perspectives, vol. 9 (1996), pp. 572-575, "Latest findings on the diagnosis and treatment of erectile dysfunction".
Dinsmore et al., Brit. Med. J., vol. 318 (1999), pp. 387-390, "ABC of sexual health—erectile dysfunction".
Gingell et al., Exp. Opin. Ther. Patents, vol. 9 (1999), pp. 1689-1696, "Emerging pharmacological therapies for erectile dysfunction".
Yoram et al., Current Opinion in Urology, vol. 7 (1997), pp. 349-353, "Oral pharmacotherapy in erectile dysfunction".
Heaton et al., Int'l J. of Impotence Res., vol. 9 (1997), pp. 115-121, "A therapeutic taxonomy of treatments for erectile dysfunction: an evolutionary imperative".
Budhu et al., Database Caplus on STN No. 130:223167 (1999), "Preparation of piperidinylpyrrolidins as modulators of chemokine receptor activity".
Goulet et al., Database Caplus on STN No. 137:216872 (2002), "Acylated piperidine derivatives, specifically 1-[(aminocycloalkyl)carbonyl]piperidines, as melanocortin-4 receptor agonists, and their pharmaceutical . . . ".

* cited by examiner

*Primary Examiner*—Celia Chang
(74) *Attorney, Agent, or Firm*—Richard C. Billups; Baerbel R. Brown; Catherine D. Fitch

(57) ABSTRACT

Certain novel piperidine derivatives are agonists of the human melanocortin receptor(s) and, in particular, are selective agonists of the human melanocortin-4 receptor (MC-4R). They are therefore useful for the treatment, control, or prevention of diseases and disorders responsive to the activation of MC-4R, such as obesity, diabetes, sexual dysfunction, including erectile dysfunction and female sexual dysfunction.

17 Claims, No Drawings

PIPERIDINE DERIVATIVES AS MELANOCORTIN-4 RECEPTOR AGONISTS

CROSS-REFERENCE TO RELATED APPLICATIONS

This application is a U.S. National Phase application under 35 U.S.C. §371 of PCT Application No. PCT/US2004/022911, filed Jul. 16, 2004, which claims priority under 35 U.S.C. §119 from U.S. Provisional Application No. 60/489,313, filed Jul. 22, 2003.

FIELD OF THE INVENTION

The present invention relates to piperidine derivatives, their synthesis, and their use as melanocortin receptor (MC-R) agonists. More particularly, the compounds of the present invention are selective agonists of the melanocortin-4 receptor (MC-4R) and are thereby useful for the treatment of disorders responsive to the activation of MC-4R, such as obesity, diabetes, male sexual dysfunction, and female sexual dysfunction.

BACKGROUND OF THE INVENTION

Obesity, which can be defined as a body weight more than 20% above the ideal body weight, is a major health concern in Western societies. It is estimated that about 97 million adults in the United States are overweight or obese. Obesity is the result of a positive energy balance, as a consequence of increased ratio of caloric intake to energy expenditure. Epidemiological studies have shown that increasing degrees of overweight and obesity are important predictors of decreased life expectancy. Obesity causes or exacerbates many health problems, both independently and in association with other diseases. The medical problems associated with obesity, which can be serious and life-threatening, include hypertension; type 2 diabetes mellitus; elevated plasma insulin concentrations; insulin resistance; dyslipidemias; hyperlipidemia; endometrial, breast, prostate and colon cancer; osteoarthritis; respiratory complications, such as obstructive sleep apnea; cholelithiasis; gallstones; arterioscelerosis; heart disease; abnormal heart rhythms; and heart arrythmias (Kopelman, P. G., Nature 404, 635-643 (2000)). Obesity is further associated with premature death and with a significant increase in mortality and morbidity from stroke, myocardial infarction, congestive heart failure, coronary heart disease, and sudden death.

In the vast majority of obese individuals, the cause of the excess adiposity is not immediately apparent. A currently accepted working hypothesis is that obesity is the result of a maladaptation of the innate metabolic response to environmental challenges such as unlimited availability of low cost/energy dense foods and sedentariness (Hill et al., Science 1998; 280:1371). The study of energy intake in free living humans has met with only limited success and definitive experimental evidence that hyperphagia causes most forms of human obesity is lacking. Following the discovery of leptin, the interest in the neurohormonal regulation of food intake has regained momentum. However, while much knowledge has been gained on the regulation of food intake in rodents and other animal species, the understanding of the neurophysiology of feeding behavior in humans remains extremely limited.

Pro-opiomelanocortin (POMC) derived peptides are known to affect food intake. Several lines of evidence support the notion that the G-protein coupled receptors (GPCRs) of the melanocortin receptor (MC-R) family, several of which are expressed in the brain, are the targets of POMC derived peptides involved in the control of food intake and metabolism. A specific single MC-R that may be targeted for the control of obesity has not yet been identified, although evidence has been presented that MC-4R signalling is important in mediating feed behavior (S. Q. Giraudo et al., "Feeding effects of hypothalamic injection of melanocortin4 receptor ligands," Brain Research, 80: 302-306 (1998)).

Evidence for the involvement of MC-R's in obesity includes: i) the agouti ($A^{vy}$) mouse which ectopically expresses an antagonist of the MC-1R, MC-3R and -4R is obese, indicating that blocking the action of these three MC-R's can lead to hyperphagia and metabolic disorders; ii) MC-4R knockout mice (D. Huszar et al., Cell, 88: 131-141 (1997)) recapitulate the phenotype of the agouti mouse and these mice are obese; iii) the cyclic heptapeptide MT-1 (a non-selective MC-1R, -3R, -4R, and -5R agonist) injected intracerebroventricularly (ICV) in rodents, reduces food intake in several animal feeding models (NPY, ob/ob, agouti, fasted) while ICV injected SHU-9119 (MC-3R and 4R antagonist; MC-1R and -5R agonist) reverses this effect and can induce hyperphagia; iv) chronic intraperitoneal treatment of Zucker fatty rats with an α-NDP-MSH derivative (HP228) has been reported to activate MC-1R, -3R, 4R, and -5R and to attenuate food intake and body weight gain over a 12-week period (I. Corcos et al., "228 is a potent agonist of melanocortin receptor 4 and significantly attenuates obesity and diabetes in Zucker fatty rats," Society for Neuroscience Abstracts, 23: 673 (1997)).

Five distinct MC-R's have thus far been identified, and these are expressed in different tissues. MC-1R was initially characterized by dominant gain of function mutations at the Extension locus, affecting coat color by controlling phaeomelanin to eumelanin conversion through control of tyrosinase. MC-1R is mainly expressed in melanocytes. MC-2R is expressed in the adrenal gland and represents the ACTH receptor. MC-3R is expressed in the brain, gut, and placenta and may be involved in the control of food intake and thermogenesis. MC-4R is uniquely expressed in the brain, and its inactivation was shown to cause obesity (A. Kask, et al., "Selective antagonist for the melanocortin 4 receptor (HS014) increases food intake in free-feeding rats," Biochem. Biophys. Res. Commun., 245: 90-93 (1998)). MC-5R is expressed in many tissues, including white fat, placenta and exocrine glands. A low level of expression is also observed in the brain. MC-5R knockout mice reveal reduced sebaceous gland lipid production (Chen et al., Cell, 91: 789-798 (1997)).

Weight loss drugs that are currently used to treat obesity have limited efficacy and significant side effects. Studies of the weight loss medications orlistat (Davidson, M. H. et al. (1999) JAMA 281:235-42), dexfenfluramine (Guy Grand, B. et al. (1989) Lancet 2:1142-5), sibutramine (Bray, G. A. et al. (1999) Obes. Res. &:189-98) and phentermine (Douglas, A. et al. (1983) Int. J. Obes. 7:591-5) have demonstrated a limited weight loss of about 5%-10% of body weight for drug compared to placebo. The side effects of these drugs and anti-obesity agents further limit their use. Dexfenfluramine was withdrawn from the market because of suspected heart valvulopathy; orlistat is limited by gastrointestinal side effects; the use of topiramate is limited by central nervous system effects; and the use of sibutramine is limited by its cardiovascular side effects which have led to reports of deaths and its withdrawal from the market in Italy.

There is a need for a weight loss treatment with enhanced efficacy and fewer undesirable side effects. The instant invention addresses this problem by providing melanocortin receptor (MC-R) agonists, and in particular selective agonists of the melanocortin-4 receptor (MC-4R), useful in the treatment and prevention of obesity and obesity-related disorders, including diabetes.

Melanocortin receptor involvement in male and female sexual dysfunction has also been reported.

Erectile dysfunction denotes the medical condition of inability to achieve penile erection sufficient for successful sexual intercourse. The term "impotence" is oftentimes employed to describe this prevalent condition. Approximately 140 million men worldwide, and, according to a National Institutes of Health study, about 30 million American men suffer from impotency or erectile dysfunction. It has been estimated that the latter number could rise to 47 million men by the year 2000. Erectile dysfunction can arise from either organic or psychogenic causes, with about 20% of such cases being purely psychogenic in origin. Erectile dysfunction increases from 40% at age 40, to 67% at age 75. In spite of the frequent occurrence of this condition, only a small number of patients have received treatment because existing treatment alternatives, such as injection therapies, penile prosthesis implantation, and vacuum pumps, have been uniformly disagreeable [for a discussion, see "ABC of sexual health—erectile dysfunction," *Brit. Med. J.* 318: 387-390 (1999)]. Only more recently have more viable treatment modalities become available, in particular orally active agents, such as sildenafil citrate, marketed by Pfizer under the brand name of Viagra®. (See "Emerging pharmacological therapies for erectile dysfunction," *Exp. Opin. Ther. Patents* 9: 1689-1696 (1999)). Sildenafil is a selective inhibitor of type V phosphodiesterase (PDE-V), a cyclic-GMP-specific phosphodiesterase isozyme [see R. B. Moreland et al., "Sildenafil: A Novel Inhibitor of Phosphodiesterase Type 5 in Human Corpus Cavernosum Smooth Muscle Cells," *Life Sci.*, 62: 309-318 (1998)]. Prior to the introduction of Viagra® on the market, less than 10% of patients suffering from erectile dysfunction received treatment. Sildenafil is also being evaluated in the clinic for the treatment of female sexual dysfunction.

The regulatory approval of Viagra® for the oral treatment of erectile dysfunction has invigorated efforts to discover even more effective methods to treat erectile dysfunction. Several additional selective PDE-V inhibitors are in clinical trials. UK-114542 is a sildenafil backup from Pfizer with supposedly improved properties. Tadalafil or IC-351 (ICOS Corp.) is claimed to have greater selectivity for PDE-V over PDE-VI than sildenafil. Other PDE-V inhibitors include vardenafil from Bayer, M-54033 and M-54018 from Mochida Pharmaceutical Co., and E-4010 from Eisai Co., Ltd.

Other pharmacological approaches to the treatment of erectile dysfunction have been described [see, e.g., "Latest Findings on the Diagnosis and Treatment of Erectile Dysfunction," *Drug News & Perspectives*, 9: 572-575 (1996); "Oral Pharmacotherapy in Erectile Dysfunction," *Current Opinion in Urology*, 7: 349-353 (1997)]. A product under clinical development by Zonagen is an oral formulation of the alpha-adrenoceptor antagonist phentolamine mesylate under the brand name of Vasomax®. Vasomax® is also being evaluated for the treatment of female sexual dysfunction.

Drugs to treat erectile dysfunction act either peripherally or centrally. They are also classified according to whether they "initiate" a sexual response or "facilitate" a sexual response to prior stimulation [for a discussion, see "A Therapeutic Taxonomy of Treatments for Erectile Dysfunction: An Evolutionary Imperative," *Int. J. Impotence Res.*, 9: 115-121 (1997)]. While sildenafil and phentolamine act peripherally and are considered to be "enhancers" or "facilitators" of the sexual response to erotic stimulation, sildenafil appears to be efficacious in both mild organic and psychogenic erectile dysfunction. Sildenafil has an onset of action of 30-60 minutes after an oral dose with the effect lasting about 4 hours, whereas phentolamine requires 5-30 minutes for onset with a duration of 2 hours. Although sildenafil is effective in a majority of patients, it takes a relatively long time for the compound to show the desired effects. The faster-acting phentolamine appears to be less effective and to have a shorter duration of action than sildenafil. Oral sildenafil is effective in about 70% of men who take it, whereas an adequate response with phentolamine is observed in only 35-40% of patients. Both compounds require erotic stimulation for efficacy. Since sildenafil indirectly increases blood flow in the systemic circulation by enhancing the smooth muscle relaxation effects of nitric oxide, it is contraindicated for patients with unstable heart conditions or cardiovascular disease, in particular patients taking nitrates, such as nitroglycerin, to treat angina. Other adverse effects associated with the clinical use of sildenafil include headache, flushing, dyspepsia, and "abnormal vision," the latter the result of inhibition of the type VI phosphodiesterase isozyme (PDE-VI), a cyclic-GMP-specific phosphodiesterase that is concentrated in the retina. "Abnormal vision" is defined as a mild and transient "bluish" tinge to vision, but also an increased sensitivity to light or blurred vision.

Synthetic melanocortin receptor agonists (melanotropic peptides) have been found to initiate erections in men with psychogenic erectile dysfunction [See H. Wessells et al., "Synthetic Melanotropic Peptide Initiates Erections in Men With Psychogenic Erectile Dysfunction: Double-Blind, Placebo Controlled Crossover Study," *J. Urol.*, 160: 389-393 (1998); *Fifteenth American Peptide Symposium*, Jun. 14-19, 1997 (Nashville Tenn.)]. Activation of melanocortin receptors of the brain appears to cause normal stimulation of sexual arousal. In the above study, the centrally acting α-melanocyte-stimulating hormone analog, melanotan-II (MT-II), exhibited a 75% response rate, similar to results obtained with apomorphine, when injected intramuscularly or subcutaneously to males with psychogenic erectile dysfunction. MT-II is a synthetic cyclic heptapeptide, Ac-Nle-c[Asp-His-DPhe-Arg-Trp-Lys]-NH$_2$, which contains the 4-10 melanocortin receptor binding region common to α-MSH and adrenocorticotropin, but with a lactam bridge. It is a non-selective MC-1R, -3R, -4R, and -5R agonist (Dorr et al., *Life Sciences*, Vol. 58, 1777-1784, 1996). MT-II (also referred to as PT-14) (Erectide®) is presently in clinical development by Palatin Technologies, Inc. and TheraTech, Inc. as a non-penile subcutaneous injection formulation. It is considered to be an "initiator" of the sexual response. The time to onset of erection with this drug is relatively short (10-20 minutes) with a duration of action approximately 2.5 hours. Adverse reactions observed with MT-II include nausea, flushing, loss of appetite, stretching, and yawning and may be the result of activation of MC-1R, MC-2R, MC-3R, and/or MC-5R. MT-II must be administered parenterally, such as by subcutaneous, intravenous, or intramuscular route, since it is not absorbed into the systemic circulation when given by the oral route.

MT-II's erectogenic properties apparently are not limited to cases of psychogenic erectile dysfunction in that men with a variety of organic risk factors developed penile erections upon subcutaneous injection of the compound; moreover, the level of sexual desire was significantly higher after MT-II administration than after placebo [see H. Wessells, "Effect of an Alpha-Melanocyte Stimulating Hormone Analog on Penile Erection and Sexual Desire in Men with Organic Erectile Dysfunction," Urology, 56: 641-646 (2000)].

Compositions of melanotropic peptides and methods for the treatment of psychogenic erectile dysfunction are disclosed in U.S. Pat. No. 5,576,290, assigned to Competitive Technologies. Methods of stimulating sexual response in females using melanotropic peptides have been disclosed in U.S. Pat. No. 6,051,555.

Spiropiperidine, piperidine and piperazine derivatives have been disclosed in WO 99/64002 (16 Dec. 1999); WO 00/74679 (14 Dec. 2000); WO 01/70708 (27 Sep. 2001); WO 01/70337 (27 Sep. 2001); WO 01/91752 (6 Dec. 2001); WO 02/059095 (1 Aug. 2002) WO 02/059107(1 Aug. 2002); WO 02/059108(1 Aug. 2002); WO 02/059117(1 Aug. 2002); WO 02/068387 (6 Sep. 2002); WO 02/068388 (6 Sep. 2002); WO 03/007949 (30 Jan. 2003 WO 03/009847 (6 Feb. 2003); and WO 03/31410, as agonists of the melanocortin receptor(s) and particularly as selective agonists of the MC-4R receptor and thereby useful for the treatment of diseases and disorders, such as obesity, diabetes, and sexual dysfunction, including erectile dysfunction and female sexual dysfunction.

Because of the unresolved deficiencies of the various pharmacological agents discussed above, there is a continuing need in the medical arts for improved methods and compositions to treat individuals suffering from psychogenic and/or organic sexual dysfunction. Such methods should have wider applicability, enhanced convenience and ease of compliance, short onset of action, reasonably long duration of action, and minimal side effects with few contraindications, as compared to agents now available.

It is therefore an object of the present invention to provide acylated piperidine derivatives which are melanocortin receptor agonists and thereby useful to treat obesity, diabetes, male sexual dysfunction, and female sexual dysfunction.

It is another object of the present invention to provide acylated piperidine derivatives which are selective agonists of the melanocortin-4 (MC-4R) receptor.

It is another object of the present invention to provide pharmaceutical compositions comprising the melanocortin receptor agonists of the present invention with a pharmaceutically acceptable carrier.

It is another object of the present invention to provide methods for the treatment or prevention of disorders, diseases, or conditions responsive to the activation of the melanocortin-4 receptor in a mammal in need thereof by administering the compounds and pharmaceutical compositions of the present invention.

It is another object of the present invention to provide methods for the treatment or prevention of obesity, diabetes mellitus, male sexual dysfunction, and female sexual dysfunction by administering the compounds and pharmaceutical compositions of the present invention to a mammal in need thereof.

It is another object of the present invention to provide methods for the treatment of erectile dysfunction by administering the compounds and pharmaceutical compositions of the present invention to a mammal in need thereof.

These and other objects will become readily apparent from the detailed description that follows.

SUMMARY OF THE INVENTION

The present invention relates to novel 4-phenyl substituted piperidines of structural formula I:

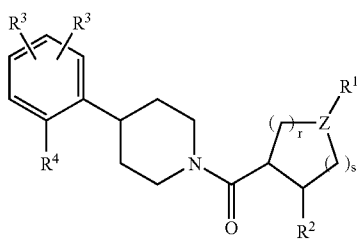

(I)

These piperidine derivatives are effective as melanocortin receptor agonists and are particularly effective as selective melanocortin-4 receptor (MC-4R) agonists. They are therefore useful for the treatment and/or prevention of disorders responsive to the activation of MC-4R, such as obesity, diabetes as well as male and female sexual dysfunction, in particular, male erectile dysfunction.

The present invention also relates to pharmaceutical compositions comprising the compounds of the present invention and a pharmaceutically acceptable carrier.

The present invention also relates to methods for the treatment or prevention of disorders, diseases, or conditions responsive to the activation of the melanocortin-4 receptor in a mammal in need thereof by administering the compounds and pharmaceutical compositions of the present invention.

The present invention also relates to methods for the treatment or prevention of obesity, diabetes mellitus, male sexual dysfunction, and female sexual dysfunction by administering the compounds and pharmaceutical compositions of the present invention.

The present invention also relates to methods for treating erectile dysfunction by administering the compounds and pharmaceutical compositions of the present invention.

The present invention also relates to methods for treating erectile dysfunction by administering the compounds of the present invention in combination with a therapeutically effective amount of another agent known to be useful to treat the condition.

The present invention also relates to methods for treating or preventing obesity by administering the compounds of the present invention in combination with a therapeutically effective amount of another agent known to be useful to prevent or treat the condition.

The present invention also relates to methods for treating or preventing diabetes by administering the compounds of the present invention in combination with a therapeutically effective amount of another agent known to be useful to prevent or treat the condition.

DETAILED DESCRIPTION OF THE INVENTION

The present invention relates to 4-substituted N-acylated piperidine derivatives useful as melanocortin receptor agonists, in particular, as selective MC-4R agonists. Compounds of the present invention are described by structural formula I:

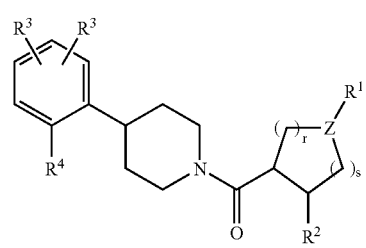

(I)

or a pharmaceutically acceptable salt thereof;

wherein $R^1$ is selected from the group consisting of:
(1) hydrogen,
(2) amidino,
(3) $C_{1-4}$ alkyliminoyl,
(4) $C_{1-10}$ alkyl,
(5) —$(CH_2)_n$—$NR^7R^8$,
(6) —$(CH_2)_n$—$C_{3-7}$ cycloalkyl,
(7) —$(CH_2)_n$-phenyl, (8) —(CH$_2$)$_n$-naphthyl, and
(9) —(CH$_2$)$_n$-heteroaryl, wherein phenyl, naphthyl, and heteroaryl are unsubstituted or substituted with one to three groups independently selected from R$^3$, and wherein alkyl and cycloalkyl are unsubstituted or substituted with one to three groups independently selected from R$^3$ and oxo;

R$^2$ is selected from the group consisting of:
(1) phenyl,
(2) naphthyl, and
(3) heteroaryl, wherein phenyl, naphthyl, and heteroaryl are unsubstituted or substituted with one to three groups independently selected from R$^3$;

each R$^3$ is independently selected from the group consisting of:
(1) hydrogen,
(2) C$_{1-6}$ alkyl,
(3) —(CH$_2$)$_n$-phenyl,
(4) —(CH$_2$)$_n$-naphthyl,
(5) —(CH$_2$)$_n$-heteroaryl,
(6) —(CH$_2$)$_n$-heterocycloalkyl,
(7) —(CH$_2$)$_n$C$_{3-7}$ cycloalkyl,
(8) halogen,
(9) OR$^6$,
(10) —(CH$_2$)$_n$N(R$^6$)$_2$,
(11) —(CH$_2$)$_n$C≡N,
(12) —(CH$_2$)$_n$CO$_2$R$^6$,
(13) NO$_2$,
(14) —(CH$_2$)$_n$NR$^6$SO$_2$R$^6$,
(15) —(CH$_2$)$_n$SO$_2$N(R$^6$)$_2$,
(16) —(CH$_2$)$_n$S(O)$_p$R$^6$,
(17) —(CH$_2$)$_n$NR$^6$C(O)N(R$^6$)$_2$,
(18) —(CH$_2$)$_n$C(O)N(R$^6$)$_2$,
(19) —(CH$_2$)$_n$NR$^6$C(O)R$^6$,
(20) —(CH$_2$)$_n$NR$^6$CO$_2$R$^6$,
(21) —(CH$_2$)$_n$NR$^6$C(O)-heteroaryl,
(22) —(CH$_2$)$_n$C(O)NR$^6$N(R$^6$)$_2$,
(23) —(CH$_2$)$_n$C(O)NR$^6$NR$^6$C(O)R$^6$,
(24) O(CH$_2$)$_n$C(O)N(R$^6$)$_2$,
(25) CF$_3$,
(26) CH$_2$CF$_3$,
(27) OCF$_3$, and
(28) OCH$_2$CF$_3$, wherein phenyl, naphthyl, heteroaryl, cycloalkyl, and heterocycloalkyl are unsubstituted or substituted with one to three substituents independently selected from halogen, hydroxy, oxo, C$_{1-4}$ alkyl, trifluoromethyl, and C$_{1-4}$ alkoxy, and wherein any methylene (CH$_2$) carbon atom in R$^3$ is unsubstituted or substituted with one to two groups independently selected from halogen, hydroxy, and C$_{1-4}$ alkyl, or wherein two substituents when on the same methylene (CH$_2$) group are taken together with the carbon atom to which they are attached to form a cyclopropyl group;

R$^4$ is selected from the group consisting of:
(1) —(CH$_2$)$_n$—N(R$^5$)—NR$^5$R$^6$,
(2) —(CH$_2$)$_n$—N(R$_5$)—(CH$_2$)$_q$—NR5R$^6$,
(3) —(CH$_2$)$_n$—N(R$^5$)—C(=NR$^5$)—NR$^5$R$^6$,
(4) —(CH$_2$)$_n$—N(R$^5$)—(CH$_2$)$_q$—N(R$^5$)—(C=NR$^5$)—NR$^5$R$^6$,
(5) —(CH$_2$)$_n$—N(R$^5$)—(CH$_2$)$_n$—C(R$^5$)(N(R$^5$)$_2$)—(CH$_2$)$_q$—OR$^6$,
(6) —(CH$_2$)$_n$—N(R$^5$)—(CH$_2$)$_n$—C(R$^5$)(N(R$^5$)$_2$)(CH$_2$)$_n$—R$^6$,
(7) —(CH$_2$)$_n$—N(R$^5$)—(CH$_2$)$_n$—C(R$^5$)(N(R$^5$)$_2$)(CH$_2$)$_q$—S(O)p—R$^6$,
(8) —(CH$_2$)$_n$—N(R$^5$)—(CH$_2$)$_n$—C(R$^5$)(N(R$^5$)$_2$)(CH$_2$)$_q$—NR$^5$R$^6$,
(9) —(CH$_2$)$_n$—N(R$^5$)—C(O)(CH$_2$)$_n$—C(R$^5$)(N(R$^5$)$_2$)(CH$_2$)$_n$—R$^6$,
(10) —(CH$_2$)$_n$—N(R$^5$)—C(O)(CH$_2$)$_n$—C(R$^5$)(N(R$^5$)$_2$)(CH$_2$)$_q$—S(O)p—R$^6$,
(11) —(CH$_2$)$_n$—N(R$^5$)—C(O)(CH$_2$)$_n$—C(R$^5$)(N(R$^5$)$_2$)(CH$_2$)$_q$—NR$^5$R$^6$,
(12) —(CH$_2$)$_n$—N(R$^5$)—C(O)(CH$_2$)$_n$—C(R$^5$)(N(R$^5$)$_2$)(CH$_2$)$_q$—O—R$^6$, and
(13) —(CH$_2$)$_n$—N(R$^5$)—R$^9$, wherein (CH$_2$)$_n$ is unsubstituted or substituted with one to three groups independently selected from halogen, C$_{1-4}$ alkyl, hydroxy, oxo, and C$_{1-4}$ alkoxy;

R$^5$ is selected from the group consisting of:
(1) hydrogen,
(2) C$_{1-6}$ alkyl, and
(3) C(O)C$_{1-6}$ alkyl, wherein alkyl is unsubstituted or substituted with one to three groups independently selected from halogen, C$_{1-4}$ alkyl, hydroxy, oxo, and C$_{1-4}$ alkoxy;

R$^6$ is selected from the group consisting of:
(1) hydrogen,
(2) C$_{1-6}$ alkyl,
(3) C(O)C$_{1-6}$ alkyl,
(4) —(CH$_2$)$_n$C$_{3-7}$ cycloalkyl,
(5) —(CH$_2$)$_n$C$_{2-7}$ heterocycloalkyl,
(6) —(CH$_2$)$_n$-phenyl,
(7) —(CH$_2$)$_n$-naphthyl,
(8) —(CH$_2$)$_n$-heteroaryl, and
(9) —(CH$_2$)$_n$C$_{3-7}$ bicycloalkyl, wherein alkyl, phenyl, heteroaryl, heterocycloalkyl, naphthyl, cycloalkyl, bicycloalkyl and (CH$_2$)$_n$ are unsubstituted or substituted with one to three groups independently selected from halogen, C$_{1-4}$ alkyl, hydroxy, and C$_{1-4}$ alkoxy, or wherein two R$^6$ groups together with the atom to which they are attached form a 4- to 8-membered mono- or bicyclic ring system optionally containing an additional heteroatom selected from O, S, and —NC$_{1-4}$ alkyl;

each R$^7$ and R$^8$ is independently selected from the group consisting of:
(1) hydrogen,
(2) amidino,
(3) C$_{1-4}$ alkyliminoyl,
(4) C$_{1-10}$ alkyl,
(5) —(CH$_2$)$_n$—C$_{3-7}$ cycloalkyl,
(6) —(CH$_2$)$_n$-phenyl,
(7) —(CH$_2$)$_n$-naphthyl, and
(8) —(CH$_2$)$_n$-heteroaryl, wherein phenyl, naphthyl, and heteroaryl are unsubstituted or substituted with one to three groups independently selected from R$^3$, and wherein alkyl and cycloalkyl are unsubstituted or substituted with one to three groups independently selected from R$^3$ and oxo;

R$^9$ is selected from the group consisting of:
(1) alanine,
(2) glycine,
(3) proline,
(4) cysteine,
(5) histidine,
(6) glutamine,
(7) aspartic acid,
(8) isoleucine,
(9) arginine,
(10) glutamic acid,

(11) lysine,
(12) serine,
(13) phenylalanine,
(14) leucine,
(15) threonine,
(16) tryptophan,
(17) methionine,
(18) valine,
(19) tyrosine,
(20) asparagine,
(21) 2-aminoadipic acid,
(22) beta-alanine,
(23) 2-aminoheptanedioic acid,
(24) 2-aminobutyric acid,
(25) 4-aminobutyric acid,
(26) 2,4-diaminobutyric acid,
(27) citrulline,
(28) cycloserine,
(29) norvaline,
(30) norleucine,
(31) ornithine,
(32) penicillamine,
(33) phenylglycine,
(34) phenylisoserine,
(35) phenylstatine,
(36) pipecolic acid,
(37) piperidine carboxylic acid,
(38) pyroglutamic acid,
(39) sarcosine,
(40) statine,
(41) allo-threonine,
(42) t-leucine,
(43) 2-aminoisobutyric acid, and
(44) 3-aminoisobutyric acid;

Z is selected from the group consisting of:
 (1) $C(R^1)$, and
 (2) N;
r is 1 or 2;
s is 0, 1, or 2;
n is 0, 1, 2, or 3;
p is 0, 1, or 2; and
q is 1, 2, 3, or 4.

In one embodiment of the compounds of structural formula I, $R^1$ is selected from the group consisting of: hydrogen, $C_{1-6}$ alkyl, —$(CH_2)_{0-1}C_{3-6}$ cycloalkyl, and —$(CH_2)_{0-1}$-phenyl, where phenyl is unsubstituted or substituted with one to three groups independently selected from $R^3$, and wherein alkyl and cycloalkyl are optionally substituted with one to three groups independently selected from $R^3$ and oxo. In a class of this embodiment, $R^1$ is selected from the group consisting of: hydrogen, and $C_{1-6}$ alkyl, and alkyl is optionally substituted with one to three groups independently selected from $R^3$ and oxo. In another class of this embodiment, $R^1$ is —$(CH_2)_{0-1}$—$NR^7R^8$.

In a second embodiment of the compounds of structural formula I, $R^2$ is phenyl or thienyl optionally substituted with one to three groups independently selected from $R^3$. In a class of this embodiment, $R^2$ is phenyl optionally substituted with one to three groups independently selected from $R^3$.

In a third embodiment of the compounds of structural formula I, $R^3$ is selected from the group consisting of: $C_{1-6}$ alkyl, —$(CH_2)_n$-phenyl, —$(CH_2)_n$-heteroaryl, —$(CH_2)_nC_{2-7}$ heterocycloalkyl, —$(CH_2)_nC_{3-7}$ cycloalkyl, halogen, $OR^5$, —$(CH_2)_nN(R^5)_2$, —$(CH_2)_nCO_2R^5$, $NO_2$, and $CF_3$, wherein phenyl, naphthyl, and heteroaryl are unsubstituted or substituted with one to three substituents independently selected from halogen, hydroxy, $C_{1-4}$ alkyl, trifluoromethyl, and $C_{1-4}$ alkoxy, and wherein alkyl, cycloalkyl, heterocycloalkyl, and $(CH_2)$ are unsubstituted or substituted with one to three substituents independently selected from halogen, hydroxy, oxo, $C_{1-4}$ alkyl, trifluoromethyl, and $C_{1-4}$ alkoxy, or wherein two substituents when on the same methylene ($CH_2$) group are taken together with the carbon atom to which they are attached to form a cyclopropyl group. In a class of this embodiment, $R^3$ is selected from the group consisting of: $C_{1-6}$ alkyl, halogen, and $OR^5$, wherein alkyl is unsubstituted or substituted with one to three substituents independently selected from halogen, hydroxy, oxo, $C_{1-4}$ alkyl, trifluoromethyl, and $C_{1-4}$ alkoxy.

In another embodiment of compounds of structural formula I, $R^4$ is selected from the group consisting of:
 (1) —$(CH_2)_n$—$N(R^5)$—$NH_2$,
 (2) —$(CH_2)_n$—$N(R^5)$—$(CH_2)_q$—$NH_2$,
 (3) —$(CH_2)_n$—$N(R^5)$—$(CH_2)_n$—$NR^5R^6$,
 (4) —$(CH_2)_n$—$N(R^5)$—$(CH_2)_n$—$NHC_{1-6}$ alkyl,
 (5) —$(CH_2)_n$—$N(R^5)$—$(CH_2)_n$—$N(C_{1-6}$ alkyl$)_2$,
 (6) —$(CH_2)_n$—$N(R^5)$—$(CH_2)_n$—$NHC(O)C_{1-6}$ alkyl,
 (7) —$(CH_2)_n$—$N(R^5)$—$(CH_2)_n$—$N(R^5)C(O)C_{1-6}$ alkyl,
 (8) —$(CH_2)_n$—$N(R^5)$—$(CH_2)_n$—$N(C(O)C_{1-6}$ alkyl$)_2$,
 (9) —$(CH_2)_n$—$N(R^5)$—$C(=NH)$—$NH_2$,
 (10) —$(CH_2)_n$—$N(R^5)$—$(CH_2)_q$—$NH(C=NH)$—$NH_2$,
 (11) —$(CH_2)_n$—$N(R^5)$—$(CH_2)_n$—$C(R^5)(NH_2)(CH_2)_q$—OH,
 (12) —$(CH_2)_n$—$N(R^5)$—$(CH_2)_n$—$C(R^5)(NH_2)(CH_2)_q$—)$C_{1-6}$ alkyl,
 (13) —$(CH_2)_n$—$N(R^5)$—$(CH_2)_n$—$C(R^5)(NH_2)(CH_2)_q$—$OR^6$,
 (14) —$(CH_2)_n$—$N(R^5)$—$(CH_2)_n$—$C(R^5)(NH_2)(CH_2)_n$-heteroaryl,
 (15) —$(CH_2)_n$—$N(R^5)$—$(CH_2)_n$—$C(R^5)(NH_2)(CH_2)_n$—$R^6$,
 (16) —$(CH_2)_n$—$N(R^5)$—$(CH_2)_n$—$C(R^5)(NH_2)(CH_2)_q$—SH,
 (17) —$(CH_2)_n$—$N(R^5)$—$(CH_2)_n$—$C(R^5)(NH_2)(CH_2)_q$—S—$C_{1-6}$ alkyl,
 (18) —$(CH_2)_n$—$N(R^5)$—$(CH_2)_n$—$C(R^5)(NH_2)(CH_2)_q$—S—$R^6$,
 (19) —$(CH_2)_n$—$N(R^5)$—$(CH_2)_n$—$C(R^5)(NH_2)(CH_2)_q$—$NH_2$,
 (20) —$(CH_2)_n$—$N(R^5)$—$(CH_2)_n$—$C(R^5)(NH_2)(CH_2)_q$—$NHR^6$,
 (21) —$(CH_2)_n$—$N(R^5)$—$(CH_2)_n$—$C(R^5)(NH_2)(CH_2)_q$—$NR^5R^6$,
 (22) —$(CH_2)_n$—$N(R^5)$—$C(O)(CH_2)_n$—$C(R^5)(NH_2)(CH_2)_n$-heteroaryl,
 (23) —$(CH_2)_n$—$N(R^5)$—$C(O)(CH_2)_n$—$C(R^5)(NH_2)(CH_2)_q$—SH,
 (24) —$(CH_2)_n$—$N(R^5)$—$C(O)(CH_2)_n$—$C(R^5)(NH_2)(CH_2)_q$—S—$C_{1-6}$ alkyl,
 (25) —$(CH_2)_n$—$N(R^5)$—$C(O)(CH_2)_n$—$C(R^5)(NH_2)(CH_2)_q$—$NR^5R^6$, and
 (26) —$(CH_2)_n$—$N(R^5)$—$R^9$, wherein alkyl and $(CH_2)_n$ are unsubstituted or substituted with one to three groups independently selected from halogen, $C_{1-4}$ alkyl, hydroxy, oxo, and $C_{1-4}$ alkoxy, and heteroaryl is unsubstituted or substituted with one to three groups independently selected from halogen, $C_{1-4}$ alkyl, hydroxy, and $C_{1-4}$ alkoxy.

In another embodiment of compounds of structural formula I, $R^4$ is selected from the group consisting of:
 (1) —$(CH_2)_n$—$N(R^5)$—$NH_2$,
 (2) —$(CH_2)_n$—$N(R^5)$—$(CH_2)_q$—$NH_2$,
 (3) —$(CH_2)_n$—$N(R^5)$—$(CH_2)_q$—$NHC_{1-6}$ alkyl, (4) —(CH$_2$)$_n$—N(R$^5$)—(CH$_2$)$_q$—N(C$_{1-6}$ alkyl)$_2$,
(5) —(CH$_2$)$_n$—N(R$^5$)—(CH$_2$)$_q$—NHC(O)C$_{1-6}$ alkyl,
(6) —(CH$_2$)$_n$—N(R$^5$)—C(=NH)—NH$_2$,
(7) —(CH$_2$)$_n$—N(R$^5$)—(CH$_2$)$_q$—NH(C=NH)—NH$_2$,
(8) —(CH$_2$)$_n$—N(R$^5$)—(CH$_2$)$_n$-C(R$^5$)(NH$_2$)(CH$_2$)$_q$—OH,
(9) —(CH$_2$)$_n$—N(R$^5$)—(CH$_2$)$_n$-C(R$^5$)(NH$_2$)(CH$_2$)$_q$—OC$_{1-6}$ alkyl,
(10) —(CH$_2$)$_n$—N(R$^5$)—C(O)(CH$_2$)$_n$—C(R$^5$)(NH$_2$)(CH$_2$)$_n$-heteroaryl,
(11) —(CH$_2$)$_n$—N(R$^5$)—C(O)(CH$_2$)$_n$—C(R$^5$)(NH$_2$)(CH$_2$)$_q$—S—C$_{1-6}$ alkyl,
(12) —(CH$_2$)$_n$—N(R$^5$)—C(O)(CH$_2$)$_n$—C(R$^5$)(NH$_2$)(CH$_2$)$_q$—NR$^5$R$^6$, and
(13) —(CH$_2$)$_n$—N(R$^5$)—R$^9$, wherein alkyl and (CH$_2$)$_n$ are unsubstituted or substituted with one to three groups independently selected from halogen, C$_{1-4}$ alkyl, hydroxy, oxo, and C$_{1-4}$ alkoxy, and heteroaryl is unsubstituted or substituted with one to three groups independently selected from halogen, C$_{1-4}$ alkyl, hydroxy, and C$_{1-4}$ alkoxy.

In one embodiment of the compounds of formula I, R$^6$ is selected from the group consisting of: hydrogen, C$_{1-6}$ alkyl, C(O)C$_{1-6}$ alkyl, and —(CH$_2$)$_n$-heteroaryl, wherein alkyl, heteroaryl, and (CH$_2$) are unsubstituted or substituted with one to three groups independently selected from halogen, C$_{1-4}$ alkyl, hydroxy, and C$_{1-4}$ alkoxy, or wherein two R$^6$ groups together with the atom to which they are attached form a 4- to 8-membered mono- or bicyclic ring system optionally containing an additional heteroatom selected from O, S, and —NC$_{1-4}$ alkyl.

In another embodiment of compounds of formula I, Z is N. In a class of this embodiment, Z is N and R$^1$ is selected from the group consisting of: hydrogen, amidino, C$_{1-4}$ alkyliminoyl, C$_{1-10}$ alkyl, —(CH$_2$)$_n$-C$_{3-7}$ cycloalkyl, —(CH$_2$)$_n$-phenyl, —(CH$_2$)$_n$-naphthyl, and —(CH$_2$)$_n$-heteroaryl. In a subclass of this class, Z is N and R$^1$ is C$_{1-10}$ alkyl.

In another embodiment of compounds of formula I, Z is CH. In a class of this embodiment, Z is CH and R$^1$ is —(CH$_2$)$_n$—NR$^7$R$^8$.

In yet a further embodiment of compounds of structural formula I, r is 1 or 2 and s is 1.

In yet a further embodiment of the compounds of the present invention, there are provided compounds of structural formula IIa or IIb of the indicated relative stereochemical configurations having the trans orientation of the phenyl and piperidinecarbonyl substituents:

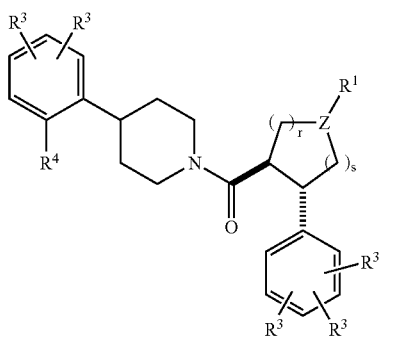

(IIa)

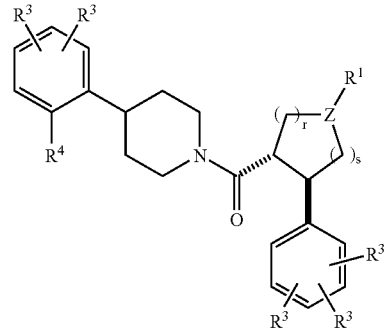

(IIb)

or a pharmaceutically acceptable salt thereof;

wherein
R$^1$ is selected from the group consisting of: hydrogen, amidino, C$_{1-4}$ alkyliminoyl, C$_{1-6}$ alkyl, C$_{5-6}$ cycloalkyl, —(CH$_2$)$_{0-1}$ phenyl, and —(CH$_2$)$_{0-1}$ heteroaryl, wherein phenyl and heteroaryl are unsubstituted or substituted with one to three groups independently selected from R$^3$, and wherein alkyl and cycloalkyl are unsubstituted or substituted with one to three groups independently selected from R$^3$ and oxo;

each R$^3$ is independently selected from the group consisting of:
(1) hydrogen,
(2) C$_{1-6}$ alkyl,
(3) —(CH$_2$)$_n$-phenyl,
(4) —(CH$_2$)$_n$-naphthyl,
(5) —(CH$_2$)$_n$-heteroaryl,
(6) —(CH$_2$)$_n$-heterocycloalkyl,
(7) —(CH$_2$)$_n$C$_{3-7}$ cycloalkyl,
(8) halogen,
(9) OR$^6$,
(10) —(CH$_2$)$_n$N(R$^6$)$_2$,
(11) —(CH$_2$)$_n$C≡N,
(12) —(CH$_2$)$_n$CO$_2$R$^6$,
(13) NO$_2$,
(14) —(CH$_2$)$_n$NR$^4$SO$_2$R$^6$,
(15) —(CH$_2$)$_n$SO$_2$N(R$^6$)$_2$,
(16) —(CH$_2$)$_n$S(O)$_{0-1}$R$^6$,
(17) —(CH$_2$)$_n$NR$^6$C(O)N(R$^6$)$_2$,
(18) —(CH$_2$)$_n$C(O)N(R$^6$)$_2$,
(19) —(CH$_2$)$_n$NR$^6$C(O)R$^6$,
(20) —(CH$_2$)$_n$NR$^6$CO$_2$R$^6$,
(21) —(CH$_2$)$_n$NR$^6$C(O)-heteroaryl,
(22) —(CH$_2$)$_n$C(O)NR$^6$N(R$^6$)$_2$,
(23) —(CH$_2$)$_n$C(O)NR$^6$NR$^6$C(O)R$^6$,
(24) O(CH$_2$)$_n$C(O)N(R6)$_2$,
(25) CF$_3$,
(26) CH$_2$CF$_3$,
(27) OCF$_3$, and
(28) OCH$_2$CF$_3$, wherein phenyl, naphthyl, heteroaryl, cycloalkyl, and heterocycloalkyl are unsubstituted or substituted with one to three substituents independently selected from halogen, hydroxy, oxo, C$_{1-4}$ alkyl, trifluoromethyl, and C$_{1-4}$ alkoxy, and wherein any methylene (CH$_2$) carbon atom in R$^3$ is unsubstituted or substituted with one to two groups independently selected from halogen, hydroxy, and C$_{1-4}$ alkyl, or wherein two substituents when on the same methylene (CH$_2$) group are taken together with the carbon atom to which they are attached to form a cyclopropyl group;

R$^4$ is selected from the group consisting of:
(1) —(CH$_2$)—N(R$^5$)—NR$^5$R$^6$,
(2) —(CH$_2$)—N(R$^5$)—(CH$_2$)$_{1-3}$—NR$^5$R$^6$,
(3) —(CH$_2$)—N(R$^5$)—C(=NR$^5$)—NR$^5$R$^6$,
(4) —(CH$_2$)—N(R$^5$)—(CH$_2$)$_{1-3}$—N(R$^5$)—(C=NR$^5$)—NR$^5$R$^6$,
(5) —(CH$_2$)—N(R$^5$)—(CH$_2$)$_{0-2}$—C(R$^5$)(N(R$^5$)$_2$)—(CH$_2$)$_{1-2}$—OR$^6$,
(6) —(CH$_2$)—N(R$^5$)—(CH$_2$)$_{0-2}$—C(R$^5$)(N(R$^5$)$_2$)(CH$_2$)$_{1-2}$—R$^6$,
(7) —(CH$_2$)—N(R$^5$)—(CH$_2$)$_{0-2}$—C(R$^5$)(N(R$^5$)$_2$)(CH$_2$)$_{1-2}$—S—R$^6$,
(8) —(CH$_2$)—N(R$^5$)—(CH$_2$)$_{0-2}$—C(R$^5$)(N(R$^5$)$_2$)(CH$_2$)$_{1-4}$—NR$^5$R$^6$,
(9) —(CH$_2$)—N(R$^5$)—C(O)(CH$_2$)$_{0-2}$—C(R$^5$)(N(R$^5$)$_2$)(CH$_2$)$_{1-2}$—R$^6$,
(10) —(CH$_2$)—N(R$^5$)—C(O)(CH$_2$)$_{0-2}$—C(R$^5$)(N(R$^5$)$_2$)(CH$_2$)$_{1-2}$—S—R$^6$,
(11) —(CH$_2$)—N(R$^5$)—C(O)(CH$_2$)$_{0-2}$—C(R$^5$)(N(R$^5$)$_2$)(CH$_2$)$_{1-4}$—NR$^5$R$^6$, and
(12) —(CH$_2$)—N(R$^5$)—R$^9$, wherein (CH$_2$) is unsubstituted or substituted with one to three groups independently selected from halogen, C$_{1-4}$ alkyl, hydroxy, oxo, and C$_{1-4}$ alkoxy;

R$^5$ is selected from the group consisting of:
(1) hydrogen,
(2) C$_{1-6}$ alkyl, and
(3) C(O)C$_{1-6}$ alkyl, wherein alkyl is unsubstituted or substituted with one to three groups independently selected from halogen, C$_{1-4}$ alkyl, hydroxy, oxo, and C$_{1-4}$ alkoxy;

R$^6$ is selected from the group consisting of:
(1) hydrogen,
(2) C$_{1-6}$ alkyl,
(3) C(O)C$_{1-6}$ alkyl,
(4) —(CH$_2$)$_n$C$_{3-7}$ cycloalkyl,
(5) —(CH$_2$)$_n$C$_{2-7}$ heterocycloalkyl,
(6) —(CH$_2$)$_n$-phenyl,
(7) —(CH$_2$)$_n$-naphthyl,
(8) —(CH$_2$)$_n$-heteroaryl, and
(9) —(CH$_2$)$_n$C$_{3-7}$ bicycloalkyl, wherein alkyl, phenyl, heteroaryl, heterocycloalkyl, naphthyl, cycloalkyl, bicycloalkyl and (CH$_2$)$_n$ are unsubstituted or substituted with one to three groups independently selected from halogen, C$_{1-4}$ alkyl, hydroxy, and C$_{1-4}$ alkoxy, or wherein two R$^6$ groups together with the atom to which they are attached form a 4- to 8-membered mono- or bicyclic ring system optionally containing an additional heteroatom selected from O, S, and —NC$_{1-4}$ alkyl;

each R$^7$ and R$^8$ is independently selected from the group consisting of:
(1) hydrogen,
(2) amidino,
(3) C$_{1-4}$ alkyliminoyl,
(4) C$_{1-10}$ alkyl,
(5) —(CH$_2$)$_n$—C$_{3-7}$ cycloalkyl,
(6) —(CH$_2$)$_n$-phenyl,
(7) —(CH$_2$)$_n$-naphthyl, and
(8) —(CH$_2$)$_n$-heteroaryl, wherein phenyl, naphthyl, and heteroaryl are unsubstituted or substituted with one to three groups independently selected from R$^3$, and wherein alkyl and cycloalkyl are unsubstituted or substituted with one to three groups independently selected from R$^3$ and oxo;

R$^9$ is selected from the group consisting of:
(1) alanine,
(2) glycine,
(3) proline,
(4) cysteine,
(5) histidine,
(6) glutamine,
(7) aspartic acid,
(8) isoleucine,
(9) arginine,
(10) glutamic acid,
(11) lysine,
(12) serine,
(13) phenylalanine,
(14) leucine,
(15) threonine,
(16) tryptophan,
(17) methionine,
(18) valine,
(19) tyrosine,
(20) asparagine,
(21) 2-aminoadipic acid,
(22) beta-alanine,
(23) 2-aminoheptanedioic acid,
(24) 2-aminobutyric acid,
(25) 4-aminobutyric acid,
(26) 2,4-diaminobutyric acid,
(27) citrulline,
(28) cycloserine,
(29) norvaline,
(30) norleucine,
(31) ornithine,
(32) penicillamine,
(33) phenylglycine,
(34) phenylisoserine,
(35) phenylstatine,
(36) pipecolic acid,
(37) piperidine carboxylic acid,
(38) pyroglutamic acid,
(39) sarcosine,
(40) statine,
(41) allo-threonine,
(42) t-leucine,
(43) 2-aminoisobutyric acid, and
(44) 3-aminoisobutyric acid;

Z is selected from the group consisting of:
(1) C(R$^1$), and
(2) N;

r is 1 or 2;
s is 0, 1, or 2; and
n is 0, 1, 2, 3 or 4.

In yet a further embodiment of the compounds of the present invention, there are provided compounds of structural formula IIIa or IIIb of the indicated relative stereochemical configurations having the trans orientation of the difluorophenyl and piperidinecarbonyl substituents:

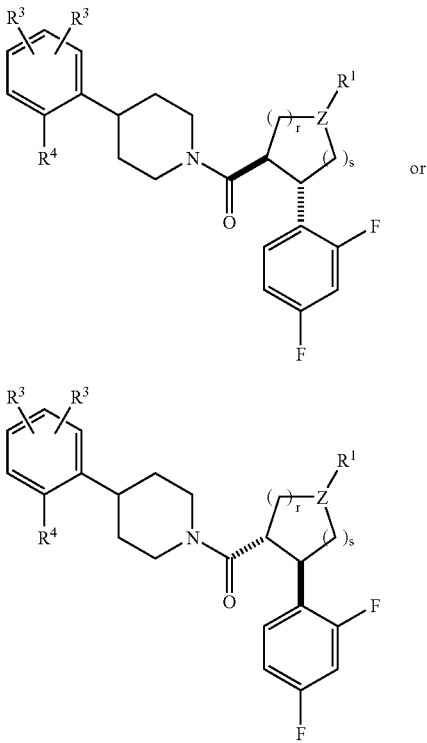

or a pharmaceutically acceptable salt thereof;

wherein:

$R^1$ is selected from the group consisting of: hydrogen, $C_{1-4}$ alkyl, and —$(CH_2)_{0-1}$ phenyl;

each $R^3$ is independently selected from the group consisting of:
(1) hydrogen,
(2) $C_{1-6}$ alkyl,
(3) —$(CH_2)_n$-phenyl,
(4) —$(CH_2)_n$-naphthyl,
(5) —$(CH_2)_n$-heteroaryl,
(6) —$(CH_2)_n$-heterocycloalkyl,
(7) —$(CH_2)_n C_{3-7}$ cycloalkyl,
(8) halogen,
(9) $OR^6$,
(10) —$(CH_2)_n N(R^6)_2$,
(11) —$(CH_2)_n C\equiv N$,
(12) —$(CH_2)_n CO_2 R^6$,
(13) $NO_2$,
(14) —$(CH_2)_n NR^6 SO_2 R^6$,
(15) —$(CH_2)_n SO_2 N(R^6)_2$,
(16) —$(CH_2)_n S(O)_{0-1} R^6$,
(17) —$(CH_2)_n NR^6 C(O)N(R^6)_2$,
(18) —$(CH_2)_n C(O)N(R^6)_2$,
(19) —$(CH_2)_n NR^6 C(O)R^6$,
(20) —$(CH_2)_n NR^6 CO_2 R^6$,
(21) —$(CH_2)_n NR^6 C(O)$-heteroaryl,
(22) —$(CH_2)_n C(O)NR^6 N(R^6)_2$,
(23) —$(CH_2)_n C(O)NR^6 NR^6 C(O)R^6$,
(24) $O(CH_2)_n C(O)N(R^6)_2$,
(25) $CF_3$,
(26) $CH_2 CF_3$,
(27) $OCF_3$, and
(28) $OCH_2 CF_3$, wherein phenyl, naphthyl, heteroaryl, cycloalkyl, and heterocycloalkyl are unsubstituted or substituted with one to three substituents independently selected from halogen, hydroxy, oxo, $C_{1-4}$ alkyl, trifluoromethyl, and $C_{1-4}$ alkoxy, and wherein any methylene ($CH_2$) carbon atom in $R^3$ is unsubstituted or substituted with one to two groups independently selected from halogen, hydroxy, and $C_{1-4}$ alkyl, or wherein two substituents when on the same methylene ($CH_2$) group are taken together with the carbon atom to which they are attached to form a cyclopropyl group;

$R^4$ is selected from the group consisting of:
(1) —$(CH_2)$—$N(R^5)$—$NR^5 R^6$,
(2) —$(CH_2)$—$N(R^5)$—$(CH_2)_{1-3}$—$NR^5 R^6$,
(3) —$(CH_2)$—$N(R^5)$—$C(=NR^5)$—$NR^5 R^6$,
(4) —$(CH_2)$—$N(R^5)$—$(CH_2)_{1-3}$—$N(R^5)$—$(C=NR^5)$—$NR^5 R^6$,
(5) —$(CH_2)$—$N(R^5)$—$(CH_2)_{0-2}$—$C(R^5)(N(R^5)_2)$—$(CH_2)_{1-2}$—$OR^6$,
(6) —$(CH_2)$—$N(R^5)$—$(CH_2)_{0-2}$—$C(R^5)(N(R^5)_2)$—$(CH_2)_{1-2}$—$R^6$,
(7) —$(CH_2)$—$N(R^5)$—$(CH_2)_{0-2}$—$C(R^5)(N(R^5)_2)$—$(CH_2)_{1-2}$—$S$—$R^6$,
(8) —$(CH_2)$—$N(R^5)$—$(CH_2)_{0-2}$—$C(R^5)(N(R^5)_2)$—$(CH_2)_{1-4}$—$NR^5 R^6$,
(9) —$(CH_2)$—$N(R^5)$—$C(O)(CH_2)_{0-2}$—$C(R^5)(N(R^5)_2)$—$(CH_2)_{1-2}$—$R^6$,
(10) —$(CH_2)$—$N(R^5)$—$C(O)(CH_2)_{0-2}$—$C(R^5)(N(R^5)_2)$—$(CH_2)_{1-2}$—$S$—$R^6$,
(11) —$(CH_2)$—$N(R^5)$—$C(O)(CH_2)_{0-2}$—$C(R^5)(N(R^5)_2)$—$(CH_2)_{1-4}$—$NR^5 R^6$, and
(12) —$(CH_2)$—$N(R^5)$—$R^9$, wherein ($CH_2$) is unsubstituted or substituted with one to three groups independently selected from halogen, $C_{1-4}$ alkyl, hydroxy, oxo, and $C_{1-4}$ alkoxy;

$R^5$ is selected from the group consisting of:
(1) hydrogen,
(2) $C_{1-6}$ alkyl, and
(3) $C(O)C_{1-6}$ alkyl, wherein alkyl is unsubstituted or substituted with one to three groups independently selected from halogen, $C_{1-4}$ alkyl, hydroxy, oxo, and $C_{1-4}$ alkoxy;

$R^6$ is selected from the group consisting of:
(1) hydrogen,
(2) $C_{1-6}$ alkyl,
(3) $C(O)C_{1-6}$ alkyl,
(4) —$(CH_2)_n C_{3-7}$ cycloalkyl,
(5) —$(CH_2)_n C_{2-7}$ heterocycloalkyl,
(6) —$(CH_2)_n$-phenyl,
(7) —$(CH_2)_n$-naphthyl,
(8) —$(CH_2)_n$-heteroaryl, and
(9) —$(CH_2)_n C_{3-7}$ bicycloalkyl, wherein alkyl, phenyl, heteroaryl, heterocycloalkyl, naphthyl, cycloalkyl, bicycloalkyl and $(CH_2)_n$ are unsubstituted or substituted with one to three groups independently selected from halogen, $C_{1-4}$ alkyl, hydroxy, and $C_{1-4}$ alkoxy, or wherein two $R^6$ groups together with the atom to which they are attached form a 4- to 8-membered mono- or bicyclic ring system optionally containing an additional heteroatom selected from O, S, and —$NC_{1-4}$ alkyl;

each $R^7$ and $R^8$ is independently selected from the group consisting of:
(1) hydrogen,
(2) amidino,
(3) $C_{1-4}$ alkyliminoyl,
(4) $C_{1-10}$ alkyl, (5) —(CH$_2$)$_n$-C$_{3-7}$ cycloalkyl,
(6) —(CH$_2$)$_n$-phenyl,
(7) —(CH$_2$)$_n$-naphthyl, and
(8) —(CH$_2$)$_n$-heteroaryl, wherein phenyl, naphthyl, and heteroaryl are unsubstituted or substituted with one to three groups independently selected from R$^3$, and wherein alkyl and cycloalkyl are unsubstituted or substituted with one to three groups independently selected from R$^3$ and oxo;

R$^9$ is selected from the group consisting of:
(1) alanine,
(2) glycine,
(3) proline,
(4) cysteine,
(5) histidine,
(6) glutamine,
(7) aspartic acid,
(8) isoleucine,
(9) arginine,
(10) glutamic acid,
(11) lysine,
(12) serine,
(13) phenylalanine,
(14) leucine,
(15) threonine,
(16) tryptophan,
(17) methionine,
(18) valine,
(19) tyrosine,
(20) asparagine,
(21) 2-aminoadipic acid,
(22) beta-alanine,
(23) 2-aminoheptanedioic acid,
(24) 2-aminobutyric acid,
(25) 4-aminobutyric acid,
(26) 2,4-diaminobutyric acid,
(27) citrulline,
(28) cycloserine,
(29) norvaline,
(30) norleucine,
(31) ornithine,
(32) penicillamine,
(33) phenylglycine,
(34) phenylisoserine,
(35) phenylstatine,
(36) pipecolic acid,
(37) piperidine carboxylic acid,
(38) pyroglutamic acid,
(39) sarcosine,
(40) statine,
(41) allo-threonine,
(42) t-leucine,
(43) 2-aminoisobutyric acid, and
(44) 3-aminoisobutyric acid;

Z is selected from the group consisting of:
(1) C(R$^1$), and
(2) N;

r is 1 or 2;
s is 0, 1, or 2; and
n is 0, 1, 2, 3, or 4.

In yet a further embodiment of the compounds of the present invention, there are provided compounds of structural formula IVa or IVb

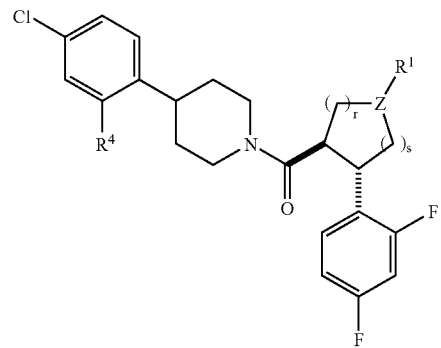
(IVa)

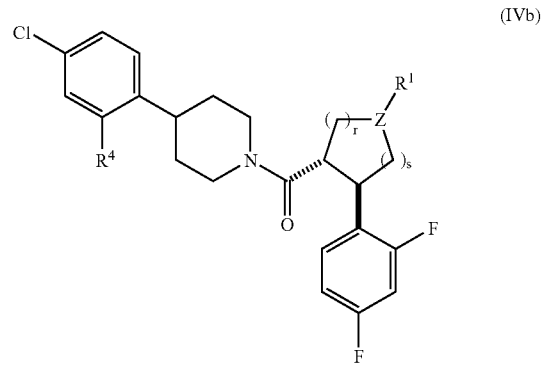
(IVb)

wherein R$^1$, R$^2$, R$^3$, R$^4$, r, s, n, p, and q are as defined supra; and pharmaceutically acceptable salts thereof.

In yet a further embodiment of the compounds of the present invention, there are provided compounds of structural formula Va or Vb

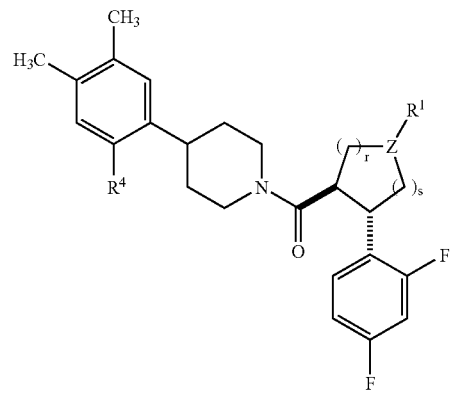
(Va)
or

-continued (Vb)

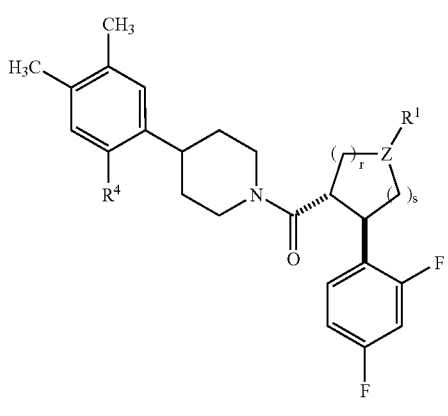

wherein R[1], R[2], R[3], R[4], r, s, n, p, and q are as defined supra; and pharmaceutically acceptable salts thereof.

In yet a further embodiment of the compounds of the present invention, there are provided compounds of structural formula VIa or VIb:

(VIa)

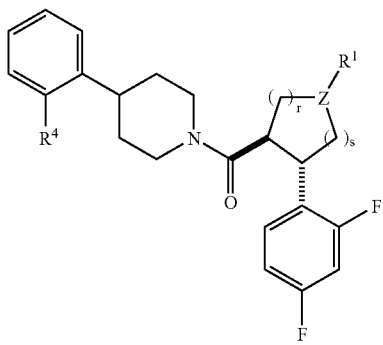

or (VIb)

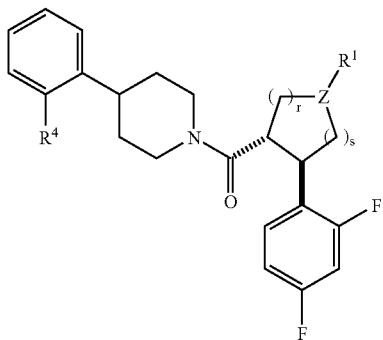

wherein R[1], R[2], R[3], R[4], r, s, n, p, and q are as defined supra; and pharmaceutically acceptable salts thereof.

Illustrative but nonlimiting examples of compounds of the present invention that are useful as melanocortin-4 receptor agonists are the following:

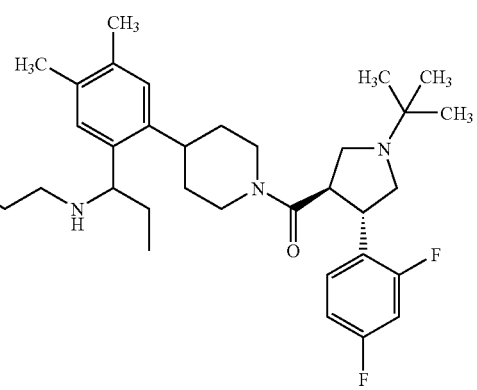

-continued

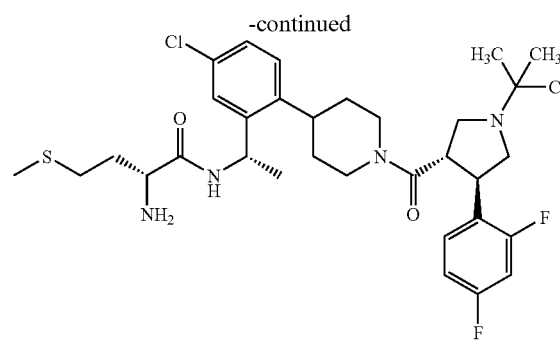

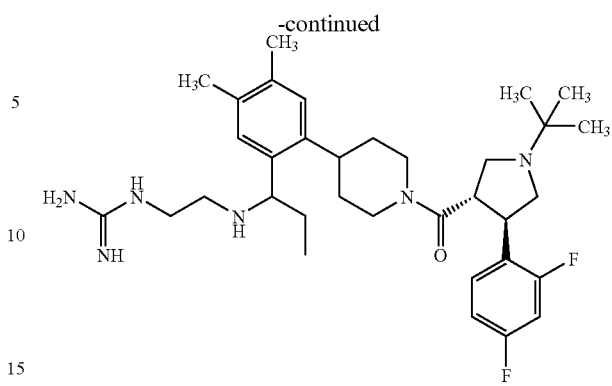

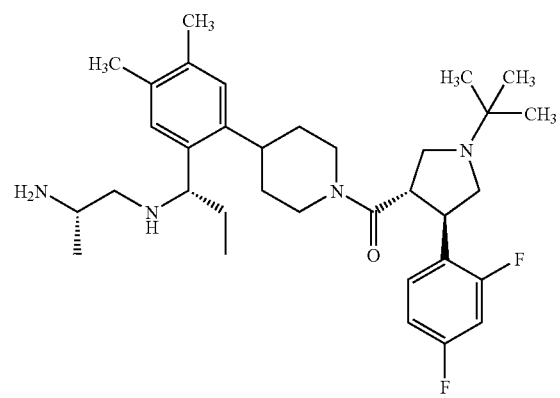

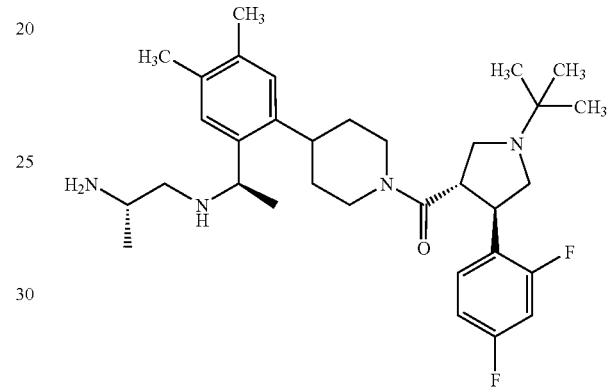

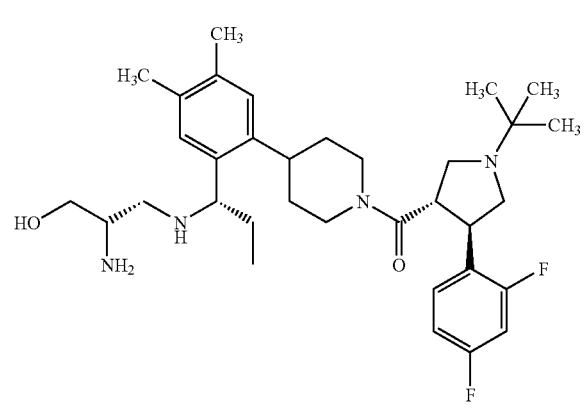

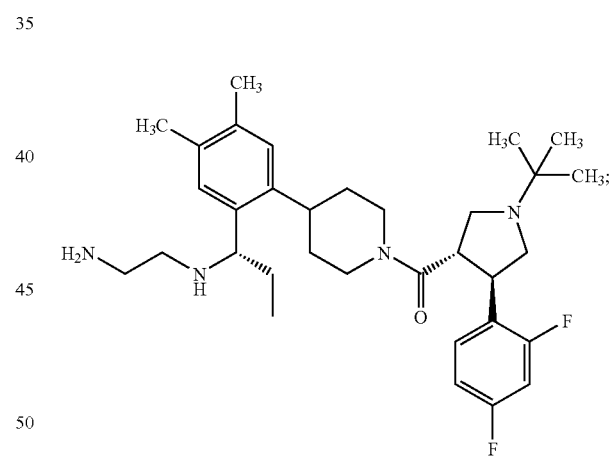

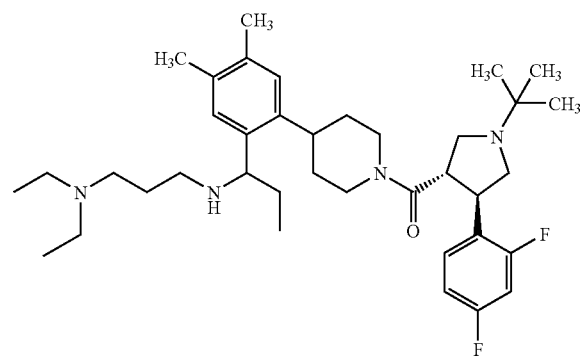

or a pharmaceutically acceptable salt thereof.

The compounds of structural formula I are effective as melanocortin receptor agonists and are particularly effective as selective agonists of MC-4R. They are therefore useful for the treatment and/or prevention of disorders responsive to the activation of MC-4R, such as obesity, diabetes as well as male and/or female sexual dysfunction, in particular, erectile dysfunction, and further in particular, male erectile dysfunction.

Another aspect of the present invention provides a method for the treatment or prevention of obesity or diabetes in a mammal in need thereof which comprises administering to said mammal a therapeutically or prophylactically effective amount of a compound of structural formula I.

Another aspect of the present invention provides a method for the treatment or prevention of male or female sexual dysfunction including erectile dysfunction which comprises administering to a mammal in need of such treatment or prevention a therapeutically or prophylactically effective amount of a compound of structural formula I.

Another aspect of the present invention provides a pharmaceutical composition comprising a compound of structural formula I and a pharmaceutically acceptable carrier.

Another aspect of the present invention provides a method for the treatment or prevention of male or female sexual dysfunction including erectile dysfunction which comprises administering to a mammal in need of such treatment or prevention a therapeutically or prophylactically effective amount of a compound of structural formula I in combination with a therapeutically effective amount of another agent known to be useful for the treatment of these conditions.

Yet another aspect of the present invention provides a method for the treatment or prevention of obesity which comprises administering to a mammal in need of such treatment or prevention a therapeutically or prophylactically effective amount of a compound of structural formula I in combination with a therapeutically effective amount of another agent known to be useful for the treatment of this condition.

Yet another aspect of the present invention relates to the use of a compound of formula I for the manufacture of a medicament useful for the treatment or prevention, or suppression of a disease mediated by the melanocortin-4 receptor in a mammal in need thereof.

Yet another aspect of the present invention relates to the use of a compound of formula I for the manufacture of a medicament useful for the treatment or prevention, or suppression of a disease mediated by the melanocortin-4 receptor, wherein the disease is selected from the group consisting of: obesity, diabetes, male sexual dysfunction and female sexual dysfunction in a mammal in need thereof.

Yet another aspect of the present invention relates to the use of a compound of formula I for the manufacture of a medicament useful for the treatment or prevention, or suppression of male erectile dysfunction in a mammal in need thereof.

Melanocortin receptor agonist compounds can be provided in kit. Such a kit typically contains an active compound in dosage forms for administration. A dosage form contains a sufficient amount of active compound such that a beneficial effect can be obtained when administered to a subject during regular intervals, such as 1 to 6 times a day, during the course of 1 or more days. Preferably, a kit contains instructions indicating the use of the dosage form for weight reduction (e.g., to treat obesity or overweight) or sexual dysfunction, and the amount of dosage form to be taken over a specified time period.

Throughout the instant application, the following terms have the indicated meanings:

The term "alkyl", as well as other groups having the prefix "alk", such as alkoxy, alkanoyl, means carbon chains of the designated length which may be in a straight or branched configuration, or combinations thereof. Examples of allyl groups include methyl, ethyl, n-propyl, isopropyl, n-butyl, 1-methylpropyl, 2-methylpropyl, tert-butyl, n-pentyl, 1-methylbutyl, 2-methylbutyl, 3-methylbutyl, 1,2-dimethylpropyl, 1,1-dimethylpropyl, 2,2-dimethylpropyl, n-hexyl, 1-methylpentyl, 2-methylpentyl, 3-methylpentyl, 4-methylpentyl, 1-ethylbutyl, 2-ethylbutyl, 3-ethylbutyl, 1,1dimethyl butyl, 1,2-dimethylbutyl, 1,3-dimethylbutyl, 2,2-dimethylbutyl, 2,3-dimethylbutyl, 3,3dimethyl butyl, n-heptyl, 1-methylhexyl, 2-methylhexyl, 3-methylhexyl, 4-methylhexyl, 5-methylhexyl, 1-ethylpentyl, 2-ethylpentyl, 3-ethylpentyl, 4-ethylpentyl, 1-propylbutyl, 2-propylbutyl, 3-propylbutyl, 1,1-dimethylpentyl, 1,2-dimethylpentyl, 1,3-dimethylpentyl, 1,4-dimethylpentyl, 2,2-dimethylpentyl, 2,3-dimethylpentyl, 2,4-dimethylpentyl, 3,3-dimethylpentyl, 3,4-dimethylpentyl, 4,4-dimethylpentyl, 1-methyl-1-ethylbutyl, 1-methyl-2-ethylbutyl, 2-methyl-2-ethylbutyl, 1-ethyl-2-methylbutyl, 1-ethyl-3-methylbutyl, 1,1-diethylpropyl, n-octyl, n-nonyl, and the like.

The term "alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

The term "alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

The term "amino acid" or "amino acid residue" refers, for example, to the stereoisomeric forms, i.e. the D or L forms, or a mixture of D and L forms, of an amino acid or amino acid residue such as, but not limited to: alanine, glycine, proline, cysteine, histidine, glutamine, aspartic acid, isoleucine, arginine, glutamic acid, lysine, serine, phenylalanine, leucine, threonine, tryptophan, methionine, valine, tyrosine, asparagine, 2-aminoadipic acid, beta-alanine, 2-aminoheptanedioic acid, 2-aminobutyric acid, 4-aminobutyric acid, 2,4-diaminobutyric acid, citrulline, cycloserine, norvaline, norleucine, ornithine, penicillamine, phenylglycine, phenylisoserine, phenylstatine, pipecolic acid, piperidine carboxylic acid, pyroglutamic acid, sarcosine, statine, allo-threonine, t-leucine, 2-aminoisobutyric acid, and 3-aminoisobutyric acid. The point of attachment of the amino acids in the compounds of structural formula I, IIa, IIb, IIIa, IIIb, IVa, IVb, Va, Vb, VIa and VIb is at the carboxylic acid terminal of the amino acid.

The term "halogen" includes fluorine, chlorine, bromine and iodine.

The term "$C_{1-4}$ alkyliminoyl" means $C_{1-3}C(\!=\!NH)\!-\!$.

The term "aryl" includes mono- or bicyclic aromatic rings containing only carbon atoms. Examples of aryl include phenyl and naphthyl.

The term "heteroaryl" includes mono- and bicyclic aromatic rings containing from 1 to 4 heteroatoms selected from nitrogen, oxygen and sulfur. Examples thereof include, but are not limited to, pyridinyl, furyl, furanyl, thienyl, pyrrolyl, oxazolyl, thiazolyl, triazolyl, triazinyl, tetrazolyl, thiadiazolyl, imidazolyl, isoxazolyl, isothiazolyl, oxadiazolyl, pyrazolyl, pyrimidinyl, pyrazinyl, pyridazinyl, quinolyl, isoquinolyl, benzimidazolyl, benzofuryl, benzothienyl, indolyl, benzthiazolyl, benzoxazolyl, and the like. In one embodiment of the present invention, heteroaryl is selected from the group consisting of: pyridinyl, furyl, furanyl, thienyl, pyrrolyl, oxazolyl, thiazolyl, triazolyl, triazinyl, tetrazolyl, thiadiazolyl, imidazolyl, pyrazolyl, isoxazolyl, isothiazolyl, oxathiazolyl, pyrimidinyl, pyrazinyl, pyridazinyl, quinolyl, isoquinolyl, benzimidazolyl, benzofuryl, benzothienyl, indolyl, isoindoline, benzthiazolyl, and benzoxazolyl. Bicyclic heteroaromatic rings include, but are not limited to, benzothiadiazole, indole, benzothiophene, benzofuran, benzimidazole, benzisoxazole, benzothiazole, quinoline, quinazoline, benzotriazole, benzoxazole, isoquinoline, purine, furopyridine, thienopyridine, benzisodiazole, triazolopyrimidine, and 5,6,7,8-tetrahydroquinoline.

The term "cycloalkyl" includes mono- or bicyclic non-aromatic rings containing only carbon atoms. Examples of cycloalkyl include, but are not limited to, cyclopropyl, cyclobutyl, cyclopentyl, cyclohexyl, and cycloheptyl.

The term "heterocycloalkyl" is intended to include non-aromatic heterocycles containing one to four heteroatoms selected from nitrogen, oxygen and sulfur. Examples of heterocycloalkyl include, but are not limited to, azetidine, piperidine, morpholine, thiamorpholine, pyrrolidine, imidazolidine, tetrahydrofuran, piperazine, 1-thia-4-aza-cyclohexane, 1-aza-4-thia-cyclohexane, and 1,3 oxazolidine.

Certain of the above defined terms may occur more than once in the above formula and upon such occurrence each term shall be defined independently of the other; thus for example, $NR^4R^4$ may represent $NH_2$, $NHCH_3$, $N(CH_3)CH_2CH_3$, and the like.

The term "subject" means a mammal. One embodiment of the term "mammal" is a "human," said human being either male or female.

The term "mammal in need thereof" refers to a mammal who is in need of treatment or prophylaxis as determined by a researcher, veterinarian, medical doctor or other clinician.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

By a melanocortin receptor "agonist" is meant an endogenous or drug substance or compound that can interact with a melanocortin receptor and initiate a pharmacological response characteristic of the melanocortin receptor. By a melanocortin receptor "antagonist" is meant a drug or a compound that opposes the melanocortin receptor-associated responses normally induced by another bioactive agent. The "agonistic" properties of the compounds of the present invention were measured in the functional assay described below. The functional assay discriminates a melanocortin receptor agonist from a melanocortin receptor antagonist.

By "binding affinity" is meant the ability of a compound/drug to bind to its biological target, in the the present instance, the ability of a compound of structural formula I to bind to a melanocortin receptor. Binding affinities for the compounds of the present invention were measured in the binding assay described below and are expressed as $IC_{50}$'s.

"Efficacy" describes the relative intensity with which agonists vary in the response they produce even when they occupy the same number of receptors and with the same affinity. Efficacy is the property that enables drugs to produce responses. Properties of compounds/drugs can be categorized into two groups, those which cause them to associate with the receptors (binding affinity) and those that produce a stimulus (efficacy). The term "efficacy" is used to characterize the level of maximal responses induced by agonists. Not all agonists of a receptor are capable of inducing identical levels of maximal responses. Maximal response depends on the efficiency of receptor coupling, that is, from the cascade of events, which, from the binding of the drug to the receptor, leads to the desired biological effect.

The functional activities expressed as $EC_{50}$'s and the "agonist efficacy" for the compounds of the present invention at a particular concentration were measured in the functional assay described below.

Optical Isomers—Diastereomers—Geometric Isomers—Tautomers

Compounds of structural formula I contain one or more asymmetric centers and can thus occur as racemates and racemic mixtures, single enantiomers, diastereomeric mixtures and individual diastereomers. The present invention is meant to comprehend all such isomeric forms of the compounds of structural formula I.

Some of the compounds described herein contain olefinic double bonds, and unless specified otherwise, are meant to include both E and Z geometric isomers.

Some of the compounds described herein may exist as tautomers such as keto-enol tautomers. The individual tautomers as well as mixtures thereof are encompassed within the compounds of structural formula I.

Compounds of structural formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general formulae I, IIa, IIb, IIIa, IIIb, IVa, IVb, Va, Vb, VIa, and VIb may be obtained by stereospecific synthesis using optically pure starting materials or reagents of known absolute configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Particularly preferred are citric, fumaric, hydrobromic, hydrochloric, maleic, phosphoric, sulfuric, and tartaric acids.

It will be understood that, as used herein, references to the compounds of Formula I are meant to also include the pharmaceutically acceptable salts, such as the hydrochloride salts.

Utility

Compounds of formula I are melanocortin receptor agonists and as such are useful in the treatment, control or prevention of diseases, disorders or conditions responsive to the activation of one or more of the melanocortin receptors including, but are not limited to, MC-1, MC-2, MC-3, MC-4, or MC-5. Such diseases, disorders or conditions include, but are not limited to, obesity, diabetes mellitus, hypertension, hyperlipidemia, osteoarthritis, cancer, gall bladder disease, sleep apnea, depression, anxiety, compulsion, neuroses, insomnia/sleep disorder, substance abuse, pain, male and female sexual dysfunction, fever, inflammation, immunemodulation, rheumatoid arthritis, skin tanning, acne and other skin disorders, neuroprotective and cognitive and memory enhancement including the treatment of Alzheimer's disease. Some compounds encompassed by formula I show highly selective affinity for the melanocortin-4 receptor (MC-4R) relative to MC-1R, MC-2R, MC-3R, and MC-5R, which makes them especially useful in the prevention and treatment of obesity, as well as male and/or female sexual dysfunction, including erectile dysfunction.

The compositions of the present invention are useful for the treatment or prevention of disorders associated with excessive food intake, such as obesity and obesity-related disorders. The obesity herein may be due to any cause, whether genetic or environmental.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovary disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, also known as syndrome X, insulin resistance syndrome, reproductive hormone abnormalities, sexual and reproductive dysfunction, such as impaired fertility, infertility, hypogonadism in males and hirsutism in females, fetal defects associated with maternal obesity, gastrointestinal motility disorders, such as obesity-related gastro-esophageal reflux, respiratory disorders, such as obesity-hypoventilation syndrome (Pickwickian syndrome), breathlessness, cardiovascular disorders, inflammation, such as systemic inflammation of the vasculature, arteriosclerosis, hypercholesterolemia, hyperuricaemia, lower back pain, gallbladder disease, gout, kidney cancer, and increased anesthetic risk. The compositions of the present invention are also useful for reducing the risk of secondary outcomes of obesity, such as reducing the risk of left ventricular hypertrophy. The compositions of the present invention are also useful to treat Alzheimer's disease.

The term "metabolic syndrome", also known as syndrome X, is defined in the Third Report of the National Cholesterol Education Program Expert Panel on Detection, Evaluation and Treatment of High Blood Cholesterol in Adults (ATP-III). E. S. Ford et al., JAMA, vol. 287 (3), Jan. 16, 2002, pp 356-359. Briefly, a person is defined as having metabolic syndrome if the person has three or more of the following symptoms: abdominal obesity, hypertriglyceridemia, low HDL cholesterol, high blood pressure, and high fasting plasma glucose. The criteria for these are defined in ATP-III.

The term "diabetes," as used herein, includes both insulin-dependent diabetes mellitus (i.e., IDDM, also known as type I diabetes) and non-insulin-dependent diabetes mellitus (i.e., NIDDM, also known as Type II diabetes). Type I diabetes, or insulin-dependent diabetes, is the result of an absolute deficiency of insulin, the hormone which regulates glucose utilization. Type f diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The compositions of the present invention are useful for treating both Type I and Type II diabetes. The compositions are especially effective for treating Type II diabetes. The compounds or combinations of the present invention are also useful for treating and/or preventing gestational diabetes mellitus.

Treatment of diabetes mellitus refers to the administration of a compound or combination of the present invention to treat diabetes. One outcome of treatment may be decreasing the glucose level in a subject with elevated glucose levels. Another outcome of treatment may be improving glycemic control. Another outcome of treatment may be decreasing insulin levels in a subject with elevated insulin levels. Another outcome of treatment may be decreasing plasma triglycerides in a subject with elevated plasma triglycerides. Another outcome of treatment may be lowering LDL cholesterol in a subject with high LDL cholesterol levels. Another outcome of treatment may be increasing HDL cholesterol in a subject with low HDL cholesterol levels. Another outcome may be decreasing the LDL/HDL ratio in a subject in need thereof. Another outcome of treatment may be increasing insulin sensitivity. Another outcome of treatment may be enhancing glucose tolerance in a subject with glucose intolerance. Another outcome of treatment may be decreasing insulin resistance in a subject with increased insulin resistance or elevated levels of insulin. Another outcome may be decreading triglycerides in a subject with elevated triglycerides. Yet another outcome may be improving LDL cholestrol, non-HDL cholesterol, triglyceride, HDL cholesterol or other lipid analyte profiles.

Prevention of diabetes mellitus refers to the administration of a compound or combination of the present invention to prevent the onset of diabetes in a mammal at risk thereof.

"Obesity" is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 kg/m². In Asian countries, including Japan, an "obese subject" refers to a subject with at least one obesity-induced or obesity-related co-morbidity that requires weight reduction or that would be improved by weight reduction, with a BMI greater than or equal to 25 kg/m². In Asia-Pacific, a "subject at risk of obesity" is a subject with a BMI of greater than 23 kg/m² to less than 25 kg/m².

As used herein, the term "obesity" is meant to encompass all of the above definitions of obesity.

Obesity-induced or obesity-related co-morbidities include, but are not limited to, diabetes, non-insulin dependent diabetes mellitus—type II (2), impaired glucose tolerance, impaired fasting glucose, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

Treatment of obesity and obesity-related disorders refers to the administration of the compounds or combinations of the present invention to reduce or maintain the body weight of an obese subject. One outcome of treatment may be reducing the body weight of an obese subject relative to that subject's body weight immediately before the administration of the compounds or combinations of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in subjects in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds or combinations of the present invention to reduce or maintain the body weight of a subject at risk of obesity. One outcome of prevention may be reducing the body weight of a subject at risk of obesity relative to that subject's body weight immediately before the administration of the compounds or combinations of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovary disease, cardiovascular diseases, osteoarthritis, dermatological disorders, hypertension, insulin resistance, hypercholesterolemia, hypertriglyceridemia, and cholelithiasis.

"Male sexual dysfunction" includes impotence, loss of libido, and erectile dysfunction.

"Erectile dysfunction" is a disorder involving the failure of a male mammal to achieve erection, ejaculation, or both. Symptoms of erectile dysfunction include an inability to achieve or maintain an erection, ejaculatory failure, premature ejaculation, or inability to achieve an orgasm. An increase in erectile dysfunction and sexual dysfunction can have numerous underlying causes, including but not limited to (1) aging, (b) an underlying physical dysfunction, such as trauma, surgery, and peripheral vascular disease, and (3) side-effects resulting from drug treatment, depression, and other CNS disorders.

Treatment of male sexual dysfunction refers to the administration of a compound or combination of the present invention to treat impotence and/or loss of libido, and/or erectile dysfunction in a male mammal in need thereof. One outcome of treatment may be a decrease in impotence. Another outcome of treatment may be an increase in libido. Yet another outcome of treatment may be a decrese in the magnitude or frequency of erectile dysfunction.

Treatment of male sexual dysfunction refers to the administration of a compound or combination of the present invention to treat one or more of the symptoms of male sexual dysfunction in a male mammal in need thereof. One outcome of treatment may be increasing the ability to achieve an erection. Another outcome of treatment may be increasing the ability to maintain an erection. Another outcome of treatment may be reducing ejaculatory failure. Another outcome of treatment may be decreasing premature ejaculation. Yet another outcome of treatment may be increasing the ability to achieve an orgasm.

Prevention of male sexual dysfunction and male erectile dysfunction refers to the administration of the compounds or combinations of the present invention to prevent the symptoms of sexual dysfunction and erectile dysfunction in a male mammal at risk thereof.

"Female sexual dysfunction" can be seen as resulting from multiple components including dysfunction in desire, sexual arousal, sexual receptivity, and orgasm related to disturbances in the clitoris, vagina, periurethral glans, and other trigger points of sexual function. In particular, anatomic and functional modification of such trigger points may diminish the orgasmic potential in breast cancer and gynecologic cancer patients. Treatment of female sexual dysfunction with an MC-4 receptor agonist can result in improved blood flow, improved lubrication, improved sensation, facilitation of reaching orgasm, reduction in the refractory period between orgasms, and improvements in arousal and desire. In a broader sense, "female sexual dysfunction" also incorporates sexual pain, premature labor, and dysmenorrhea.

The terms "administration of" and or "administering" a compound should be understood to mean providing a compound of the invention or a prodrug of a compound of the invention to a subject in need of treatment.

The administration of the compounds of the present invention in order to practice the present methods of therapy is carried out by administering a therapeutically or prophylactially effective amount of the compound to a subject in need of such treatment or prophylaxis. The need for a prophylactic administration according to the methods of the present invention is determined via the use of known risk factors.

The term "therapeutically effective amount" as used herein means the amount of the active compound that will elicit the biological or medical response in a tissue, system, subject, mammal, or human that is being sought by the researcher, veterinarian, medical doctor or other clinician, which includes alleviation of the symptoms of the disorder being treated. The novel methods of treatment of this invention are for disorders known to those skilled in the art.

The term "prophylactically effective amount" as used herein means the amount of the active compound that will elicit the biological or medical response in a tissue, system, subject, mammal, or human that is being sought by the researcher, veterinarian, medical doctor or other clinician, to prevent the onset of the disorder in subjects as risk for obesity or the disorder.

The therapeutically or prophylactically effective amount, or dosage, of an individual compound is determined, in the final analysis, by the physician in charge of the case, but depends on factors such as the exact disease to be treated, the severity of the disease and other diseases or conditions from which the subject suffers, the chosen route of administration, other drugs and treatments which the subject may concomitantly require, and other factors in the physician's judgement.

Administration and Dose Ranges

Any suitable route of administration may be employed for providing a mammal, especially a human with an effective amount, or dosage, of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally or topically.

When treating obesity, in conjunction with diabetes and/or hyperglycemia, or alone, generally satisfactory results are obtained when the compounds of the present invention are administered at a daily dosage of from about 0.001 milligram to about 100 milligrams per kilogram of body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response. It may be necessary to use dosages outside these limits in some cases.

When treating diabetes mellitus and/or hyperglycemia, as well as other diseases or disorders for which compounds of formula I are useful, generally satisfactory results are obtained when the compounds of the present invention are administered at a daily dosage of from about 0.001 milligram to about 100 milligram per kilogram of body weight, preferably given in a single dose or in divided doses two to six times a day, or in sustained release form. In the case of a 70 kg adult human, the total daily dose will generally be from about 0.07 milligrams to about 350 milligrams. This dosage regimen may be adjusted to provide the optimal therapeutic response. It may be necessary to use dosages outside these limits in some cases.

When treating an obesity-related disorder, generally satisfactory results are obtained when the compounds of the present invention are administered at a daily dosage of from about 0.001 milligram to about 100 milligrams per kilogram of animal body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response.

For the treatment of sexual dysfunction compounds of the present invention are given in a dose range of 0.001 milligram to about 100 milligram per kilogram of body weight, preferably as a single dose orally or as a nasal spray.

In the case where an oral composition is employed, a suitable dosage range is, e.g. from about 0.01 mg to about 1500 mg of a compound of Formula I per day, preferably from about 0.1 mg to about 10 mg per day. For oral administration, the compositions are preferably provided in the form of tablets containing from 0.01 to 1,000 mg, preferably 0.01, 0.05, 0.1, 0.5, 1, 2.5, 5, 10, 15, 20, 25, 30, 40, 50, 100, 250, 500, 750, 1000, 1250 or 1500 milligrams of the active ingredient for the symptomatic adjustment of the dosage to the subject to be treated.

For use where a composition for intravenous administration is employed, a suitable dosage range is from about 0.001 mg to about 100 mg, preferably from 0.01 mg to about 50 mg, more preferably 0.1 mg to 10 mg, of a compound of Formula I per kg of body weight per day. This dosage regimen may be adjusted to provide the optimal therapeutic response. It may be necessary to use dosages outside these limits in some cases.

For the treatment of diseases of the eye, ophthalmic preparations for ocular administration comprising 0.001-1% by weight solutions or suspensions of the compounds of Formula I in an acceptable ophthalmic formulation may be used.

The magnitude of prophylactic or therapeutic dosage of the compounds of the present invention will, of course, vary depending on the particular compound employed, the mode of administration, the condition being treated and the severity of the condition being treated. It will also vary according to the age, weight and response of the individual subject. Such dosage may be ascertained readily by a person skilled in the art.

Combination Therapy

Compounds of structural formula I may be used in combination with other drugs that are used in the treatment/prevention/suppression or amelioration of the diseases or conditions for which compounds of structural formula I are useful. Such other drugs may be administered, by a route and in an amount commonly used therefor, contemporaneously or sequentially with a compound of structural formula I. When a compound of structural formula I is used contemporaneously with one or more other drugs, a pharmaceutical composition containing such other drugs in addition to the compound of structural formula I is preferred. When a composition of the present invention is used contemporaneously with one or more other drugs, a pharmaceutical composition in unit dosage form containing such other drugs and the composition of the present invention is preferred. However, the combination therapy also includes therapies in which the composition of the present invention and one or more other drugs are administered on different overlapping schedules. It is also contemplated that when used in combination with one or more other active ingredients, the composition of the present invention and the other active ingredients may be used in lower doses than when each is used singly. Accordingly, the pharmaceutical compositions of the present invention include those that also contain one or more other active ingredients, in addition to a compound of structural formula I.

Examples of other active ingredients that may be combined with a compound of structural formula I for the treatment or prevention of obesity and/or diabetes, either administered separately or in the same pharmaceutical compositions, include, but are not limited to:

(a) insulin sensitizers including (i) PPARγ agonists such as the glitazones (e.g. ciglitazone; darglitazone; troglitazone, pioglitazone, englitazone, isaglitazone (MCC-555), BRL49653, rosiglitazone; CLX0921; 5-BTZD), GW0207, LG-100641, and LY-300512, and the like), and compounds disclosed in WO97/10813, WO97/27857, 97/28115, 97/28137 and 97/27847; ii) biguanides such as metformin (Glucophage®), buformin, and phenformin;

(b) insulin or insulin mimetics, such as biota, LP-100, novarapid, insulin detemir, insulin lispro, insulin glargine, insulin zinc suspension (lente and ultralente); Lys-Pro insulin, GLP-1 (73-7) (insulintropin); and GLP-1 (7-36)-NH$_2$);

(c) sulfonylureas, such as tolbutamide and glipizide, acetohexamide; chlorpropamide; diabinese; glibenclamide; glyburide; glimepiride; gliclazide; glipentide; gliquidone; glisolamide; and tolazamide;

(d) α-glucosidase inhibitors (such as acarbose, adiposine; carniglibose; emiglitate; miglitol; voglibose; pradimicin-Q; salbostatin; CKD-711; MDL-25,637; MDL-73,945; and MOR 14, and the like);

(e) cholesterol lowering agents such as (i) HMG-CoA reductase inhibitors (lovastatin, simvastatin, pravastatin, fluvastatin, atorvastatin, itavastatin, rivastatin, rosuvastatin, ZD-4522, and other statins), (ii) sequestrants (cholestyramine, colestipol and a dialkylaminoalkyl derivatives of a cross-linked dextran, colesevelum, Colestid®; LoCholest®, and the like, (ii) nicotinyl alcohol nicotinic acid or a salt thereof, (iii) proliferator-activater receptor a agonists such as fenofibric acid derivatives (gemfibrozil, clofibrate, fenofibrate and benzafibrate), (iv) inhibitors of cholesterol absorption for example beta-sitosterol, stanol esters, sterol glycosides such as tiqueside; and azetidinones such as ezetimibe, efucimibe, KY 505, SMP797, and the like, and (acyl CoA:cholesterol acyltransferase) inhibitors for example melinamide, and avasimibe, (v) anti-oxidants such as probucol, (vi) vitamin E, and (vii) thyromimetics;

(f) PPARδ agonists, such as those disclosed in WO97/28149, and such as GW 501516, and GW 590735, and the like;

(g) anti-obesity serotonergic agents, such as fenfluramine, dexfenfluramine, phentermine, and sibutramine;

(h) β3-adrenoreceptor agonists, such as AD9677/TAK677 (Dainippon/Takeda), CL-316,243, SB 418790, BRL-37344, L-796568, BMS-196085, BRL-35135A, CGP12177A, GW 427353, BTA-243, Trecadrine, Zeneca D7114, SR 59119A, and such as those disclosed in U.S. patent application Ser. No. 5,705,515, and U.S. Pat. No. 5,451,677 and PCT Patent Publications WO94/18161, WO95/29159, WO97/46556, WO98/04526 and WO98132753, WO 01174782, and WO 02/32897;

(i) pancreatic lipase inhibitors, such as orlistat (Xenical®), Triton WR1339, RHC80267, lipstatin, tetrahydrolipstatin, teasaponin, diethyl-umbelliferyl phosphate, FL-386, WAY-121898, Bay-N-3176, valilactone, esteracin, ebelactone A, ebelactone B, and RHC 80267, and those disclosed in PCT Application No. WO 01/77094, and U.S. Pat. Nos. 4,598,089. 4,452,813, 5,512,565, 5,391,571, 5,602,151, 4,405,644, 4,189,438, and 4,242,453;

(j) feeding behavior modifying agents, such as neuropeptide Y Y1 and Y5 antagonists, such as those disclosed in WO 97/19682, WO 97/20820, WO 97/20821, WO 97/20822, WO 97/20823, WO 01/14376, and U.S. Pat. No. 6,191,160; neuropeptide Y1 antagonists, such as BIBP3226, J-115814, BIBO 3304, LY-357897, CP-671906, GI-264879A, and those disclosed in U.S. Pat. No. 6,001,836, and PCT Patent Publication Nos. WO 96/14307, WO 01/23387, WO 99/51600, WO 01/85690, WO 01/85098, WO 01/85173, and WO 01/89528; and neuropeptide Y5 antagonists, such as 152,804, GW-569180A, GW-594884A, GW-587081X, GW-548118X, FR235,208, FR226928, FR 240662, FR252384, 1229U91, GI-264879A, CGP71683A, LY-377897, LY-366377, PD-160170, SR-120562A, SR-120819A, JCF-104, and H409/22; and those disclosed in U.S. Pat. Nos. 6,140,354, 6,191,160, 6,258,837, 6,313,298, 6,337,332, 6,329,395, 6,326,375, 6,335,345, and 6,340,683, European Patent Nos. EP-01010691, and EP-01044970, and PCT Patent Publication Nos. WO 97119682, WO 97/20820, WO 97/20821, WO 97/20822, WO 97120823, WO 98/27063, WO 00/107409, WO 00/185714, WO 00/185730, WO 00/64880, WO 00/68197, WO 00/69849, WO 01/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/20488, WO 02/22592, WO 02/48152, WO 02/49648 and WO 02/094789; and Norman et al., J. Med. Chem. 43:4288-4312 (2000);

(k) orexin-1 receptor antagonists, such as SB-334867-A, and those disclosed in PCT Patent Application Nos. WO 01/96302, WO 01/68609, WO 02/51232, WO 02/51838, and WO 03/023561;

(l) PPARα agonists such as described in WO 97/36579, and PPARα agonists such as beclofibrate, benzafibrate, ciprofibrate, clofibrate, etofibrate, fenofibrate, gemcabene, gemfibrozil, GW 7647, BM 170744, and LY518674; and other fibric acid derivatives, such as Atromid®, Lopid® and Tricor®, and the like;

(m) PPARγ antagonists as described in WO97/10813;

(n) serotonin reuptake inhibitors such as fluoxetine, paroxetine, and sertraline;

(o) growth hormone secretagogues, such as MK-0677, and growth hormone secretagogue receptor agonists/antagonists, such as NN703, hexarelin, SM-130686, CP-424,391, L-692, 429 and L-163,255, and such as those disclosed in U.S. Pat. Nos. 5,536,716, and 6,358,951, U.S. Patent Application Nos. 2002/049196 and 2002/022637, and PCI Application Nos. WO 01/56592 and WO 02/32888;

(p) cannabinoid receptor ligands, such as cannabinoid $CB_1$ receptor antagonists or inverse agonists, such as rimonabant (Sanofi-Synthelabo), and SR-147778 and SR 141716A (Sanofi Synthelabo), SLV-319 (Solvay), BAY 65-2520 (Bayer), and those disclosed in U.S. Pat. Nos. 5,532,237, 4,973,587, 5,013,837, 5,081,122, 5,112,820, 5,292,736, 5,624,941, 6,028,084, PCT Application Nos. WO 96/33159, WO 98/33765, WO98/43636, WO98/43635, WO 01/09120, W098/31227, WO98/41519, WO98/37061, WO00/10967, WO00/10968, WO97/29079, WO99/02499, WO 01/58869, WO 01/64632, WO 01/64633, WO 01/64634, W002/076949, WO 03/0060007, and WO 03/007887; and EPO Application No. EP-658546, EP-656354, EP-576357;

(q) protein tyrosine phosphatase-1B (PTP-1B) inhibitors; and (r) anti-obesity agents, such as (1) melanin-concentrating hormone (MCH) receptor antagonists, such as those disclosed in WO 01/21577 and WO 01/21169; (2) melanin-concentrating hormone 1 receptor (MCH1R) antagonists, such as T-226296 (Takeda), SNP-7941, and those disclosed in PCT Patent Application Nos. WO 01/82925, WO 01/87834, WO 02/051809, WO 02106245, WO 02/04433, WO 02/076929, WO 02/076947, WO 02/51809, WO 02/083134, WO 02/094799, and WO 03/004027, and Japanese Patent Application No. JP 13226269; (3) melanin-concentrating hormone 2 receptor (MCH2R) agonist/antagonists; (4) serotonin reuptake inhibitors such as fluoxetine, paroxetine, and sertraline, and those disclosed in U.S. patent application Ser. No. 6,365,633, and PCT Patent Application Nos. WO 01/27060 and WO 01/162341; (5) melanocortin agonists, such as Melanotan II or those described in WO 99/64002 and WO 00174679; (6) other Mc4r (melanocortin 4 receptor) agonists, such as CHIR86036 (Chiron), ME-10142, and ME-10145 (Melacure), and those disclosed in PCT Application Nos. WO 01/991752, WO 01/74844, WO 02/12166, WO 02/11715, and WO 02112178; (7) 5HT-2 agonists; (8) 5HT2C (serotonin receptor 2C) agonists, such as BVT933, DPCA37215, WAY161503, R-1065, IK264, and PNU 22394, and those disclosed in U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457; (9) galanin antagonists; (10) CCK agonists; (11) CCK-A (cholecystokinin-A) agonists, such as AR-R 15849, GI 181771, JMV-180, A-71378, A-71623 and SR146131, and those discribed in U.S. Pat. No. 5,739,106; (12) GLP-1 (glucagon like peptide 1 agonists; (13) corticotropin-releasing hormone agonists; (14) histamine receptor-3 (H3) modulators; (15) histamine receptor-3 (H3) antagonists/inverse agonists, such as hioperamide, 3(1H-imidazol-4-yl)propyl N-(4-pentenyl)carbamate, clobenpropit, iodophenpropit, imoproxifan, GT2394 (Gliatech), A 331440, and those described in PCI Application No. WO 02/15905, and O-[3-(1H-imidazol4-yl) propanol]-carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm.(Weinheim) 334: 45-52 (2001)), substituted N-phenylcarbamates (Reidemeister, S. et al., Pharmazie, 55:83-6 (2000)), and proxifan derivatives (Sasse, A. et al., J. Med. Chem. 43:333543 (2000)); (16) 11β-hydroxy steroid dehydrogenase-1 inhibitors (11β-HSD-1), such as BVT 3498, BVT 2733, and those compounds disclosed in WO 01/90091, WO 01/90090, WO 01/90092; (17) PDE (phosphodiesterase) inhibitors, such as theophylline, pentoxifylline, zaprinast, sildenafil, amrinone, milrinone, cilostamide, rolipram, and cilomilast; (18) phosphodiesterase-3B (PDE3B) inhibitors; (19) NE (norepinephrine) transport inhibitors, such as GW 320659, despiramine, talsupram, and nomifensine; (20) ghrelin receptor antagonists, such as those disclosed in PCT Application Nos. WO 01/87335, and WO 02/08250; (21) leptin, including recombinant human leptin (PEG-OB, Hoffman La Roche) and recombinant methionyl human leptin (Amgen); (22) leptin derivatives, such as those disclosed in U.S. Pat. Nos. 5,552,524, 5,552,523, 5,552,522, 5,521,283, and PCI International Publication Nos. WO 96/23513, WO 96/23514, WO 96/23515, WO 96/23516, WO 96/23517, WO 96/23518, WO 96/23519, and WO 96/23520; (23) BRS3 (bombesin receptor subtype 3) agonists; (24) CNTF (Ciliary neurotrophic factors), such as GI-181771 (Glaxo-SmithKline), SR146131 (Sanofi Synthelabo), butabindide, PD170,292, and PD 149164 (Pfizer); (25) CNTF derivatives, such as axokine (Regeneron), and those disclosed in PCT Application Nos. WO 94/09134, WO 98/22128, and WO 99/43813; (26) monoamine reuptake inhibitors, such as sibutramine (Meridia®/Reductil®), and those disclosed in U.S. Pat. Nos. 4,746,680, 4,806,570, and 5,436,272, and U.S. Patent Publication No. 2002/0006964, WO 01127068, and WO 01/62341; (27) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), retinoic acid, and those disclosed in PCT Patent Application No. WO 99/00123; (28) thyroid hormone β agonists, such as KB-2611 (KaroBioBMS), and those disclosed in PCT Application No. WO 02/15845, and Japanese Patent Application No. JP 2000256190; (29) FAS (fatty acid synthase) inhibitors, such as Cerulenin and C75; (30) DGAT1 (diacylglycerol acyltransferase 1) inhibitors; (31) DGAT2 (diacylglycerol acyltransferase 2) inhibitors; (32) ACC2 (acetyl-CoA carboxylase-2) inhibitors; (33) glucocorticoid antagonists; (34) acyl-estrogens, such as oleoyl-estrone, disclosed in del Mar-Grasa, M. et al., Obesity Research, 9:202-9 (2001); (35) dipeptidyl peptidase IV (DP-IV) inhibitors, such as isoleucine thiazolidide; NVP-DPP728; P32/98; LAF 237, TSL 225, valine pyrrolidide, TMC-2A/2B/2C, CD-26 inhibitors, FE 999011, P9310/K364, VIP 0177, DPP4, SDZ 274444; and the compounds disclosed in WO 03/004498; WO 03/004496; EP 1 258 476; WO 02/083128; WO 02/062764; WO 03/000250; WO 03/002530; WO 03/002531; WO 03/002553; WO 03/002593; WO 03/000180; and WO 03/000181; (36) fatty acid transporter inhibitors; (37) dicarboxylate transporter inhibitors; (38) glucose transporter inhibitors; (39) phosphate transporter inhibitors; (40) Topiramate (Topimax®); (41) 5HT (serotonin) transporter inhibitors, such as paroxetine, fluoxetine, fluvoxamine, sertraline, and imipramine; (42) opioid antagonists, such as nalmefene (Revex®), 3-methoxynaltrexone, naloxone, and naltrexone; and those disclosed in WO 00/21509; (43) Mc3r (melanocortin 3 receptor) agonists; (44) phytopharm compound 57 (CP 644,673); (45) FAS (fatty acid synthase) inhibitors, such as Cerulenin and C75; (46) SCD-1 (stearoyl-CoA desaturase-1) inhibitors; and the like; (47) aminorex; (48) amphechloral; (49) amphetamine; (50) benzphetamine; (51) chlorphentermine; (52) clobenzorex; (53) cloforex; (54) clominorex; (55) clortermine; (56) cyclexedrine; (57) dextroamphetamine; (58) diethylpropion; (59) diphemethoxidine, (60) N-ethylamphetamine; (61) fenbutrazate; (62) fenisorex; (63) fenproporex; (64) fludorex; (65) fluminorex; (66) furfurylmethylamphetamine; (67) levamfetamine; (68) levophacetoperane; (69) mazindol; (70) mefenorex; (71) metamfepramone; (72) methamphetamine; norpseudoephedrine; (73) pentorex; (74) phendimetrazine; (75) phenmetrazine; (76) phenylpropanolamine; (77) picilorex; and (78) zonisamide; and the like;

(s) lipid lowering agents such as (1) CETP inhibitors such as JTT 705, torcetrapib, CP 532,632, BAY63-2149, SC 591, SC 795, and the like; (2) squalene synthetase inhibitors; (3) FXR receptor modulators such as GW 4064, SR 103912, and the like; (4) LXR receptor such as GW 3965, T9013137, and XTCO179628, and the like; (5) lipoprotein synthesis inhibitors such as niacin; (6) renin angiotensin system inhibitors; (7) PPAR δ partial agonists; (8) bile acid reabsorption inhibitors, such as BARI 1453, SC435, PHA384640, S8921, AZD7706, and the like; (9) triglyceride synthesis inhibitors; (10) microsomal triglyceride transport (MTTP) inhibitors, such as inplitapide, LAB687, and CP346086, and the like; (11) transcription modulators; (12) squalene epoxidase inhibitors; (13) low density lipoprotein (LDL) receptor inducers; (14) platelet aggregation inhibitors; (15) 5-LO or FLAP inhibitors; and (16) niacin receptor agonists;

(t) anti-diabetic agents such as (1) meglitinides such as repaglinide, and nateglinide, and the like; (2) alpha-amylase inhibitors such as tendamistat, trestatin, and A1-3688, and the like; (3) insulin secreatagogues such as linogliride; and A-4166, and the like; (4) fatty acid oxidation inhibitors, such as clomoxir, and etomoxir, and the like; (5) A2 antagonists, such as midaglizole; isaglidole; deriglidole; idazoxan; earoxan; and fluparoxan, and the like; (6) non-thiazolidinediones such as JT-501, and farglitazar (GW-2570/GI-262579), and the like; (7) PPARα/γdual agonists such as CLX-0940, GW-1536, GW1929, GW-2433, KRP-297, L-796449, LR-90, SB 219994, and MK-767, and the like; (8) other insulin sensitizing drugs; and (9) VPAC2 receptor agonists; and (u) anti-hypertensive agents such as (1) diuretics, such as thiazides, including chlorthalidone, chlorthiazide, dichlorophenamide, hydroflumethiazide, indapamide, and hydrochlorothiazide; loop diuretics, such as bumetanide, ethacrynic acid, furosemide, and torsemide; potassium sparing agents, such as amiloride, and triamterene; and aldosterone antagonists, such as spironolactone, epirenone, and the like; (2) beta-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil, and the like; (4) angiotensin converting enzyme (ACE) inhibitors such as benazepril; captopril; cilazapril; delapril; enalapril; fosinopril; imidapril; losinopril; moexipril; quinapril; quinaprilat; ramipril; perindopril; perindropril; quanipril; spirapril; tenocapril; trandolapril, and zofenopril, and the like; (5) neutral endopeptidase inhibitors such as omapatrilat, cadoxatril and ecadotril, fosidotril, sampatrilat, AVE7688, ER4030, and the like; (6) endothelin antagonists such as tezosentan, A308165, and YM62899, and the like; (7) vasodilators such as hydralazine, clonidine, minoxidil, and nicotinyl alcohol, and the like; (8) angiotensin II receptor antagonists such as candesartan, eprosartan, irbesartan, losartan, pratosartan, tasosartan, telmisartan, valsartan, and EXP-3137, F16828K, and RNH6270, and the like; (9) α/β adrenergic blockers as nipradilol, arotinolol and amosulalol, and the like; (10) alpha 1 blockers, such as terazosin, urapidil, prazosin, bunazosin, trimazosin, doxazosin, naftopidil, indoramin, WHIP 164, and XEN010, and the like; (11) alpha 2 agonists such as lofexidine, tiamenidine, moxonidine, rilmenidine and guanobenz, and the like; and (12) aldosterone inhibitors, and the like.

Examples of other anti-obesity agents that can be employed in combination with a compound of Formula I are disclosed in "Patent focus on new anti-obesity agents," *Exp. Opin. Ther. Patents*, 10: 819-831 (2000); "Novel anti-obesity drugs," *Exp. Opin. Invest. Drugs*, 9: 1317-1326 (2000); and "Recent advances in feeding suppressing agents: potential therapeutic strategy for the treatment of obesity, *Exp. Opin. Ther. Patents*, 11: 1677-1692 (2001). The role of neuropeptide Y in obesity is discussed in *Exp. Opin. Invest. Drugs*, 9: 1327-1346 (2000). Cannabinoid receptor ligands are discussed in *Exp. Opin. Invest. Drugs*, 9: 1553-1571 (2000). Various pharmacological approaches for the treatment of obesity is discussed in J-A Fernandez-Lopez, *Drugs*: 62: 915-944 (2002); in H. Bays, et al., "Anti-obesity drug development," *Exp. Opin. Invest. Drugs*, 11: 1189-1204 (2002); and in D. Spanswick, et al., "Emerging Anti-obesity Drugs," *Exp. Opin. Emerging Drugs*, 8(1): 217-237 (2003).

Examples of other active ingredients that may be combined with a compound of Formula I for the treatment or prevention of male or female sexual dysfunction, in particular, male erectile dysfunction, either administered separately or in the same pharmaceutical compositions, include, but are not limited to (a) type V cyclic-GMP-specific phosphodiesterase (PDE-V) inhibitors, including sildenafil and (6R, 12aR)-2,3,6,7,12,12a-hexahydro-2-methyl-6-(3,4-methylenedioxyphenyl)-pyrazino[2',1':6,1]pyrido[3,4-b]indole-1,4-dione (IC-351); (b) alpha-adrenergic receptor antagonists, including phentolamine and yohimbine or pharmaceutically acceptable salts thereof; (c) dopamine receptor agonists, such as apomorphine or pharmaceutically acceptable salts thereof; and (d) nitric oxide (NO) donors.

The instant invention also includes administration of a single pharmaceutical dosage formulation which contains both the MC-4R agonist in combination with a second active ingredient, as well as administration of each active agent in its own separate pharmaceutical dosage formulation. Where separate dosage formulations are used, the individual components of the composition can be administered at essentially the same time, i.e., concurrently, or at separately staggered times, i.e. sequentially prior to or subsequent to the administration of the other component of the composition. The instant invention is therefore to be understood to include all such regimes of simultaneous or alternating treatment, and the terms "administration" and "administering" are to be interpreted accordingly.

Administration in these various ways are suitable for the present compositions as long as the beneficial pharmaceutical effect of the combination of the MC-4R agonist and the second active ingredient is realized by the subject at substantially the same time. Such beneficial effect is preferably achieved when the target blood level concentrations of each active ingredient are maintained at substantially the same time. It is preferred that the combination of the MC-4R agonist and the second active ingredient be co-administered concurrently on a once-a-day dosing schedule; however, varying dosing schedules, such as the MC-4R agonist once a day and the second active ingredient once, twice or more times per day, is also encompassed herein. A single oral dosage formulation comprised of both a MC-4R agonist and a second active ingredient is preferred. A single dosage formulation will provide convenience for the subject, which is an important consideration especially for subjects with diabetes or obese subjects who may be in need of multiple medications.

The above combinations include combinations of a composition of the present invention not only with one other active compound, but also with two or more other active compounds. Non-limiting examples include combinations of the compositions of the present invention with one, two or more active compounds selected from lipid-lowering agents, and anti-hypertensive agents. Combinations of the compositions of the present invention with one, two or more active compounds selected from lipid lowering agents, and anti-diabetic agents are useful to treat, control or prevent metabolic syndrome. In particular, compositions comprising an anti-obesity agent, such as a melanocortin-4 receptor agonist, an anti-hypertensive agent, in addition to an anti-diabetic agent and/or a lipid lowering agent will be useful to synergistically treat, control or prevent metabolic syndrome.

The compounds in the combinations of the present invention may be administered separately, therefore the invention also relates to combining separate pharmaceutical compositions into a kit form. The kit, according to this invention, comprises two separate pharmaceutical compositions: a first unit dosage form comprising a prophylactically or therapeutically effective amount of the melanocortin-4 receptor agonist, or a pharmaceutically acceptable salt or ester thereof, and a pharmaceutically acceptable carrier or diluent in a first unit dosage form, and a second unit dosage form comprising a prophylactically or therapeutically effective amount of the second active ingredient or drug, or a pharmaceutically acceptable salt or ester thereof, and a pharmaceutically acceptable carrier or diluent in a second unit dosage form.

In one embodiment, the kit further comprises a container. Such kits are especially suited for the delivery of solid oral forms such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days or time in the treatment schedule in which the dosages can be administered.

Pharmaceutical Compositions

Another aspect of the present invention provides pharmaceutical compositions which comprises a compound of Formula I and a pharmaceutically acceptable carrier. The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Based on their ease of administration, tablets and capsules represent the most advantageous oral dosage unit form in which case solid pharmaceutical carriers are employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Preparation of Compounds of the Invention

The compounds of structural formula I of the present invention can be prepared according to the procedures of the following Schemes and Examples, using appropriate materials and are further exemplified by the following specific examples. Moreover, by utilizing the procedures described in detail in PCT International Application Publications WO 021068387 (6 Sep. 2002) and WO 02/068388 (6 Sep. 2002), and WO 02/067869 (6 Sep. 2002) which are incorporated by reference herein in their entirety, in conjunction with the disclosure contained herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogencarbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless otherwise noted. Mass spectra (MS) were measured by electron-spray ion-mass spectroscopy.

The phrase "standard peptide coupling reaction conditions" means coupling a carboxylic acid with an amine using an acid activating agent such as EDC, DCC, and BOP in an inert solvent such as dichloromethane in the presence of a catalyst such as HOBt. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., *Protective Groups in Organic Synthesis*, John Wiley & Sons, Inc., New York, N.Y., 1991. CBZ and BOC are commonly used protecting groups in organic synthesis, and their removal conditions are known to those skilled in the art. For example, CBZ may be removed by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of CBZ groups can also be achieved by treatment with a solution of hydrogen bromide in acetic acid or by treatment with a mixture of TFA and dimethylsulfide. Removal of BOC protecting groups is carried out with a strong acid, such as trifluoroacetic acid, hydrochloric acid, or hydrogen chloride gas, in a solvent such as methylene chloride, methanol, or ethyl acetate.

Abbreviations used in the Description of the Preparation of the Compounds of the Present Invention
  BOC (boc) t-butyloxycarbonyl
  BOP benzotriazol-1-yloxytris(dimethylamino)phosphonium hexafluorophosphate
  CBZ (Cbz) benzyloxycarbonyl
  DCC 1,3-dicyclohexylcarbodiimide
  DCM methylene chloride
  DEAD diethyl azodicarboxylate
  DIEA diisopropylethylamine
  DMAP 4-dimethylaminopyridine
  DMF N,N-dimethylformamide
  EDC 1-(3-dimethylaminopropyl)3-ethylcarbodiimide HCl
  EtOAc ethyl acetate
  Et ethyl
  g gram
  h hour
  HATU O-(7-azabenzotriazol-1-yl)-1,1,3,3-tetramethyluronium hexafluorophosphate
  HOAt 1-hydroxy-7-azabenzotriazole
  HOBt 1-hydroxybenzotriazole hydrate
  HPLC high performance liquid chromatography
  M molar
  Me methyl
  MeOH methanol
  Ms methanesulfonate
  mg milligram
  mill minute
  mL milliliter
  mmol millimole
  MC-xR melanocortin receptor (x being a number)
  NMM N-methylmorpholine
  NMO 4-methylmorpholine N-oxide
  Pd(dppf)Cl$_2$ [1,1'-Bis(diphenylphosphino)-ferrocene]-dichloropalladium (II) propyl
  Pr benzotriazol-1-yloxytripyrrolidinephosphonium
  PyBOP hexafluorophosphate r.t. room temperature
TEA triethylamine
Tf trifluoromethane sulfonyl
TFA trifluoroacetic acid
THF tetrahydrofuran
v/v volume/volume Reaction Schemes A-Q illustrate methods employed in the synthesis of the compounds of the present invention of structural formula I. All substituents are as defined above unless indicated otherwise.

Reaction Scheme A illustrates a key step in the synthesis of the novel compounds of structural formula I of the present invention. As shown in reaction Scheme A, the reaction of a piperidine derivative of type 1 with a carboxylic acid derivative of formula 2 affords a title compound of structural formula I. The amide bond coupling reaction illustrated in reaction Scheme A is conducted in an appropriate inert solvent such as DMP, DCM or the like and may be performed with a variety of reagents suitable for amide coupling reactions such as HATU, EDC, or benzotriazol-1-yloxytripyrrolidinephosphonium hexafluorophosphate (PyBOP). Preferred conditions for the amide bond coupling reaction shown in reaction Scheme A are known to those skilled in organic synthesis. Such modifications may include, but are not limited to, the use of basic reagents such as triethylamine (TEA), DIEA, or N-methylmorpholine (No), or the addition of an additive such as HOAt or HOBt. Alternatively, 4-substituted piperidines of formula 1 may be treated with an active ester or acid chloride derived from carboxylic acid 2 which also affords compounds of structural formula I. The amide bond coupling shown in reaction Scheme A is usually conducted at a temperature between 0° C. and r.t., occasionally at elevated temperatures, and the coupling reaction is typically conducted for periods of 1 to 24 hours.

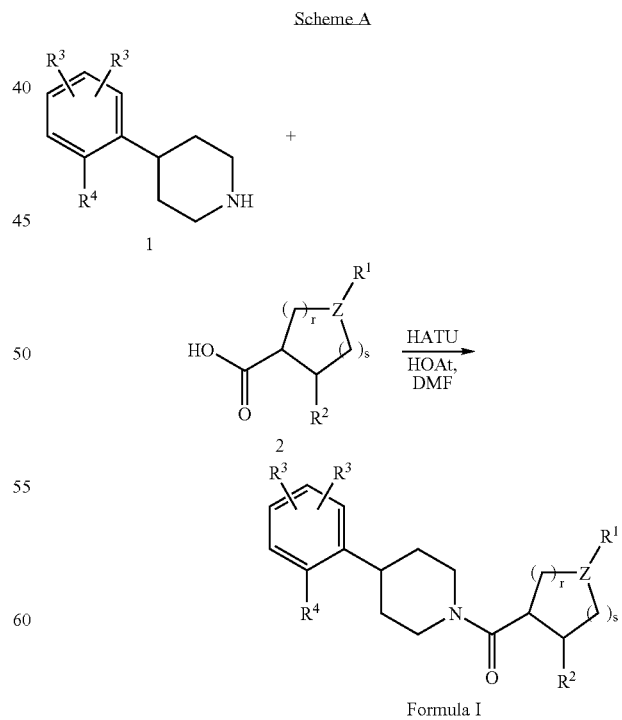

Scheme A

If it is desired to produce a compound of structural formula I wherein Z is a nitrogen and $R^1$ is a hydrogen, the N-BOC protected analogs of structural formula I may be used in the synthesis and deprotected under acidic conditions, for instance using TFA in a solvent like DCM or hydrogen chloride in a solvent such as EtOAc at a temperature between 0° C. and r.t.

When it is desired to prepare compounds of structural formula I wherein Z is a nitrogen and $R^1$ is not a hydrogen, the compounds of general formula I (Z=N, $R^1$=H) may be further modified using the methodology described below in reaction Scheme B. For example, the N-BOC protected compound of structural formula I can be deprotected under acidic conditions for instance by treatment with hydrogen chloride in EtOAc or using TFA in DCM as previously described. The resulting heterocyclic compound of structural formula I (Z=N, $R^1$=H) may then be subjected to one of several alkylation strategies known in organic chemistry to add another $R^1$ group. For instance, compounds (I) (Z=N, $R^1$=H) may be utilized in a reductive amination reaction with a suitable carbonyl containing reagent 3. The reductive amination is achieved by initial formation of an imine between the amine of formula I (Z=N, $R^1$=H) and either an aldehyde or ketone of formula 3. The intermediate imine is then treated with a reducing agent capable of reducing carbon-nitrogen double bonds such as sodium cyanoborohydride or sodium triacetoxyborohydride and an alkylated product of structural formula I is produced. Alternatively, a heterocyclic compound of structural formula (1) (Z=N, $R^1$=H) may be directly alkylated using an alkylating agent such as 4 in a polar aprotic solvent such as DMF. In this reaction, the substituent leaving group, LG, of compound 4 is a leaving group such as a halide, mesylate or triflate, and the product is the compound of structural formula I (Z=N) bearing the $R^1$ substituent.

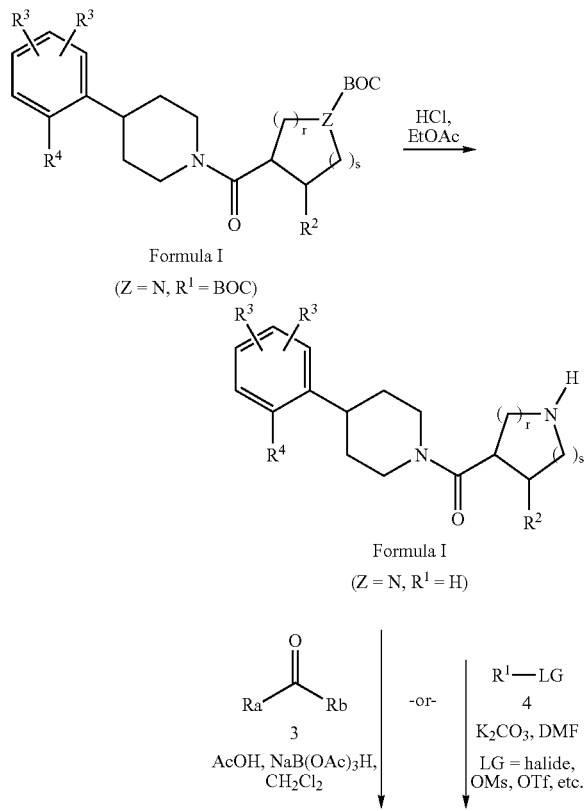

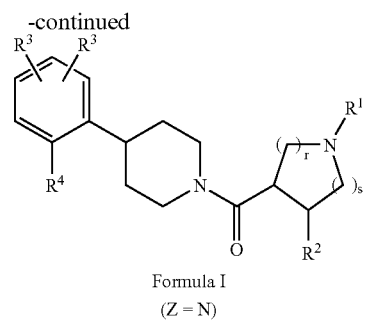

Reaction Schemes C-O illustrate methods for the synthesis of the carboxylic acids of general formula 2 that are utilized in the amide bond coupling reaction shown in reaction Scheme A. These schemes also feature methods for modification or elaboration of compounds of general formula I.

Reaction Scheme C illustrates a preferred method for the synthesis of compounds of general formula 2 wherein Z is a nitrogen, r is 2 and s is 1 such that the resulting heterocycle is a 3-aryl-4-piperidine carboxylic acid derivative 12. The synthesis of 12 begins with a commercially available β-keto ester such as 5. Generally a protecting group interchange of an N-BOC group for the N-benzyl group is performed initially. Thus a β-keto ester of formula 5 is subjected to debenzylation by hydrogenolysis using a palladium-on-carbon catalyst in a solvent system such as 1:1 ethanol-water under a hydrogen atmosphere. The resulting piperidone 6 is then protected as its tert-butyl carbamate using BOC anhydride in the presence of a base and a suitable solvent. For example, this can be accomplished in a two phase mixture of chloroform and aqueous sodium bicarbonate as shown. Incorporation of the 3-aryl substituent is then performed in two steps. First, the β-keto ester group is converted to the corresponding vinyl triflate 8 using trifluoromethanesulfonic anhydride and an organic base like DIEA in an aprotic solvent such as DCM. The resulting vinyl triflate 8 is then subjected to a palladium-catalyzed cross-coupling reaction with an aryl boronic acid (9) using a palladium (II) catalyst such as 1,1,'-bis(diphenylphosphino)-ferrocene]dichloropalladium(II). Preferred conditions for this reaction are the use of a toluene-ethanol-aqueous sodium carbonate solvent system at an elevated temperature, for instance 50-100° C., for a period of 2-24 hours. The resulting aryl-substituted tetrahydropyridine derivative 10 can be reduced to a piperidine such as 11 using a variety of known techniques and the method chosen will determine the stereochemical outcome of the product. For instance, hydrogenation of 10 with a palladium-on-carbon catalyst in a solvent such as ethanol affords cis-3,4-disubstituted piperidines of general formula 11. Alternatively, a dissolving metal reduction using a metal, such as magnesium in methanol, reduces the double bond of 10 and produces a mixture of both cis and trans 3,4-disubstituted piperidines of formula 11. The resulting mixture of cis and trans diastereoisomers may be separated chromatographically or it may be subsequently epimerized to afford the pure trans isomer of 11 by treating the mixture with a base like sodium methoxide in methanol. Finally, hydrolysis of either the cis or trans 3-aryl-4-piperidine carboxylic ester 11 affords either a cis or trans 3-aryl4-piperidine carboxylic acid of general formula 12, corresponding to an acid of general formula 2 wherein r is 2 and s is 1. The cis or trans carboxylic acids of general formula 12 are produced as racemates and either may be resolved to afford enantiomerically pure compounds by methods known in organic synthesis. Preferred methods include resolution by crystallization of diastereoisomeric salts derived from acids 12 and a chiral amine base or the use of chiral stationary phase liquid chromatography columns. Alternatively, the cis or trans carboxylic esters 11 can also be resolved by the use of chiral stationary phase liquid chromatography columns.

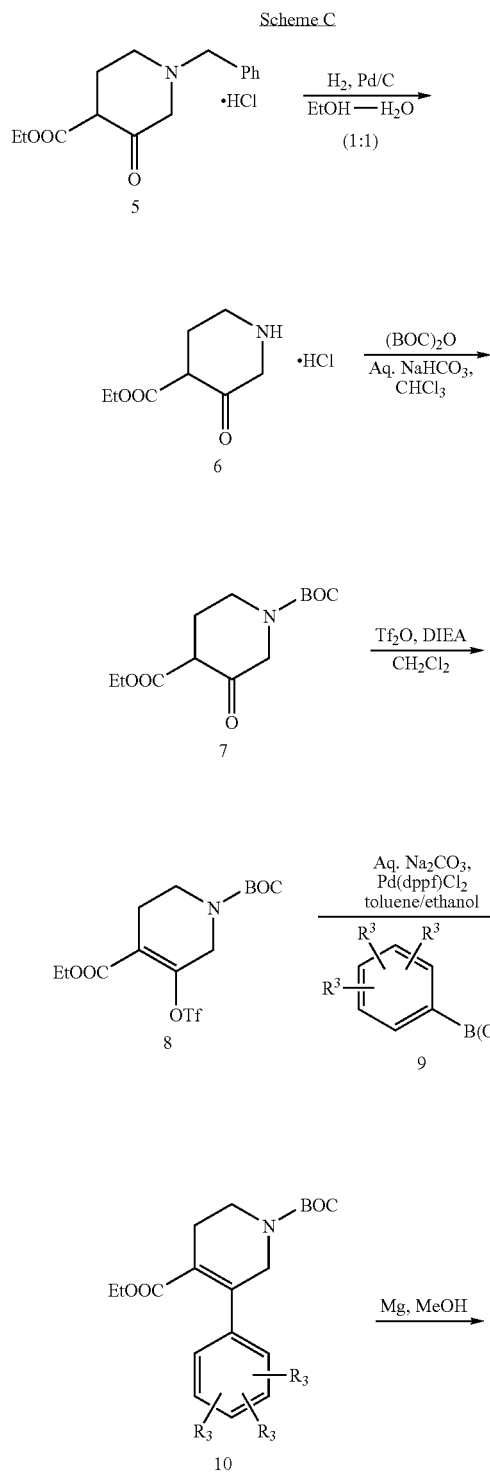

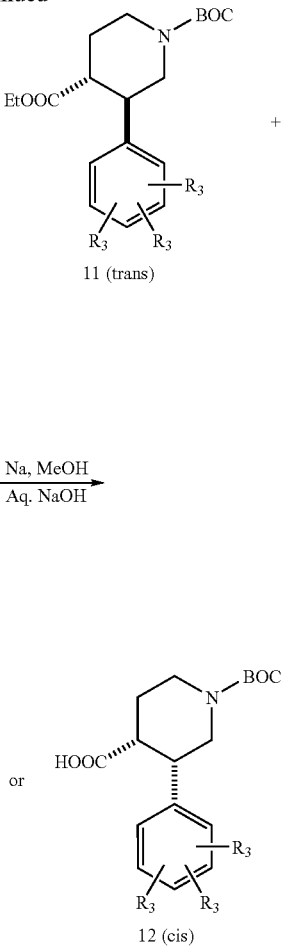

Reaction Scheme D illustrates a preferred method for the synthesis of compounds of general formula 2 wherein Z is a nitrogen, r is 1 and s is 2, such that the resulting heterocycle is a 4-aryl-3-piperidine-carboxylic acid derivative 19. The synthesis of 19 is similar to the synthesis shown in reaction Scheme C, and may begin with either of the commercially available β-keto esters 13 or 14. Conversion of 13 or 14 to the N-BOC-protected piperidine 15 is performed as shown and the resulting β-keto ester is subjected to the two-step arylation protocol previously described in Scheme C to yield 17. Reduction of the double bond of 17 using conditions appropriate for obtaining either cis or trans 18 is followed by ester hydrolysis which affords either a cis or trans 4-aryl-3-piperidine-carboxylic acid of general formula 19 which corresponds to an acid of general formula 2 wherein Z is a nitrogen, r is 1 and s is 2. The cis or trans carboxylic acids of general formula 19 are produced as racemates and either may be resolved to afford enantiomerically pure compounds by methods known in organic synthesis. Preferred methods include resolution by crystallization of diastereoisomeric salts derived from the acids 19 and a chiral amine base or by the use of chiral stationary phase liquid chromatography columns. As before, the cis or trans carboxylic esters 18 can also be resolved by the use of chiral stationary phase liquid chromatography columns.

Scheme D

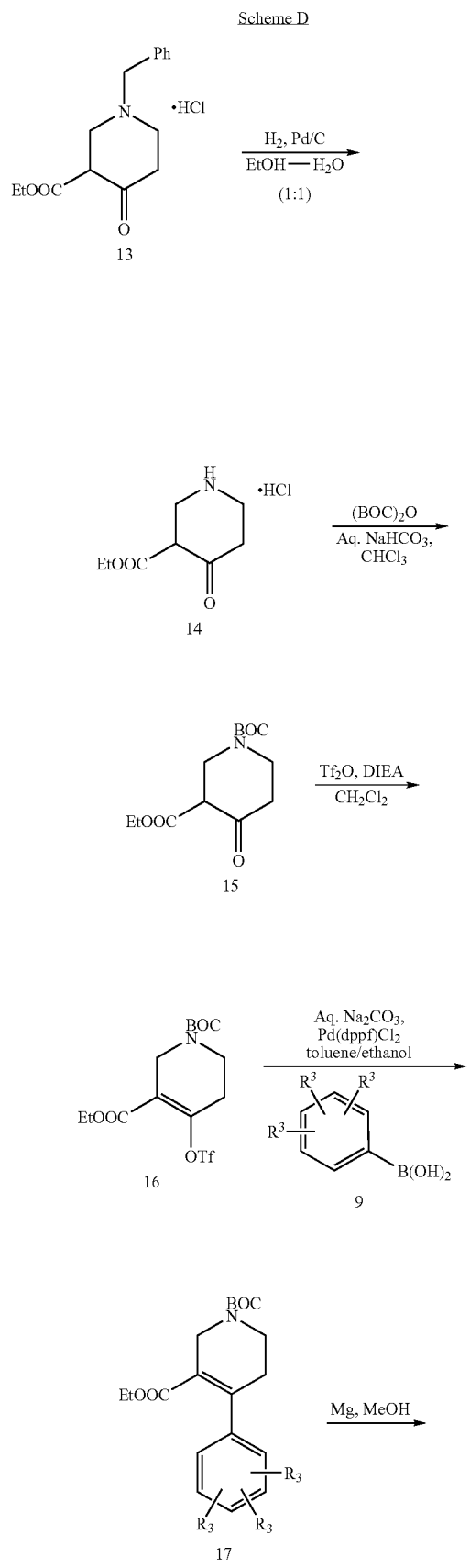

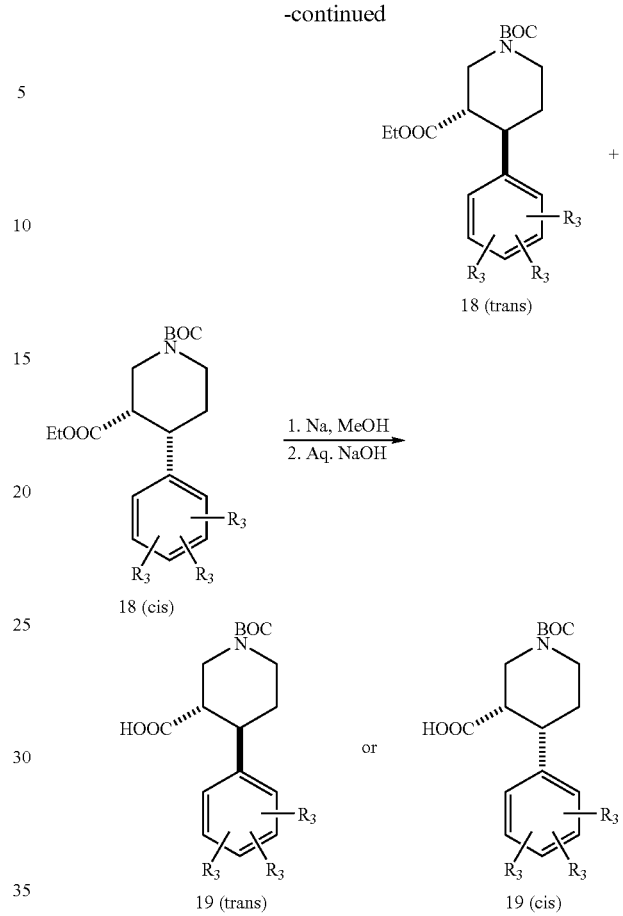

The synthesis of the N-BOC protected carboxylic acids of general formula 12 and 19 illustrated in reaction Schemes C and D are useful for the preparation of title compounds of structural formula I (Z=N) bearing a variety of $R^1$ substituents as noted above. For the synthesis of certain title compounds of structural formula I, for instance when it is desired that Z is nitrogen and $R^1$ is tert-butyl group, it is preferable to incorporate that $R^1$ substituent at an earlier stage of the synthesis. The synthesis of a 1-substituted-3-ketopiperidine-4-carboxylic ester (23) is shown in reaction Scheme E. A primary amine 20 bearing a desired $R^1$ substituent like a tert-butyl group is reacted with ethyl 4-bromobutyrate at elevated temperature in the absence of a solvent to afford the N-substituted ethyl 4-aminobutyrate 21. The amino ester 21 is then alkylated a second time with ethyl bromoacetate in a high boiling inert solvent such as toluene and in the presence of a base such as powdered potassium carbonate. The resulting aminodiester of general formula 22 is then cyclized using an intramolecular Dieckmann reaction to afford a piperidine such as 23. The Dieckmann reaction is performed using a strong base such as potassium tert-butoxide or the like, in an aprotic solvent such as THF at temperatures between r.t. and the boiling point of the solvent. The resulting 1-substituted-3-ketopiperidine-4-carboxylic ester 23 corresponds to a compound of general formula 7 shown in reaction Scheme C, where the BOC group is replaced with the desired $R^1$ substituent. The compounds of general formula 23 may then be converted to compounds of general formula 2 (Z=N) where the $R^1$ substituent replaces the BOC group using the reaction sequence illustrated in reaction Scheme C.

Scheme E

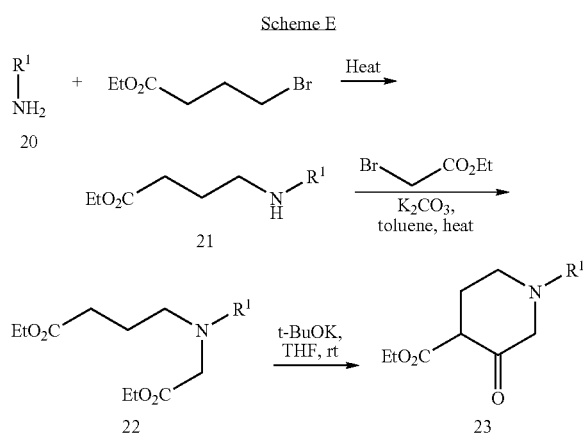

When it is desirable to synthesize a compound of general formula 19 wherein the BOC group is replaced with a substituent group $R^1$, a reaction sequence similar to the one illustrated in reaction Scheme D may be employed starting with a compound of general formula 15, which may be synthesized as shown in reaction Scheme F. An amine 20 bearing the desired $R^1$ substituent is first subjected to a Michael addition with excess ethyl acrylate in the presence of a solvent such as THF or ethanol. The resulting diester 24 is then converted to a 1-substituted4-ketopiperidine-3-carboxylic ester 25 using an intramolecular Dieckmann reaction under conditions similar to those illustrated in reaction Scheme E. The substituted piperidine 25 corresponds to a compound of general formula 15 shown in reaction Scheme D, wherein the BOC group is replaced with the desired $R^1$ substituent. The compounds of general formula 25 may then be converted to compounds of general formula 2 where the $R^1$ substituent replaces the BOC group using the methodology illustrated in reaction Scheme D.

Scheme F

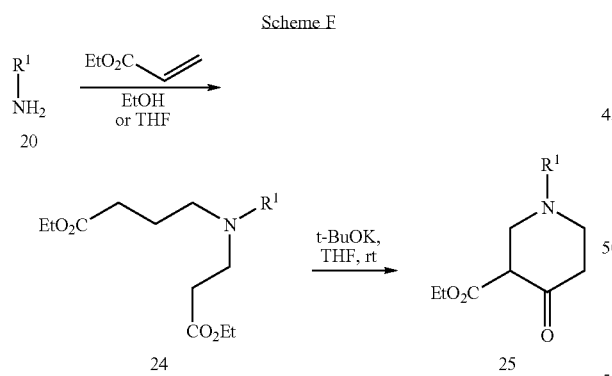

Reaction Scheme G illustrates a strategy for the synthesis of compounds of general formula 2 (Z=N) wherein the values of r and s are selected such that the resulting heterocycle is a 3-aryl-4-pyrrolidine carboxylic acid derivative (31). The preferred method for the synthesis of compounds of general formula 31 involves the azomethine ylid 3+2 cycloaddition reaction of an azomethine ylid precursor of general formula 27 and a substituted cinnamic ester 26. The azomethine cycloaddition reaction of 26 and 27 affords the 3,4-disubstituted pyrrolidine 28, and the stereochemical relationship of the substituents on the newly formed pyrrolidine ring is determined by the stereochemistry of the double bond in the cinnamate ester 26. Thus the trans ester 26 affords a trans 3,4-disubstituted pyrrolidine of formula 28. The corresponding cis cinnamate ester affords a cis 3,4-disubstituted pyrrolidine of general formula 28. Cis or trans 3-arylpyrrolidine-4-carboxylic esters of general formula 28 may be resolved to afford enantiomerically pure compounds using a method such as resolution by crystallization of the diastereoisomeric salts derived from 28 and a chiral carboxylic acid, or directly by the use of chiral stationary phase liquid chromatography columns. Reaction Scheme G illustrates the case where a trans cinnamic ester 26 is converted to a trans 3,4-disubstituted pyrrolidine 28 and its subsequent resolution affords the enantiomerically pure trans pyrrolidine esters 29 and 30. Finally, the esters of general formula 28 (or their pure enantiomers 29 and 30) are hydrolyzed to the corresponding amino acid hydrochlorides of general formula 31 as shown at the bottom of reaction Scheme G.

Amino acids of general formula 31 are zwitterionic. Therefore it is in some cases difficult to achieve efficient separation and purification of these compounds from aqueous reactions or workups. In these cases it is preferred to effect the hydrolysis using a reagent such potassium trimethylsilanolate in diethyl ether. Under these conditions the potassium salt of the carboxylic acid is produced which affords an easily isolated precipitate in ether. The resulting salt is then converted to the corresponding amino acid hydrochloride by treatment with excess hydrogen chloride in a suitable solvent such as EtOAc. Alternatively, esters such as 28 may be converted directly to the amino acid hydrochlorides 31 under acidic hydrolysis conditions. The hydrolysis of the ester 28 is achieved by prolonged reaction with concentrated hydrochloric acid at an elevated temperature. For example, this reaction may be conducted in 8 M hydrochloric acid at reflux overnight. The reaction mixture is then cooled and evaporated in vacuo to afford the amino acid hydrochloride 31. The amino acid hydrochlorides of general formula 31 correspond to an amino acid hydrochloride of general formula 2 (Z=N) wherein both r and s are 1 and may be employed directly in the amide bond coupling step illustrated in reaction Scheme A to produce the compounds of the present invention of structural formula I.

Scheme G

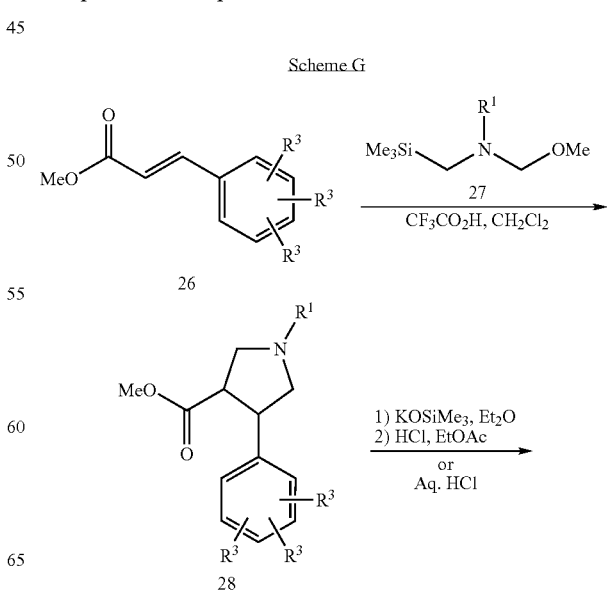

-continued

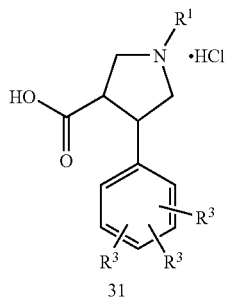
31

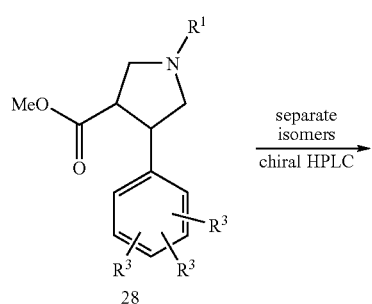
28

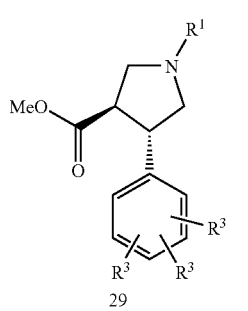
29

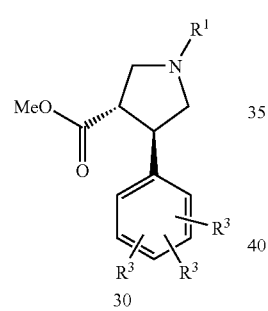
30 tures such as −78° C. and then reacted with a mixed anhydride obtained from acid 32 and an acid chloride like pivaloyl chloride as noted above. The cinnamyl oxazolidinone of general formula 34, which is produced by either of these methods, is then reacted with the azomethine ylid precursor 27 in a manner similar to that described in reaction Scheme G, and the products of the reaction are the substituted pyrrolidines of general formula 35, which may be separated into pyrrolidines of general formula 36 and 37 as shown. The products 36 and 37 are diastereoisomers of each other and may therefore be separated by standard methods such as recrystallization or by liquid chromatography on a stationary phase such as silica gel. As discussed above, if the trans isomer of the cinnamic acid of general formula 32 is employed in the first step of reaction Scheme H, then a trans isomer of the substituted cinnamyl oxazolidinone 34 is produced. If such a trans cinnamyl oxazolidinone is then subjected to the azomethine ylid cycloaddition with an azomethine ylid precursor of formula 27, the products are the diastereoisomeric trans-disubstituted pyrrolidines related to 36 and 37.

Scheme H

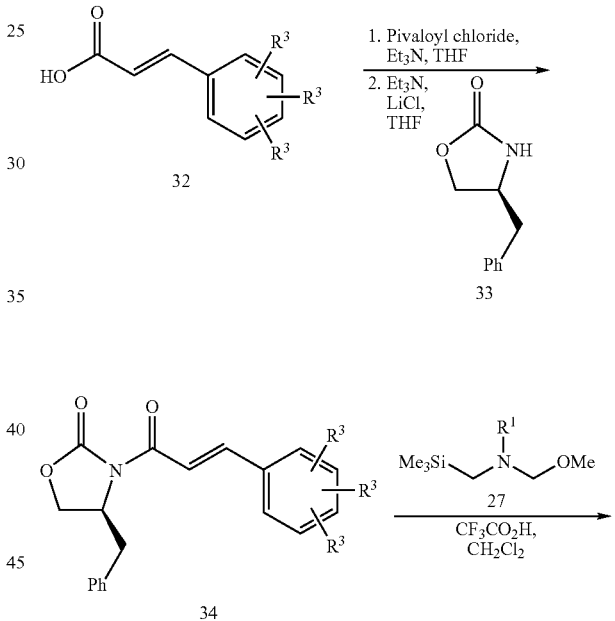

Another preferred method for the synthesis of enantiomerically pure 3-arylpyrrolidine-4-carboxylic acid derivatives is illustrated in reaction Scheme H. In this synthetic method, cinnamyl oxazolidinones of general formula 34 are readily prepared from cinnamic acids and (S)-)4-benzyl-2-oxazolidinone using published methodology (Ho, G.-J.; Mathre, D. J. *J. Org. Chem.* 1995, 60, 2271 and references cited therein). The acylation of chiral auxiliary 33 with cinnamic acids of formula 32 is performed by initial activation of the acid to afford a mixed anhydride. Typically acids of general formula 32 are reacted with an acid chloride such as pivaloyl chloride in the presence of a base such as triethylamine and in a suitable aprotic solvent such as THF. The intermediate cinnamyl-pivaloyl anhydride is converted to the product 34 by reaction with the oxazolidinone 33 in the presence of lithium chloride, an amine base such as triethylamine and in a solvent such as THF, and the reaction is conducted at temperatures between −20° C. and r.t. for periods of 1-24 hours. Alternatively, the oxazolidinone 33 may be deprotonated with a strong base such as n-butyllithium in THF at low tempera-

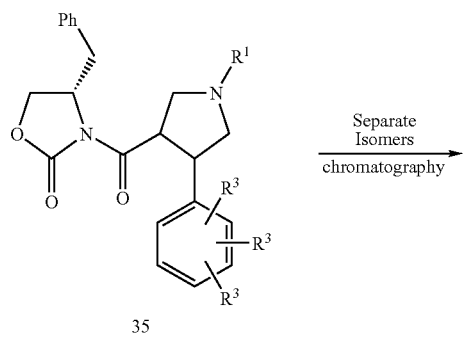
35

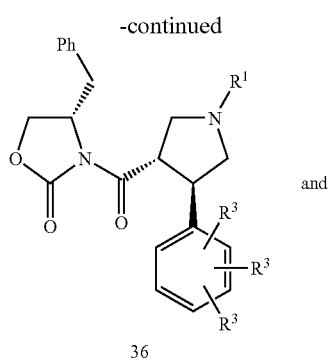

36

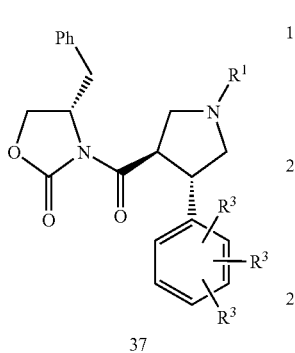

37

The azomethine ylid cycloaddition reactions shown in reaction Schemes G and H are generally conducted with the commercially available azomethine ylid precursor N-(methoxymethyl)-N-(trimethylsilylmethyl)-benzylamine (27, $R^1$=—$CH_2Ph$). When the $R^1$ substituent in the title compounds of structural formula I is chosen to be a group other than benzyl, it is generally preferable to remove the benzyl group from the substituted pyrrolidine compound at this point, and replace it with a more readily removed protecting group such as an N-BOC group. Reaction Scheme I illustrates this process with a generalized 3,4-disubstituted pyrrolidine of formula 35. The preferred method for removal of the N-benzyl group from compounds of general formula 35 will depend upon the identity of the $R^3$ substituents. If these substituents are unaffected by hydrogenation conditions, then the N-benzyl group may be removed by hydrogenolysis using a palladium-on-carbon catalyst in a solvent such as ethanol and in the presence of hydrogen gas or a hydrogen donor such as formic acid. Occasionally it may be preferred that one of the substituents $R^3$ be a halogen or another substituent defined above which would be reactive under hydrogenation conditions. In these cases, the compound of general formula 35 is reacted with 1-chloroethyl chloroformate in an inert solvent such as toluene at temperatures between r.t. and 110° C. (Olafson, R. A. et al. *J. Org. Chem.* 1984, 49, 2081). The toluene is then removed, and the residue is heated in methanol for a period of 15-60 minutes, and the product is the debenzylated pyrrolidine of general formula 38. The resulting pyrrolidine 38 is then protected as its tert-butyl carbamate (329 using BOC anhydride in the presence of a base and a suitable solvent. For example, this can be accomplished in a two phase mixture of chloroform and aqueous sodium bicarbonate as shown in reaction Scheme I.

The oxazolidinone chiral auxilliary is next hydrolyzed from the pyrrolidines of general formula 39 as shown at the bottom of reaction Scheme I. The hydrolysis reaction is accomplished using lithium hydroperoxide generated in situ from lithium hydroxide and 30% aqueous hydrogen peroxide. The reaction is typically conducted in a solvent system such as aqueous THF, and the reaction is performed at temperatures between 0° C. and r.t. for a period of 16 hours. The resulting carboxylic acids of general formula 40 correspond to carboxylic acids of general formula 2 wherein Z is nitrogen, and both r and s are 1. Using the methodology presented in reaction Scheme A, the compounds of general formula 40 may then be converted to the compounds of the present invention of structural formula I (Z=N).

Scheme I

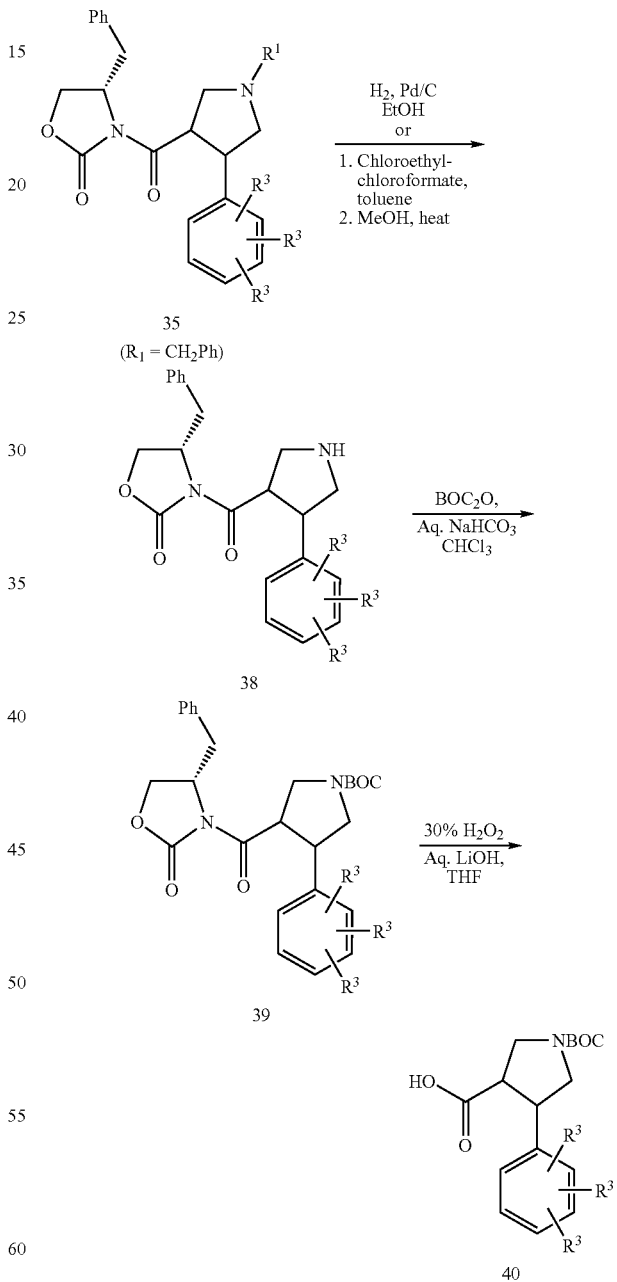

As noted previously in the discussions of reaction Schemes E and F, it may occasionally be preferable to incorporate the $R^1$ substituent into the substituted pyrrolidine of general formula 40 at an earlier stage of the synthesis, for instance when it is desired that $R^1$ be a tert-butyl group. In such cases, it is possible to utilize an azomethine ylid precursor (27) bearing the desired $R^1$ substituent in the cycloaddition reactions illustrated in reaction Schemes G and H. Reaction Scheme J illustrates the preparation of azomethine precursors of formula 27 starting with amines of general formula 20. Reaction of the amine of formula 20 with chloromethyltrimethylsilane at high temperature and in the absence of solvent affords the N-trimethylsilylmethyl-substituted amine of general formula 41. Subsequent reaction of 41 with aqueous formaldehyde in the presence of methanol and a base such as potassium carbonate then affords the generalized ylid precursor 27 which can be utilized in the cycloaddition reactions discussed above.

Scheme J

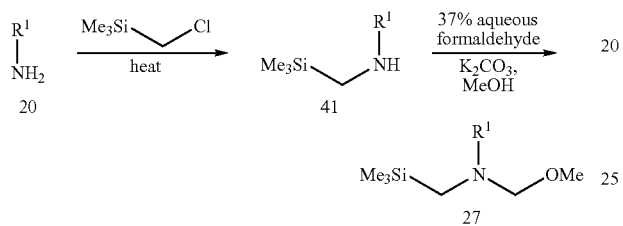

Reaction Schemes K and L illustrate the synthesis of the novel compounds of structural formula I (Z=C) when it is preferred to effect the amide bond coupling step prior to incorporation of the basic substituent $R^1$ as mentioned above. Reaction Scheme K illustrates a preferred method for the synthesis of compounds of structural formula I which employs a piperidine of general formula 1 and a cycloalkanone carboxylic acid of general formula 42 as the partners in the amide bond coupling step. The piperidine of formula 1 and the carboxylic acid of formula 42 are first coupled to afford an amide of general formula 43 using the reagents and conditions described for the generalized amide coupling shown in reaction Scheme A. The $R^1$ substituent ($R^1 = NR^7R^8$) may then be incorporated at the position of the carbonyl group by performing a reductive amination reaction with an amine of general formula 44. Typical conditions for effecting such a reductive amination include preforming an imine 45 from ketone 43 and amine 44 followed by reduction of the intermediate imine with reducing agents such as sodium borohydride, sodium cyanoborohydride or sodium triacetoxyborohydride. Formation of the intermediate imine 45 derived from piperidine 1 and acid 42 may occur spontaneously in solution or it may be promoted with agents such as titanium (IV) isopropoxide in a solvent such as methanol or with anhydrous magnesium sulfate in chloroform. The formation of the imine 45 is generally performed at temperatures between 0° C. and the reflux temperature of the solvent, frequently at r.t. The imine formation step is generally allowed to proceed to completion over a period of several hours to 1 day prior to the reduction step which minimizes the formation of secondary alcohols formed by simple reduction of the keto group in compounds of general formula 43. The intermediate imine 45 may in some cases be isolated and purified, however it is generally preferred to use it directly in the reduction step. The reduction of the imine 45 is typically conducted in an alcoholic solvent such as methanol or ethanol at temperatures between 0° C. and r.t., and the reduction is generally completed in periods of several hours or less.

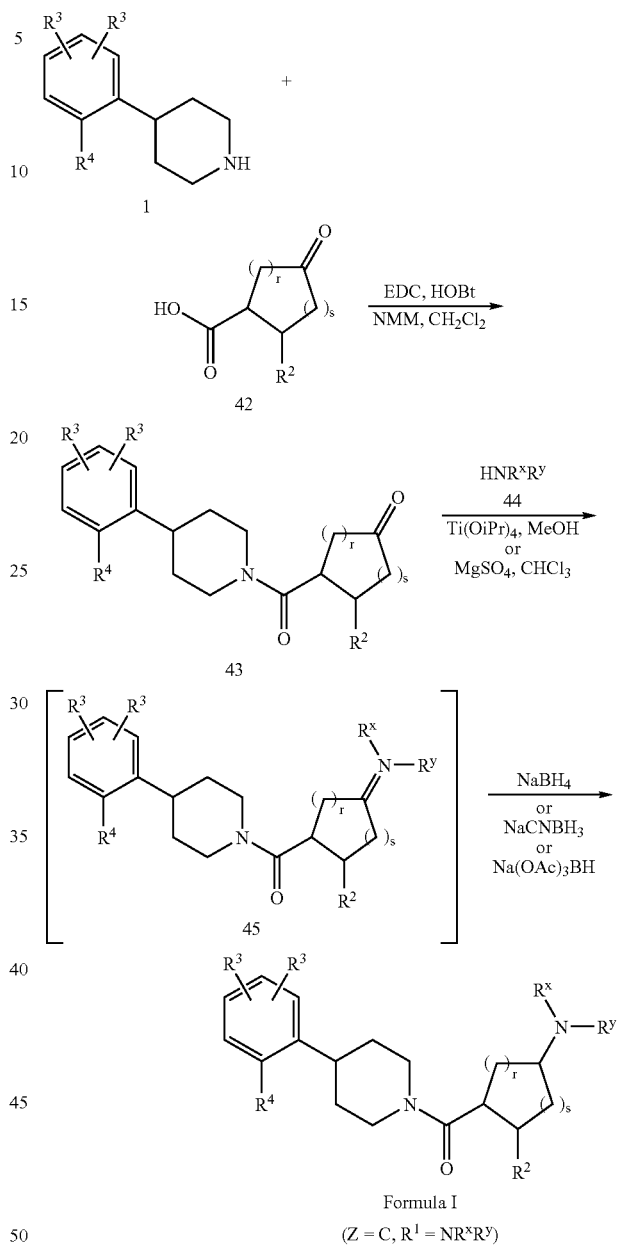

Reaction Scheme L illustrates a preferred method for the synthesis of compounds of structural formula I (Z=C) which employs a piperidine of general formula 1 and a hydroxyl-substituted cycloalkyl carboxylic acid of general formula 46 as the partners in the amide bond coupling step. The amide bond coupling step between piperidine 1 and carboxylic acid 46 is performed first, typically using a carbodiimide reagent like EDC to promote the coupling as described above or by any of the other methods described in the discussion for reaction Scheme A. The hydroxyl-substituted amide 47 which is produced is then further synthetically modified to incorporate the $R^1$ substituent present in the title compounds of structural formula I (Z=C). A variety of methods known to those skilled in organic synthesis may be used to incorporate the $R^1$ substituent. For instance, the hydroxyl group of compounds of general formula 47 may be oxidized using a variety of methods to afford carbonyl compounds of general formula 43. The resulting ketoamides of general formula 43 may then be converted to the title compounds of structural formula I (Z=C) using the reductive amination method described in reaction Scheme K.

Occasionally, it may be preferable to utilize hydroxyl-substituted compounds of general formula 47 in a Fukuyama-Mitsunobu reaction (Fukuyama, T.; Cheung, M.; Jow, C.-K.; Hidai, Y.; Kan, T. *Tetrahedron Lett.* 1997, 33, 5831-4) sequence as shown in reaction Scheme L. In this method for the synthesis of the novel title compounds of structural formula I (Z=C), the intermediate hydroxyl-substituted cycloalkylamide 47 is reacted with a 2,4dinitrobenzenesulfonamide of general formula 48 in the presence of triphenylphosphine and an azodicarboxylate reagent such as DEAD. The reaction is performed in a suitable aprotic solvent such as benzene, toluene or THF, typically at r.t., and the reaction is generally complete in 0.5-3 hours. The product of this reaction is the secondary 2,4-dinitrobenzenesulfonamide of general formula 49, which may then be readily converted to a title compound of structural formula I (Z=C) wherein $R^8$=H. The deprotection of the sulfonamide group is accomplished by reaction of 49 with either a base like n-propylamine in a solvent like DCM or by reaction of 49 with a nucleophilic reagent such as mercaptoacetic acid with triethylamine in DCM. In either case the reaction is typically conducted at r.t., for periods of 5 minutes to one hour. An advantage of the Fukuyama-Mitsunobu reaction sequence is that the stereochemistry of the carbon atom undergoing substitution is cleanly inverted. Thus if the hydroxyl-substituted cycloalkylamide 47 is a single diastereoisomer, then the product 49 will be a single diastereoisomer also. This is in contrast to the reductive amination strategy discussed in reaction Scheme K which generally affords a mixture of epimeric products.

The secondary amine of formula I (Z=C, $R^1$=N(H)$R^7$) shown in reaction Scheme L may then be further synthetically modified using a variety of methods known in organic synthesis to incorporate other embodiments of the $R^8$ substituent. For instance, a compound of structural formula I (Z=C) where $R^8$=H may be subjected to a reductive amination reaction with an appropriate aldehyde or ketone using the conditions described in reaction Scheme K. Alternatively, a compound of structural formula I (Z=C) where $R^8$=H may be directly alkylated with an appropriate alkylating agent using the conditions described in reaction Scheme B.

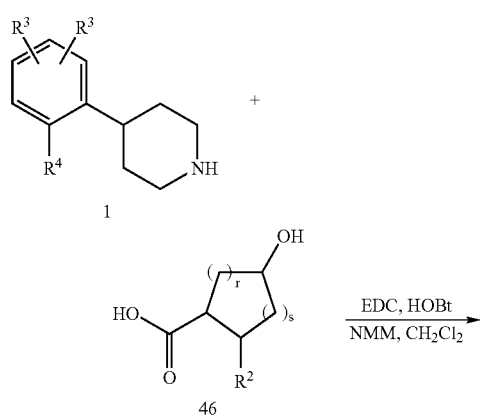

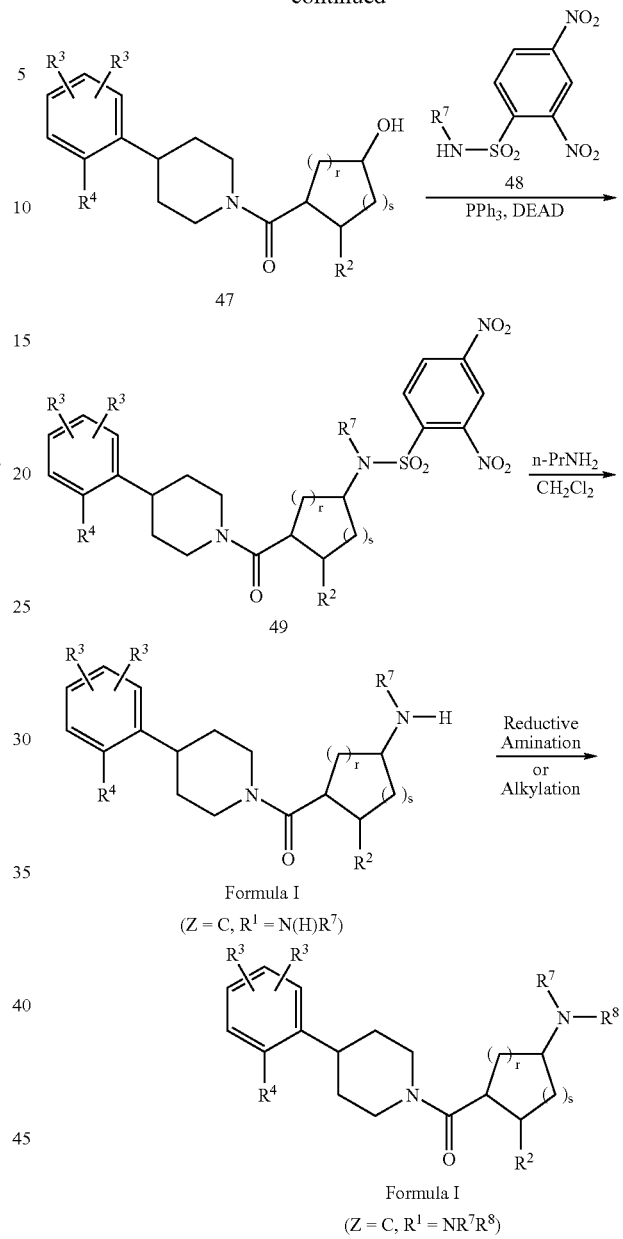

Reaction Scheme M illustrates a preferred method for the synthesis of the cycloalkyl carboxylic acids of general formula 42 when the values of r and s are selected such that the resulting carbocyclic ring is a six-membered ring. In this method a Diels-Alder reaction between an α,β-unsaturated ester of general formula 50 and 2-trimethylsilyloxybutadiene (51 affords a mixture of the two regioisomeric silylenolethers 52 and 53. The silylenolethers 52 and 53 are generally subjected to an hydrolysis reaction using hydrochloric acid in a solvent such as methanol and the two regioisomeric ketones 54 and 55 are then separated by conventional chromatographic methods. The olefin geometry of the starting α,β-unsaturated ester of general formula 50 determines the relative stereochemistry of the two substituents on the six-membered ring. Thus a trans α,β-unsaturated ester 50 affords the trans-disubstituted products 52 and 53 as shown, whereas the corresponding cis isomer of compounds of general formula 50 will afford the corresponding cis isomers of 52 and 53. Once the regioisomeric cyclohexanones of general formulae 54 and 55 are separated, they may then be individually hydrolyzed. For instance, hydrolysis using lithium hydroxide in refluxing THF, affords the carboxylic acids of general formula 42 (r=2, s=1) and 42 (r=1, s=2). The acids of general formula 42 are finally converted to the novel title compounds of structural formula I (Z=C) using the methodology described above in reaction Schemes K and L.

Scheme M

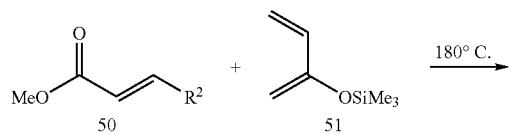

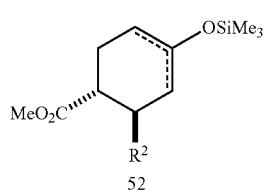

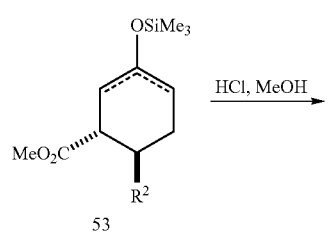

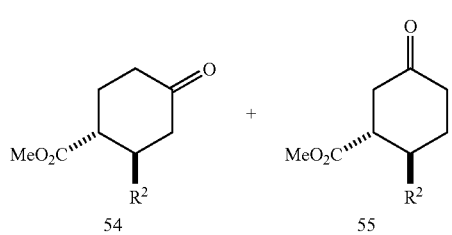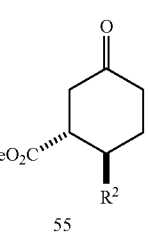

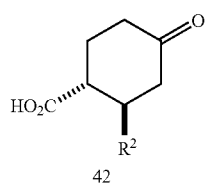 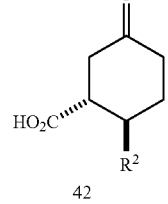

Reaction Scheme N illustrates a preferred method for the synthesis of the cycloalkyl carboxylic acids of general formula 42 when the values of r and s are selected such that the resulting carbocyclic ring is a five-membered ring. In this method an α,β-unsaturated ester of general formula 50 is subjected to a trimethylenemethane cycloaddition reaction (Trost, B. M.; Chan, D. M. T. *J. Am Chem. Soc.* 1979, 101, 6429) to afford a cyclopentane derivative of general formula 57. The cycloaddition is performed by reacting the α,β-unsaturated ester of general formula 50 with 2-[(trimethylsilyl)methyl]-2-propen-1-yl acetate (6) in the presence of a palladium(0) catalyst in a solvent such as THF. A preferred palladium(0) catalyst for the cycloaddition may be generated by mixing palladium acetate and triisopropyl phosphite in the reaction mixture. The cycloaddition reaction is typically conducted at the reflux temperature of the solvent, for instance 65° C., and the reaction is usually completed in periods of 2-8 hours. The olefin geometry of the starting α,β-unsaturated ester of general formula 50 determines the relative stereochemistry of the two substituents on the five-membered ring. Thus a trans α,β-unsaturated ester 50 affords the trans-disubstituted product 57 as shown, whereas the corresponding cis isomer of compounds of general formula 50 affords the corresponding cis-disubstituted isomer of 57. The exocyclic olefin present in compounds of general formula 57 is next oxidatively removed to afford a cyclopentanone derivative of general formula 58. A preferred method for the oxidative cleavage reaction is the two step process shown in reaction Scheme N. The methylene cyclopentane derivative of formula 57 is first oxidized to a 1,2-diol derivative using catalytic osmium tetraoxide in the presence of a stoichiometric reoxidant such as N-methylmorpholine-N-oxide and a solvent system such as acetone-water. The intermediate 1,2-diol which forms is generally not isolated, but is in turn subjected to cleavage with sodium periodate in a solvent system like methanol-water to afford ketones of general formula 58. Both steps in the oxidative cleavage sequence are generally completed during periods of several minutes to a few hours and the reaction steps are typically conducted at low temperatures, for instance between 0° C. and r.t. Alternatively, the oxidative cleavage of olefins of general formula 57 may be accomplished using ozone, or by other methods known in organic synthesis. The cyclopentanones of general formula 58 may then be hydrolyzed, for instance using sodium hydroxide in methanol, to afford the carboxylic acids of general formula 42 (r=1, s=1). The acids of general formula 42 are finally converted to the novel title compounds of structural formula I (Z=C) using the methodology described above in reaction Schemes K and L.

Scheme N

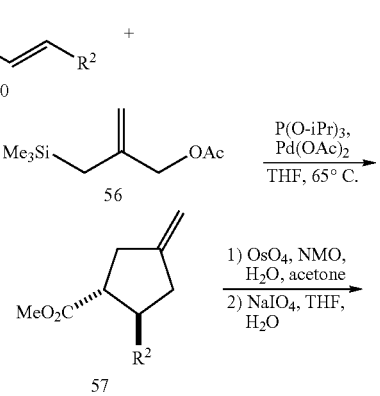

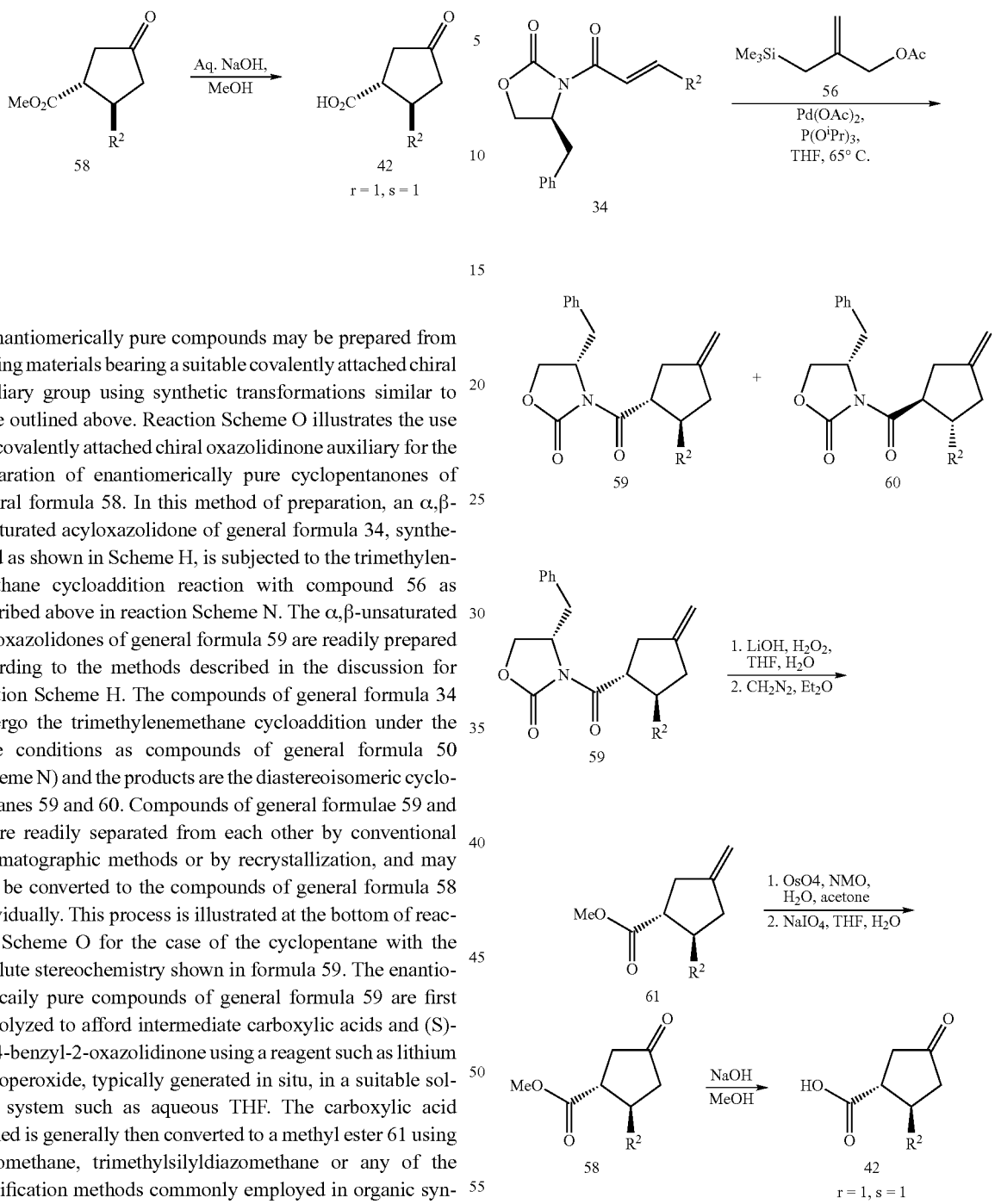

Enantiomerically pure compounds may be prepared from starting materials bearing a suitable covalently attached chiral auxiliary group using synthetic transformations similar to those outlined above. Reaction Scheme O illustrates the use of a covalently attached chiral oxazolidinone auxiliary for the preparation of enantiomerically pure cyclopentanones of general formula 58. In this method of preparation, an α,β-unsaturated acyloxazolidone of general formula 34, synthesized as shown in Scheme H, is subjected to the trimethylenemethane cycloaddition reaction with compound 56 as described above in reaction Scheme N. The α,β-unsaturated acyloxazolidones of general formula 59 are readily prepared according to the methods described in the discussion for reaction Scheme H. The compounds of general formula 34 undergo the trimethylenemethane cycloaddition under the same conditions as compounds of general formula 50 (Scheme N) and the products are the diastereoisomeric cyclopentanes 59 and 60. Compounds of general formulae 59 and 60 are readily separated from each other by conventional chromatographic methods or by recrystallization, and may then be converted to the compounds of general formula 58 individually. This process is illustrated at the bottom of reaction Scheme O for the case of the cyclopentane with the absolute stereochemistry shown in formula 59. The enantiomericaily pure compounds of general formula 59 are first hydrolyzed to afford intermediate carboxylic acids and (S)-(−)-4-benzyl-2-oxazolidinone using a reagent such as lithium hydroperoxide, typically generated in situ, in a suitable solvent system such as aqueous THF. The carboxylic acid formed is generally then converted to a methyl ester 61 using diazomethane, trimethylsilyldiazomethane or any of the esterification methods commonly employed in organic synthesis. The olefin present in the esters of general formula 61 is then subjected to the oxidative cleavage method presented in the discussion of reaction Scheme N to afford enantiomerically pure compounds of general formula 58. The cyclopentanones of general formula 58 may then be hydrolyzed, for instance using sodium hydroxide in methanol, to afford the carboxylic acids of general formula 42 (r=1, s=1). The acids of general formula 42 are finally converted to the novel title compounds of structural formula I (Z=C) using the methodology described above in reaction Schemes K and L.

When it is desired to prepare individual enantiomers of the novel title compounds of structural formula I, it is possible to perform a resolution of the compounds of structural formula I using one of the methods known in the art of organic synthesis. For instance, enantiomerically pure compounds (I) may be prepared by crystallization of diastereoisomeric salts formed from the racemic compounds of structural formula I and an optically active carboxylic acid. The two diastereoisomeric salts are separated from each other by fractional crystallization, then the enantiomerically pure compounds of structural formula I are regenerated by treatment of the purified salts with a base. Alternatively, racemic compounds of structural formula I may be resolved by preparative HPLC using commercially available chiral stationary phase columns. Another strategy for the preparation of enantiomerically pure compounds of structural formula I involves preparing enantiomerically pure compounds of general formula 2 prior to their use in the amide bond forming reaction outlined in reaction Scheme A. Racemic compounds of general formula 2, or intermediates used to prepare compounds of formula 2 as described in the previous reaction Schemes (i.e. acids 12, 19, 31 42 and 46, or esters 11, 18, 28, 54, 55 and 8) may also be resolved using the classical methods previously discussed.

Reaction Scheme P illustrates a preferred method for elaboration of the aryl piperdine substituent to generate compounds of structural formula I whereby $R^4=C(H)(NR^xR^y)$ $CH_2CH_3$. Treatment of enol triflate 62 (prepared as described in: Rohr, M.; Chayer, S.; Garrido, P.; Mann, A.; Taddei, M.; Wermuth, C.-G. Heterocycles 1996, 43, 2131) with bis(pinacolato)diboron reagent in the presence of a suitable palladium (II) catalyst such as (1,1'-Bis(diphenylphosphino)-ferrocene)-dichloropalladium (II) ($Pd(dppf)Cl_2$) and potassium acetate in a polar, inert organic solvent such as methyl sulfoxide at about 80° C. under an inert atmosphere for a period of 6-24 hours provids the vinyl dioxaborolane 63. Borolane 63 can be further reacted with an aryl triflate such as 65, which is prepared from phenol 64 as follows. Phenol 64 can be converted to the triflate using a triflating reagent such as triflic anhydride in the presence of a tertiary amine such as triethylamine and a catalytic amount of DMAP in an inert solvent such as DCM at low temperature. Triflate 65 can be further elaborated by reaction with borolane 63 in the presence of a palladium catalyst such as tetrakis(triphenylphosphine)palladium(0) and aqueous sodium carbonate in a degassed mixture of ethanol and toluene with heating to give the coupled 4-aryl tetrahydropyridine product 66. Reduction of the double bond of intermediate 66 can be effected by treatment with hydrogen at atmospheric pressure and a noble metal catalyst on carbon such as palladium (0) or platinum(IV) oxide in an inert solvent such as ethanol, EtOAc, acetic acid or mixtures thereof to afford the 4-arylpiperidine 67. Removal of the tert-butyloxycarbonyl protecting group by any of the known methods, such as treatment with a protic acid such as hydrogen chloride in an inert solvent such as EtOAc or TFA in DCM, provides the amine salt which can then be used as a coupling partner with acids of type 2 by employing any of the large number of amide bond-forming reagents as described in Scheme A. A second amine-containing substituent can then be incorporated at the position of the carbonyl group of 68 by reductive amination with an amine of general formula 44, as described in Scheme K.

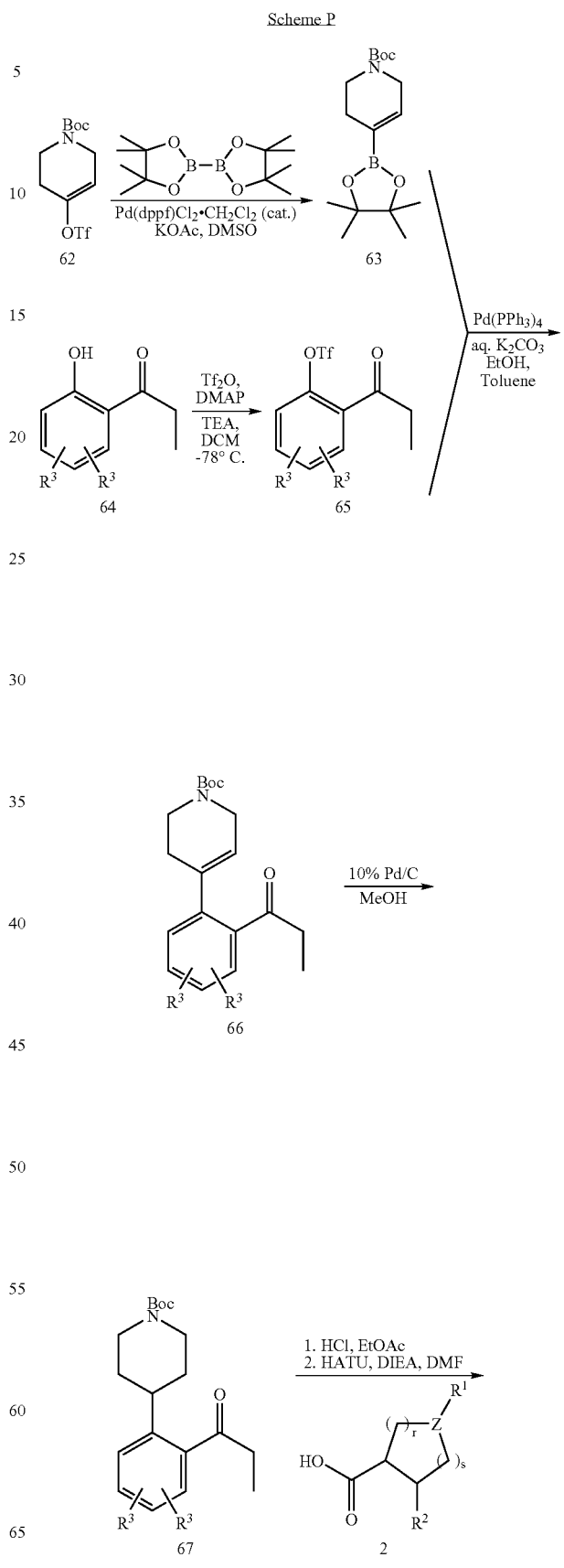

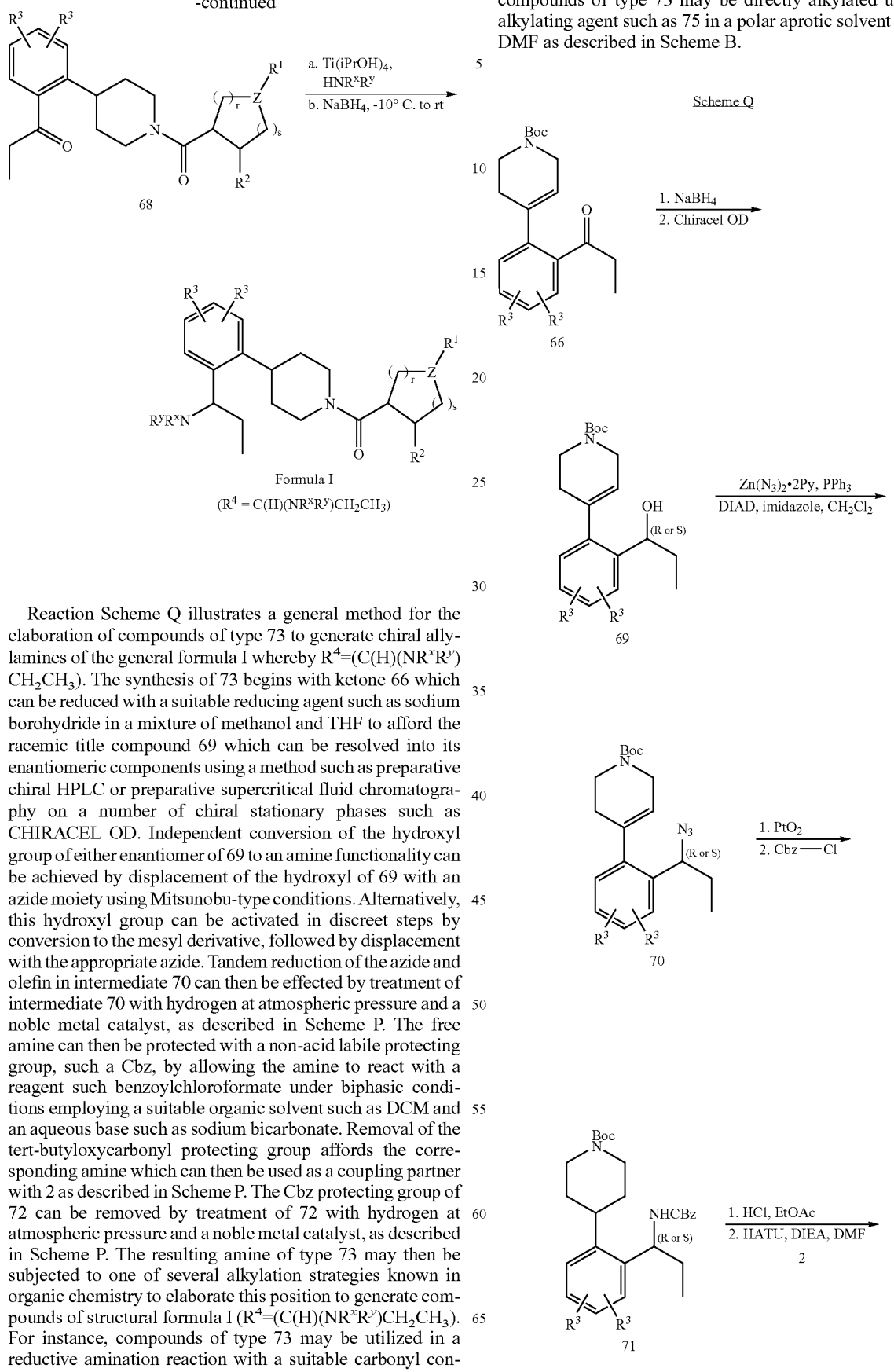

Reaction Scheme Q illustrates a general method for the elaboration of compounds of type 73 to generate chiral allylamines of the general formula I whereby $R^4=(C(H)(NR^xR^y)CH_2CH_3)$. The synthesis of 73 begins with ketone 66 which can be reduced with a suitable reducing agent such as sodium borohydride in a mixture of methanol and THF to afford the racemic title compound 69 which can be resolved into its enantiomeric components using a method such as preparative chiral HPLC or preparative supercritical fluid chromatography on a number of chiral stationary phases such as CHIRACEL OD. Independent conversion of the hydroxyl group of either enantiomer of 69 to an amine functionality can be achieved by displacement of the hydroxyl of 69 with an azide moiety using Mitsunobu-type conditions. Alternatively, this hydroxyl group can be activated in discreet steps by conversion to the mesyl derivative, followed by displacement with the appropriate azide. Tandem reduction of the azide and olefin in intermediate 70 can then be effected by treatment of intermediate 70 with hydrogen at atmospheric pressure and a noble metal catalyst, as described in Scheme P. The free amine can then be protected with a non-acid labile protecting group, such a Cbz, by allowing the amine to react with a reagent such benzoylchloroformate under biphasic conditions employing a suitable organic solvent such as DCM and an aqueous base such as sodium bicarbonate. Removal of the tert-butyloxycarbonyl protecting group affords the corresponding amine which can then be used as a coupling partner with 2 as described in Scheme P. The Cbz protecting group of 72 can be removed by treatment of 72 with hydrogen at atmospheric pressure and a noble metal catalyst, as described in Scheme P. The resulting amine of type 73 may then be subjected to one of several alkylation strategies known in organic chemistry to elaborate this position to generate compounds of structural formula I ($R^4=(C(H)(NR^xR^y)CH_2CH_3)$. For instance, compounds of type 73 may be utilized in a reductive amination reaction with a suitable carbonyl containing reagent 74 as described in Scheme B. Alternatively, compounds of type 73 may be directly alkylated using an alkylating agent such as 75 in a polar aprotic solvent such as DMF as described in Scheme B.

-continued

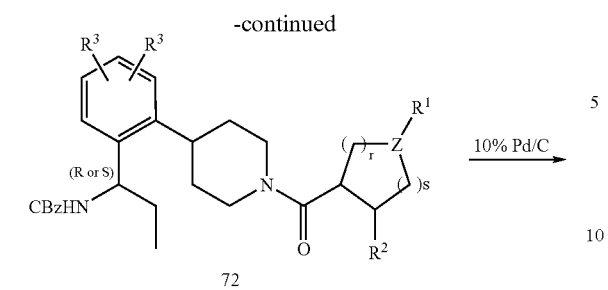
72

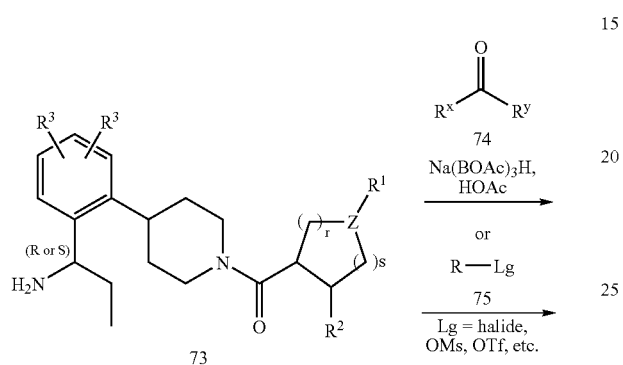
73

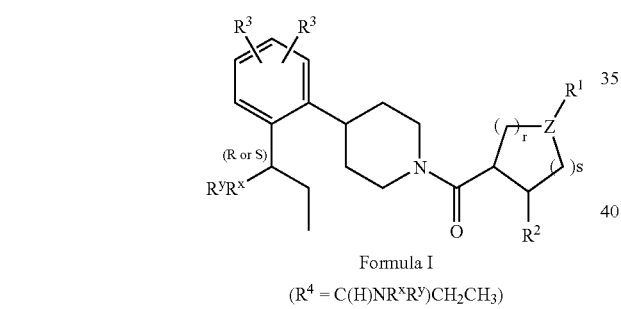
Formula I
(R⁴ = C(H)NRˣRʸ)CH₂CH₃)

If it is desired to further elaborate compounds of type 73 to generate compound of structural formula I whereby $R^4$=C(H)NH(CO)$R^z$CH$_2$CH$_3$, amine 73 can be coupled to acids of type 76 by the methods described in Scheme A (Scheme R).

Scheme R

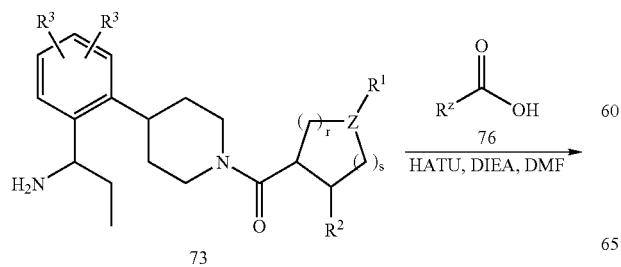

-continued

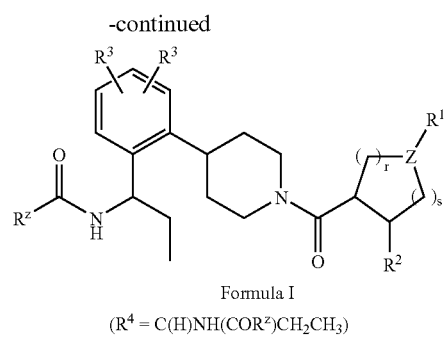
Formula I
(R⁴ = C(H)NH(COR^z)CH₂CH₃)

The following Examples are provided to illustrate the invention and are not to be construed as limiting the scope of the invention in any manner.

Preparation of Intermediates

Scheme 1

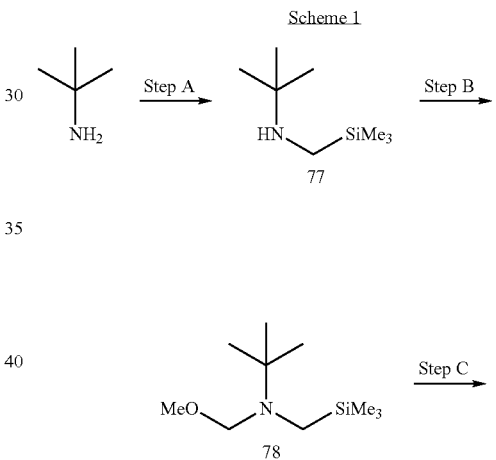

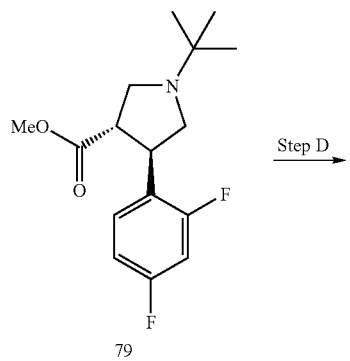
79

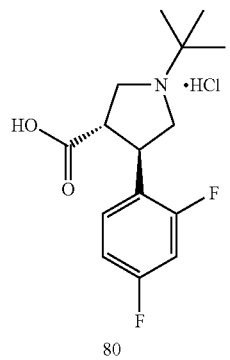

Step A: Preparation of N-tert-butyl-N-(trimethylsilylmethyl)amine (77)

A mixture of tert-butylamine (18.0 mL, 171 mmol) and (chloromethyl)trimethylsilane (7.00 g, 57.1 mmol) was heated in a thick-walled glass tube at 200° C. overnight. After cooling to ambient temperature, the reaction mixture was poured into 1 N NaOH and extracted three times with diethyl ether. The combined organic extracts were washed with brine, dried (MgSO$_4$), and the volatiles evaporated in vacuo. Distillation (atmospheric pressure; ~135° C.) of the residual liquid gave the title compound 77 as a colorless liquid.

Step B: Preparation of N-tert-butyl-N-(methoxymethyl)-N-(trimethylsilylmethyl)amine (78)

N-tert-Butyl-N-(trimethylsilylmethyl)amine 77 (8.47 g, 53.1 mmol) was added dropwise, over approximately 30 min, via a pressure equalizing addition funnel to a stirred solution of aqueous formaldehyde (5.98 mL of a 37 wt. % solution in water, 79.7 mmol) at 0° C. After 45 min, methanol (6.45 mL, 159.3 mmol) was added and the resulting solution was saturated with potassium carbonate. After stirring vigorously for approximately 5 h, the aqueous phase was removed. The organic phase was saturated with potassium carbonate and stirred overnight. The reaction mixture was poured into water and extracted three times with diethyl ether. The combined organic extracts were washed with brine, dried (MgSO$_4$) and the volatiles evaporated in vacuo. Distillation (high vacuum; ~70° C.) of the residual liquid afforded the title compound 78 as a colorless liquid.

Step C: Preparation of methyl (3R,4S)-1-tert-butyl-4-(2,4-difluorophenyl)pyrrolidine-3-carboxylate and methyl (3S,4R)-1-tert-butyl-4-(2,4-difluorophenyl)pyrrolidine-3-carboxylate (79)

TFA (116 µL, 1.51 mmol) was added to a solution of compound 78 (3.07 g, 15.1 mmol) and methyl (2E)-3-(2,4-difluorophenyl)prop-2-enoate (2.99 g, 15.1 mmol) in DCM (60 mL) at ambient temperature. After 18 h, the reaction mixture was poured into saturated aqueous sodium bicarbonate and extracted three times with methlene chloride. The combined organic extracs were washed with brine, dried (Na$_2$SO$_4$) and concentrated in vacuo. Purification of the residue by normal phase medium pressure liquid chromatography on silica gel (gradient elution; 0-9% methanol (containing 10% v/v ammonium hydroxide)/DCM as eluent) gave the title compound 79 as a racemic mixture. The racemic titled compound was resolved into its enantiomeric components using preparative chiral HPLC on CHIRALPAK AD Phase (5% isopropanol/heptanes as eluent) to give in order of elution: methyl (3S,4R)-1-tert-butyl-4-(2,4difluorophenyl)pyrrolidine-3-carboxylate enantiomer as a colorless oil followed by the methyl (3R,4S)-1-tert-butyl-4-(2,4-difluorophenyl)-pyrrolidine-3-carboxylate enantiomer 79 as a colorless oil.

Step D: Preparation of (3S,4R)-1-tert-butyl-4-(2,4-difluorophenyl)pyrrolidine-3-carboxylic acid hydrochloride salt (80)

A mixture of the methyl (3S,4R)-1-tert-butyl-4-(2,4-difluorophenyl)pyrrolidine-3-carboxylate enantiomer 79 (1.37 g, 4.61 mmol) and potassium trimethylsilanolate (0.68 g, 5.30 mmol) in diethyl ether (23 mL) was stirred at r.t. overnight. A saturated solution of hydrogen chloride in EtOAc was then added, the volatiles were evaporated to give 80, which was used without further purification in the preparation of Examples detailed below.

Scheme 2

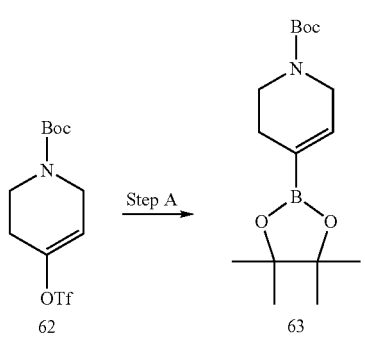

Step A: Preparation of tert-butyl 4-(4,4,5,5-tetramethyl-1,3,2-dioxaborolan-2-yl)-3,6-dihydropyridine-1(2H)-carboxylate (63)

A vigorously stirred suspesion of tert-butyl 4-{[(trifluoromethyl)-sulfonyl]oxy}-3,6-dihydropyridine-1(2H)-carboxylate (62) (1.00 g, 3.02 mmol; prepared as described in Rohr, M.; Chayer, S.; Garrido, P.; Mann, A.; Taddei, M.; Wermuth, C.-G. *Heterocycles* 1996, 43, 2131), bis(pinacolato)diboron (0.844 g, 3.32 mmol), potassium acetate (0.889 g, 9.06 mmol) and (1,1'-bis(diphenylphosphino)-ferrocene] dichloropalladium(II) (0.123 g of a 1:1 complex with DCM, 0.151 mmol) in methyl sulfoxide (20 mL) was degassed via three vacuum/nitrogen ingress cycles and then heated at 80° C. for approximately 15 h. After cooling to ambient temperature, the reaction mixture was filtered through Celite® eluting copiously with EtOAc. The filtrate was poured into water/brine (1:1) and the organic phase separated. The aqueous phase was reextracted three times with EtOAc and the combined organic extracts were washed with brine, dried (MgSO$_4$) and concentrated in vacuo. Purification of the crude residue by flash chromatography on siliga gel (gradient elution: 0%-25% EtOAc/hexanes as eluent) furnished 63 as a white solid.

Scheme 3

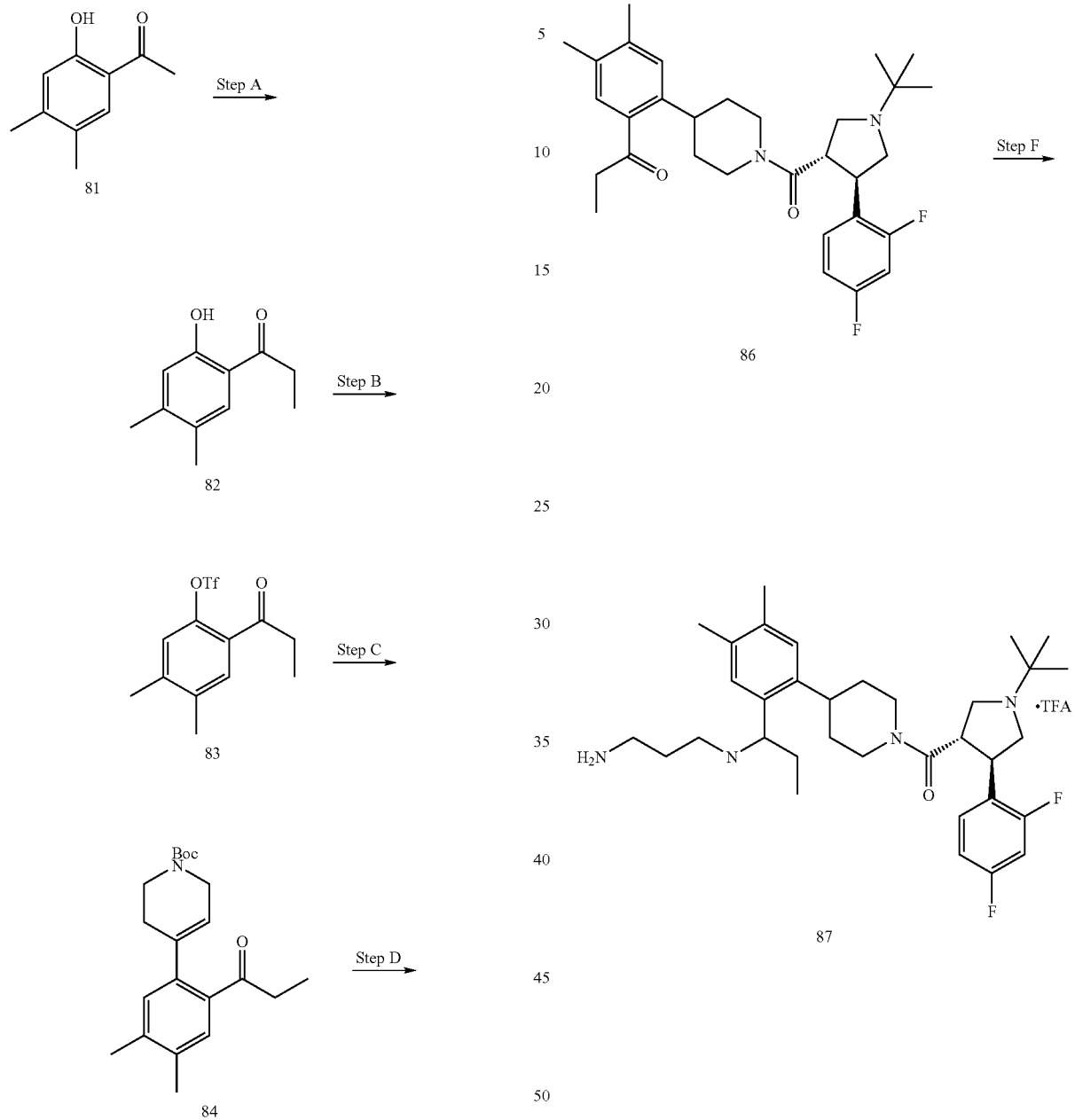

EXAMPLE 87

Step A: Preparation of 1-(2-hydroxy-4,5-dimethylphenyl)propan-1-one (82)

A solution of n-butyllithium (134 mL of a 2.5 M solution in hexanes, 335 mmol) was added dropwise via syringe to a stirred solution of diisopropylamine (51.3 mL, 365 mmol) in THF (100 mL) at −78° C. After approximately 5 min, the reaction mixture was warmed to 0° C. and aged for another 5 min. After recooling to −78° C., a solution of the ketone 81 (25.0 g, 152 mmol) in THF (100 mL) was added dropwise via syringe and the resulting mixture was stirred at −78° C. for approximately 45 min. Iodomethane (47.5 mL, 762 mmol) was added and the solution allowed to warm to ambient temperature and stir overnight. The reaction mixture was quenched with saturated aqueous ammonium chloride, then poured into saturated aqueous ammonium chloride and extracted three times with EtOAc. The combined organic extracts were washed with brine, dried (MgSO$_4$), filtered, and the filtrate concentrated in vacuo. Purification of the crude residue by plug filtration through silica gel eluting with 80:20 hexanes/EtOAc afforded 82 as a pale orange solid.

Step B: Preparation of 4,5-dimethyl-2-propionylphenyl trifluoromethanesulfonate (83)

Triethylamine (23.4 mL, 167 mmol) was added to a mixture of ketone 82 (27.1 g, 152 mmol) and DMAP (1.86 g, 15.2 mmol) in DCM (200 mL) at −78° C., followed by trifluoromethanesulfonic anhydride (28.2 mL, 282.1 mmol) dropwise via syringe. After 2 h, the reaction mixture was poured into ice water, diluted with saturated aqueous ammonium chloride, and extracted three times with EtOAc. The combined organic extracts were washed with brine, dried (MgSO$_4$), filtered, and the filtrate concentrated in vacuo. Purification of the crude residue by plug filtration through silica gel eluting with 80:20 hexanes/EtOAc, followed by recrystallization from ether, gave 83 as a microcrystalline pale orange solid.

Step C: Preparation of tert-butyl 4-(4,5-dimethyl-2-propionylphenyl)-3,6-dihydropyridine-1(2H)-carboxylate (84)

A vigorously stirred solution of triflate 83 (10.5 g, 33.8 mmol), aqueous sodium carbonate (50.8 mL of a 2.0 M solution, 102 mmol), tert-butyl 4(4,4,5,5-tetramethyl-1,3,2-dioxaborolan-2-yl)-3,6-dihydropyridine-1(2H)carboxylate (10.45 g, 33.8 mmol), and tetrakis(triphenylphosphine)palladium(0) (3.91 g, 3.38 mmol) in ethanol/toluene (1:1, 100 mL) was degassed via three vacuum/nitrogen ingress cycles and heated to 75° C. for 30 min. The reaction mixture was poured into ice water and extracted three times with EtOAc. The combined organic extracts were washed with brine, dried (MgSO$_4$), filtered, and the filtrate concentrated in vacuo. Purification of the crude residue by flash chromatography on silica gel (gradient elution; 0%-25% EtOAc/hexanes as eluent) afforded 84 as a colorless oil.

Step D: Preparation of tert-butyl 4-(4,5-dimethyl-2-propionylphenyl)piperidine-1-carboxylate (85)

A mixture of piperidine 84 (2.94 g, 8.5 mmol) and 10% Pd on carbon (144 mg, 0.65 mmol) in ethanol (10 mL) was hydrogenated at atmospheric pressure for approximately 2 h. The resulting mixture was filtered through a short plug of Celite®, eluting copiously with ethanol. The filtrate was concentrated in vacuo and the crude residue purified by flash chromatography on silica gel (gradient elution; 0%-25% EtOAc/hexanes as eluent) to afford 85 as a colorless oil.

Step E: Preparation of 1-[2-(1-{[(3S,4R)-1-tert-butyl-4-(2,4-difluorophenyl)pyrrolidin-3-yl]carbonyl]piperidin-4-yl)-4,5-dimethylphenyl]propan-1-one (86)

A saturated solution of hydrogen chloride in EtOAc (10 mL) was added to a solution of 85 (1.15 g, 3.33 mmol) in DCM (5.0 mL) at ambient temperature. After 30 min the volatiles were evaporated in vacuo. The above residue was resuspended in DCM (10 mL) and to this stirred solution was added DIEA (1.73 mL, 9.9 mmol), (3S,4R)-1-tert-butyl-4-(2,4-difluorophenyl)pyrrolidine-3-carboxylic acid 80 (1.06 g, 3.3 mmol), and HATU (1.39 g, 3.6 mmol). After approximately 18 h, the reaction mixture was poured into water and extracted three times with EtOAc. The combined organic extracts were washed with brine, dried (MgSO$_4$), filtered, and the filtrate concentrated in vacuo. Purification of the crude residue by flash chromatography on silica gel (gradient elution; 0%-20% methanol [containing 10% v/v ammonium hydroxide]/DCM as eluent) afforded 86 as a colorless oil.

Step F: Preparation of N-{1-[2-(1-{[(3S,4R)-1-tert-butyl-4-(2,4-difluorophenyl)pyrrolidin-3-yl]carbonyl}piperidin-4-yl)-4,5-dimethylphenyl]propyl}propane-1,3-diamine trifluoroacetate (87)

To a stirred solution of ketone 86 (50 mg, 0.1 mmol), in THF (5 mL) was added tert-butyl (3-aminopropyl)carbamate (87 µL, 0.5 mmol), and titaniumisopropoxide (73 µL, 0.25 mmol). After 18 h, the reaction mixture was cooled to −10° C. and sodium borohydride was added (9.5 mg, 0.25 mmol) followed by MeOH (100 µL). The reaction mixture was then warmed to ambient temperature. After 2 h, the reaction was quenched with 1 N HCl (100 µL), poured into 2.5 N NaOH, and extracted three times with DCM. The combined organic extracts were washed with brine, dried (MgSO$_4$), filtered, and the filtrate concentrated in vacuo. The crude material was then treated with TFA/DCM (1:1, 10.0 mL) for 30 minutes. The volitales were concentrated in vacuo and the crude residue purified by preparative reversed phase HPLC on YMC Pack Pro C18 (gradient elution; 5-75% acetonitrile/water as eluent, 0.1% TFA modifier) to give 87 as the trifluoroacetate salt.

Following procedures similar to that described above for Example 87, the following compounds were prepared:

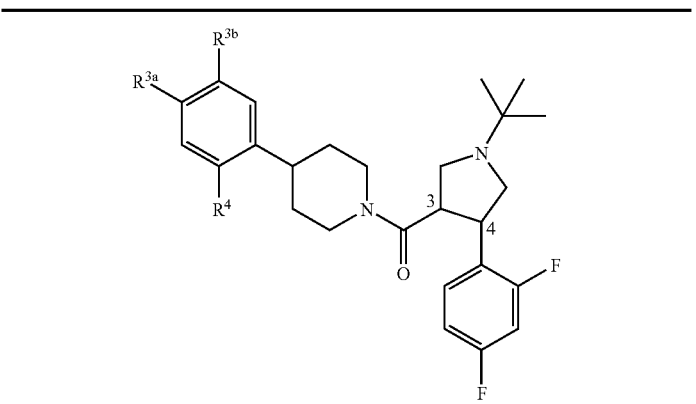
| Ex # | Stereo (3, 4) | R³ᵃ | R³ᵇ | R⁴ | Parent ion (M + H)⁺ |
|---|---|---|---|---|---|
| 88 | (S, R) | Cl | H | Me-CH(NH-)-CH₂-CH₂-NH-C(=O)-Me | 589 |
| 89 | (S, R) | Cl | H | Me-CH(NH-)-CH₂-CH₂-N(Me)₂ | 575 |
| 90 | (S, R) | Cl | H | Me-CH(NH-)-CH₂-CH₂-N(Et)₂ | 603 |
| 91 | (S, R) | Cl | H | Me-CH(NH-)-CH₂-CH₂-NHMe | 561 |
| 92 | (S, R) | Cl | H | Me-CH(NH-)-CH₂-CH₂-NH₂ | 547 |
| 93 | (S, R) | Cl | H | Me-CH(NH-)-CH(Me)-CH₂-N(Et)₂ | 617 |
| 94 | (S, R) | Cl | H | Me-CH(NH-)-CH₂-CH₂-N(CH(Me)₂)₂ | 631 |
| 95 | (S, R) | CH₃ | CH₃ | Et-CH(NH-)-CH₂-CH₂-NHMe | 569 |

-continued
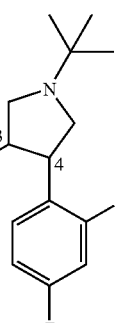
| Ex # | Stereo (3, 4) | R³ᵃ | R³ᵇ | R⁴ | Parent ion (M + H)⁺ |
|---|---|---|---|---|---|
| 96 | (S, R) | CH₃ | CH₃ | 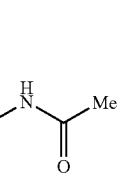 | 611 |
| 97 | (S, R) | CH₃ | CH₃ | 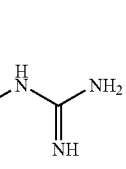 | 597 |
| 98 | (S, R) | CH₃ | CH₃ | 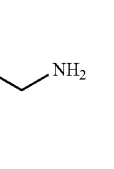 | 597 |
| 99 | (S, R) | CH₃ | CH₃ | 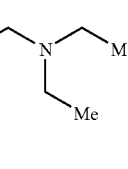 | 555 |
| 100 | (S, R) | CH₃ | CH₃ | 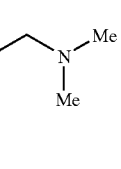 | 625 |
| 101 | (S, R) | CH₃ | CH₃ | | 597 |
| 102 | (S, R) | CH₃ | CH₃ | 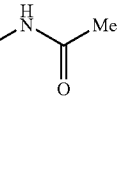 | 639 |

-continued
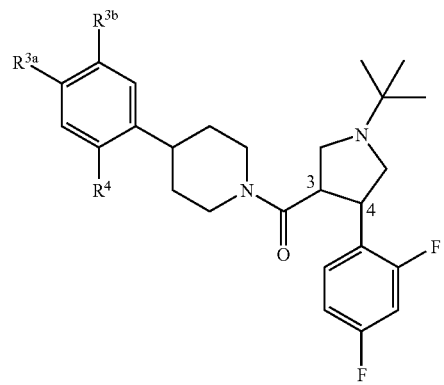
| Ex # | Stereo (3, 4) | $R^{3a}$ | $R^{3b}$ | $R^4$ | Parent ion $(M + H)^+$ |
|---|---|---|---|---|---|
| 103 | (S, R) | $CH_3$ | $CH_3$ | -N(Ac)-CH2CH2-N(Et)2) | 667 |
| 104 | (R, S) | $CH_3$ | $CH_3$ | -NH-CH2CH2-NH2) | 555 |
| 105 | (R, S) | $CH_3$ | $CH_3$ | -NH-CH2CH2-NHMe) | 569 |
| 106 | (R, S) | $CH_3$ | $CH_3$ | -NH-CH2CH2CH2-NH2) | 569 |
| 107 | (R, S) | $CH_3$ | $CH_3$ | -NH-CH2CH2CH2-N(Et)2) | 625 |
| 108 | (R, S) | $CH_3$ | $CH_3$ | -NH-CH2CH2-NHC(O)Me) | 597 |

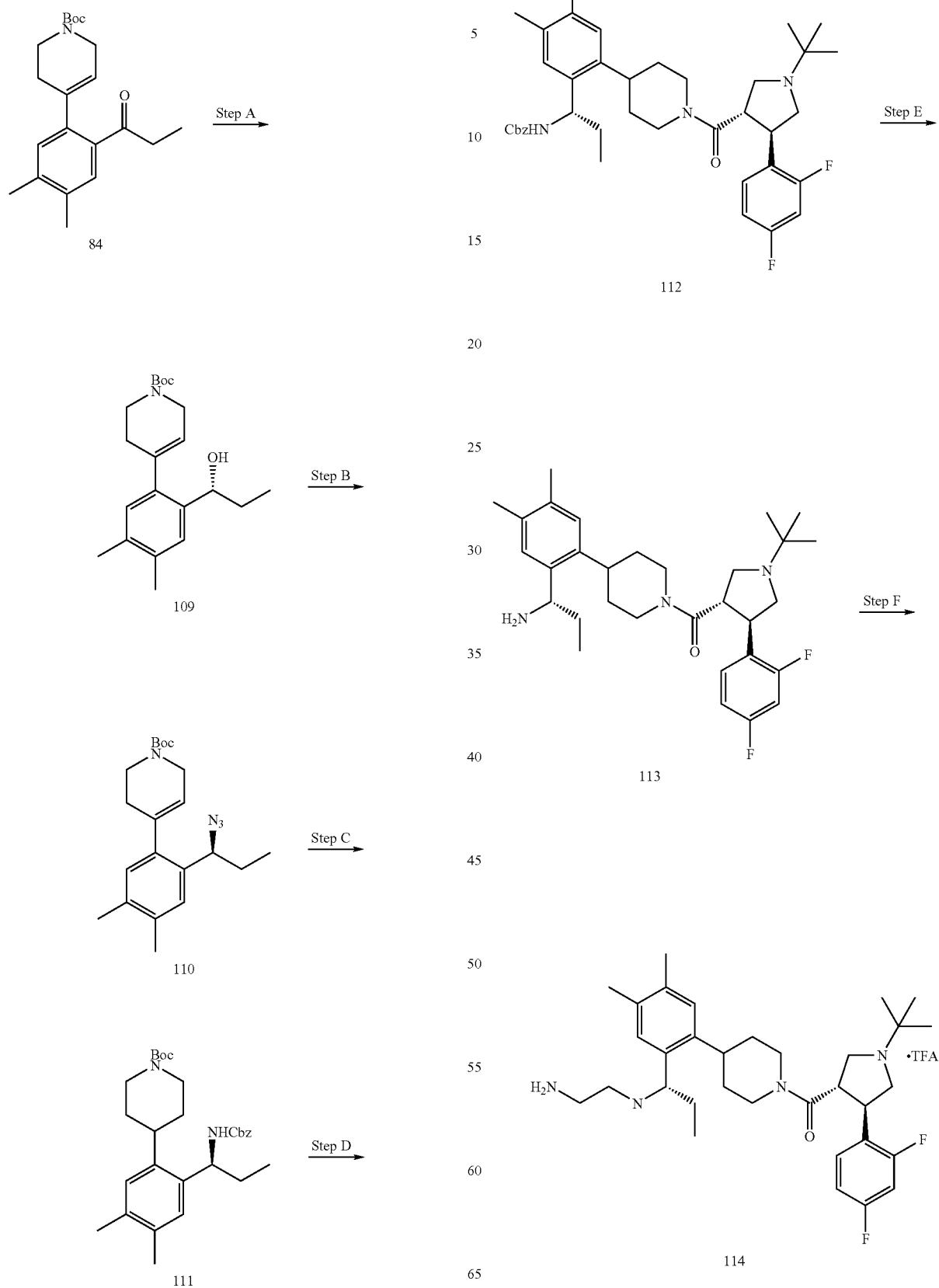

EXAMPLE 114

Step A: Preparation of tert-butyl 4-{2-[(1R)-1-hydroxypropyl]-4,5-dimethylphenyl}-3,6-dihydropyridine-1(2H)-carboxylate (109)

Sodium borohydride (798 mg, 21.1 mmol) was added to a stirred solution of ketone 84 (6.58 g, 19.18 mmol) in THF/methanol (9:1, 100 mL) at −10° C. After 5 h, the reaction was quenched with water, poured into saturated aqueous sodium bicarbonate, and extracted three times with EtOAc. The combined organic extracts were washed with brine, dried (MgSO$_4$), filtered, and the filtrate concentrated in vacuo. Purification of the crude residue by plug filtration through silica gel eluting with 50:50 hexanes/EtOAc afforded racemic 109 as a colorless oil. The racemic title compound was resolved into its enantiomeric components using preparative chiral HPLC on CHIRACEL OD Phase (5% isopropanol/heptane as eluent) to give in order of elution: tert-butyl 4-{2-[(1S)-1-hydroxypropyl]4,5-dimethylphenyl}-3,6-dihydropyridine-1(2H)-carboxylate as a colorless foam followed by tert-butyl 4-{2-[(1R)-1-hydroxypropyl]-4,5-dimethylphenyl}-3,6-dihydropyridine-1(2H)-carboxylate, enantiomer 109, as a colorless foam.

Step B: Preparation of tert-butyl 4-{2-[(1S)-1-hydroxypropyl]-4,5-dimethylphenyl}-3,6-dihydropyridine-1(2H)-carboxylate (110)

Diisopropylazidocarboxylate (2.96 mL, 15.1 mmol) was added dropwise to a stirred mixture of alcohol 109 (1.3 g, 3.76 mmol), Zn(N3)$_2$.2Py (prepared according to the method described by Viaud, M-C; Rollin, P. in *Synthesis*, 1990,130), triphenylphosphine (3.95 g, 15.1 mmol) and imidazole (1.03 g, 15.1 mmol) in DCM (100 mL) at approximately 0° C. After the addition, the resulting mixture was allowed to warm to ambient temperature and stirred vigorously for 18 h. The reaction mixture was filtered through a short column of silica gel eluted with the appropriate volume of DCM to remove excess salts and polar byproducts. The filtrate was concentrated in vacuo and the crude residue purified by flash chromatography on silica gel (gradient elution; 0%-20% EtOAc/hexanes as eluent) to afford azide 110 as a colorless oil.

Step C Preparation of tert-butyl 4-[2-((1S)-1-{[(benzyloxy)carbonyl]amino}propyl)-4,5-dimethylphenyl]piperidine-1-carboxylate (111)

A mixture of azide 110 (1.1 g, 2.97 mmol) and platinum (IV) oxide (49 mg, 222 mmol), in ethanol/glacial acetic acid (1:1, 10.0 mL) was hydrogenated at atmospheric pressure for approximately 8 h. The resulting mixture was filtered through a short column of Celite®, eluting copiously with ethanol. The filtrate was evaporated and the residue was partitioned between DCM and saturated aqueous sodium bicarbonate. The organic layer was separated and the aqueous phase was re-extracted twice with DCM. The combined organic extracts were washed with water, brine, dried (MgSO$_4$), filtered, and the filtrate concentrated in vacuo. The crude residue was resuspended in DCM/saturated aqueous sodium bicarbonate (1:1, 20 mL) and treated with benzoylchloroformate (383 μL, 3.27 mmol) at ambient temperature for approximately 18 h. The reaction mixture was poured into saturated aqueous sodium bicarbonate and extracted three times with EtOAc. The combined organic extracts were washed with brine, dried (MgSO$_4$), filtered, and the filtrate concentrated in vacuo. Purification by flash chromatography on silica gel (gradient elution; 0%-50% EtOAc/hexanes as eluent) afforded 111 as a colorless oil.

Step D: Preparation of benzyl {(1S)-1-[2-(1-{[(3S,4R)-1-tert-butyl-4-(2,4-difluorophenyl)pyrrolidin-3-yl]carbonyl}piperidin-4-yl)-4,5-dimethylphenyl]propyl}carbamate (112

A saturated solution of hydrogen chloride in EtOAc (10.0 mL) was added to a solution of 111 (830 mg, 1.7 mmol) in DCM (5.0 mL) at ambient temperature. After 30 min the volatiles were evaporated in vacuo. The above residue was resuspended in DCM (10.0 mL) and to this stirred solution was added DIEA (886 μL, 5.1 mmol), (3S,4R)-1-tert-butyl4-(2,4-difluorophenyl)pyrrolidine-3-carboxylic acid 80 (542 mg, 1.7 mmol), and HATU (710 mg, 1.87 mmol). After approximately 18 h, the reaction mixture was poured into water and extracted three times with DCM. The combined organic extracts were washed with brine, dried (MgSO$_4$), filtered, and the filtrate concentrated in vacuo. Purification of the crude residue by flash chromatography on silica gel (gradient elution; 0%-10% methanol [containing 10% v/v ammonium hydroxide]/DCM as eluent) afforded 112 as a colorless oil.

Step E: Preparation of {(1S)-1-[2-(1-{[(3S,4R)-1-tert-butyl-4-(2,4difluorophenyl)pyrrolidin-3-yl]carbonyl}piperidin-4-yl)-4,5-dimethylphenyl]propyl}amine (113)

A mixture of amine 112 (910 mg, 1.41 mmol) and 10% Pd on carbon (91 mg of "Degussa type"), in ethanol/glacial acetic acid (1:1, 20 mL) was hydrogenated at atmospheric pressure for approximately 3 h. The resulting mixture was filtered through a short column of Celite®, eluting copiously with ethanol. The filtrate was evaporated and the residue was partitioned between DCM and saturated aqueous sodium bicarbonate. The organic layer was separated and the aqueous phase was re-extracted twice with DCM. The combined organic extracts were washed with water, brine, dried (MgSO$_4$), filtered, and the filtrate concentrated in vacuo to afford 113 as a colorless oil which was used in the next step without further purification.

Step F: Preparation N-{(1S)-1-[2-(1-{[(3S,4R)-1-tert-butyl-4-(2,4-difluorophenyl)pyrrolidin-3-yl]carbonyl}piperidin-4-yl)-4,5-dimethylphenyl]propyl}ethane-1,2-diamine trifluoroacetate (114)

tert-Butyl (2-aminoethyl)carbamate (17.3 mg, 0.1 mmol), sodiumtriacetoxyborohydride (64 mg, 0.3 mmol) and glacial acetic acid (17 μl, 0.3 mmol) were added to a solution of 113 (50 mg, 0.1 mmol) in DCM (1.0 mL) and the resulting mixture allowed to stir at r.t. for 18 h. The reaction mixture was poured into saturated aqueous sodium bicarbonate and extracted three times with EtOAc. The combined organic extracts were washed with brine, dried (MgSO$_4$), filtered, and the filtrate concentrated in vacuo. The crude residue was treated with TFA/DCM (1:1, 2.0 mL) and after 30 min the volatiles were evaporated in vacuo. Purification of the crude residue by preparative reversed phase HPLC on YMC Pack Pro C18 (gradient elution; 0-71% acetonitrile/water as eluent, 0.1% TFA modifier) gave 114 as the trifluoroacetate salt.

Following a procedure similar to that described above for Example 114, the following compounds were prepared:

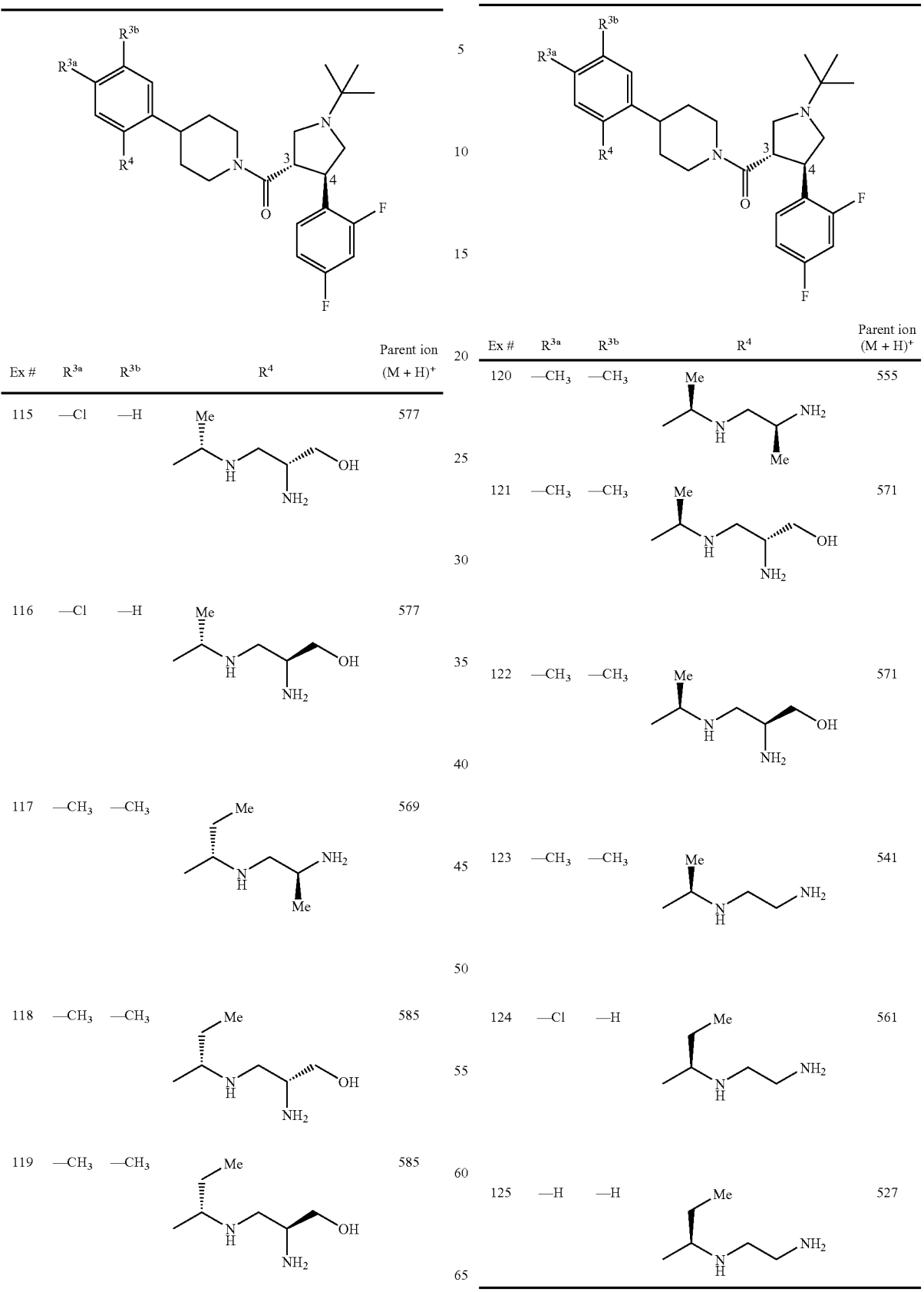
| Ex # | R³ᵃ | R³ᵇ | R⁴ | Parent ion (M + H)⁺ |
|---|---|---|---|---|
| 115 | —Cl | —H | (Me)CH-NH-CH₂-CH(NH₂)-CH₂OH | 577 |
| 116 | —Cl | —H | (Me)CH-NH-CH₂-CH(NH₂)-CH₂OH | 577 |
| 117 | —CH₃ | —CH₃ | (Et,Me)CH-NH-CH₂-CH(NH₂)(Me) | 569 |
| 118 | —CH₃ | —CH₃ | (Et,Me)CH-NH-CH₂-CH(NH₂)-CH₂OH | 585 |
| 119 | —CH₃ | —CH₃ | (Et,Me)CH-NH-CH₂-CH(NH₂)-CH₂OH | 585 |
| 120 | —CH₃ | —CH₃ | (Me)CH-NH-CH₂-CH(NH₂)(Me) | 555 |
| 121 | —CH₃ | —CH₃ | (Me)CH-NH-CH₂-CH(NH₂)-CH₂OH | 571 |
| 122 | —CH₃ | —CH₃ | (Me)CH-NH-CH₂-CH(NH₂)-CH₂OH | 571 |
| 123 | —CH₃ | —CH₃ | (Me)CH-NH-CH₂-CH₂-NH₂ | 541 |
| 124 | —Cl | —H | (Et,Me)CH-NH-CH₂-CH₂-NH₂ | 561 |
| 125 | —H | —H | (Et,Me)CH-NH-CH₂-CH₂-NH₂ | 527 |

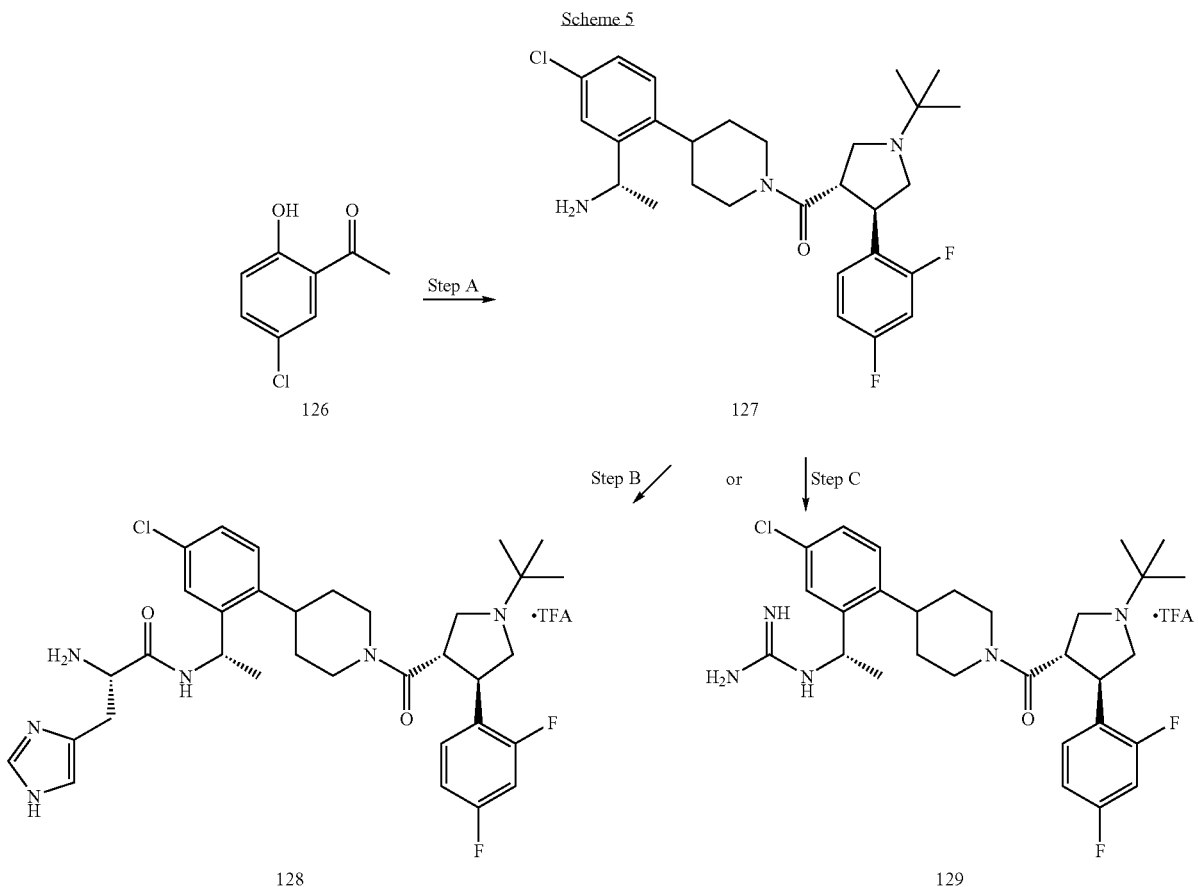

Scheme 5

EXAMPLE 128 AND 129

Step A: Preparation of {(1S)-1-[2-(1-{[(3S,4R)-1-tert-butyl-4-(2,4-difluorophenyl)pyrrolidin-3-yl]carbonyl}piperidin-4-yl)-5-chlorophenyl]ethyl}amine (127)

Compound 127 can be prepared from 1-(5-chloro-2-hydroxyphenyl)ethanone (126) following the procedures described in Schemes 3 and 4.

Step B: Preparation of (N-{(1S)-1-[2-(1-{[(3S,4R)-1-tert-butyl-4-(2,4-difluorophenyl)pyrrolidin-3-yl]carbonyl}piperidin-4yl)-5-chlorophenyl]ethyl}-L-histidinamide trifluoroacetate (128)

DIEA (36.2 μL, 0.208 mmol), N,1-bis(tert-butoxycarbonyl)-L-histidine (29.6 mg, 0.085 mmol), HOAt (14.2 mg, 0.104 mmol) and HATU (39.6 mg, 0.104 mmol) were added to a solution of 127 (325 mg, 0.645 mmol) in DMF. After approximately 18 h, the reaction mixture was poured into water and extracted three times with DCM. The combined organic extracts were washed with brine, dried (MgSO$_4$), filtered, and the filtrate concentrated in vacuo. The crude residue was treated with a saturated solution of HCl in EtOAc for 2 h. The volatiles were evaporated in vacuo and the crude residue purified by preparative reversed phase HPLC on YMC Pack Pro C18 (gradient elution; 0-70% acetonitrile/water as eluent, 0.1 TFA modifier) to give 128 as the trifluoroacetate salt.

Step C: Preparation of N-{(1S)-1-[2-(1-{[(3S,4R)-1-tert-butyl-4-(2,4-difluorophenyl)pyrrolidin-3-yl]carbonyl}piperidin-4-yl)-5-chlorophenyl]ethyl}guanidine trifluoroacetate (129)

Triethylamine (3.6 μL, 0.05 mmol) and di-tert-butyl ({[(trifluoromethyl)sulfonyl]amino}methylylidene)biscarbamate (19.4 mg, 0.05 mmol) (prepared as described in Feichtinger, K.; Zapf, C.; Sings, H. L.; and Goodman, M. *J. Org. Chem.* 1998, 63, 3804) were added to a solution of 127 in DCM (1.0 mL) and the resulting solution allowed to stir at r.t. for 18 h. The reaction mixture was poured into water and extracted three times with DCM. The combined organic extracts were washed with brine, dried (MgSO$_4$), filtered, and the filtrate concentrated in vacuo. The crude material was then treated with TFA/DCM (1:1, 2.0 mL) and after 30 min the volatiles were evaporated in vacuo. Purification of the crude residue by preparative reversed phase HPLC on YMC Pack Pro C18 (gradient elution; 0-70% acetonitrile/water as eluent, 0.1% TFA modifier) gave 129 as the trifluoroacetate salt.

Following a procedure similar to that described above for Examples 128 and 129, the following compounds were prepared:

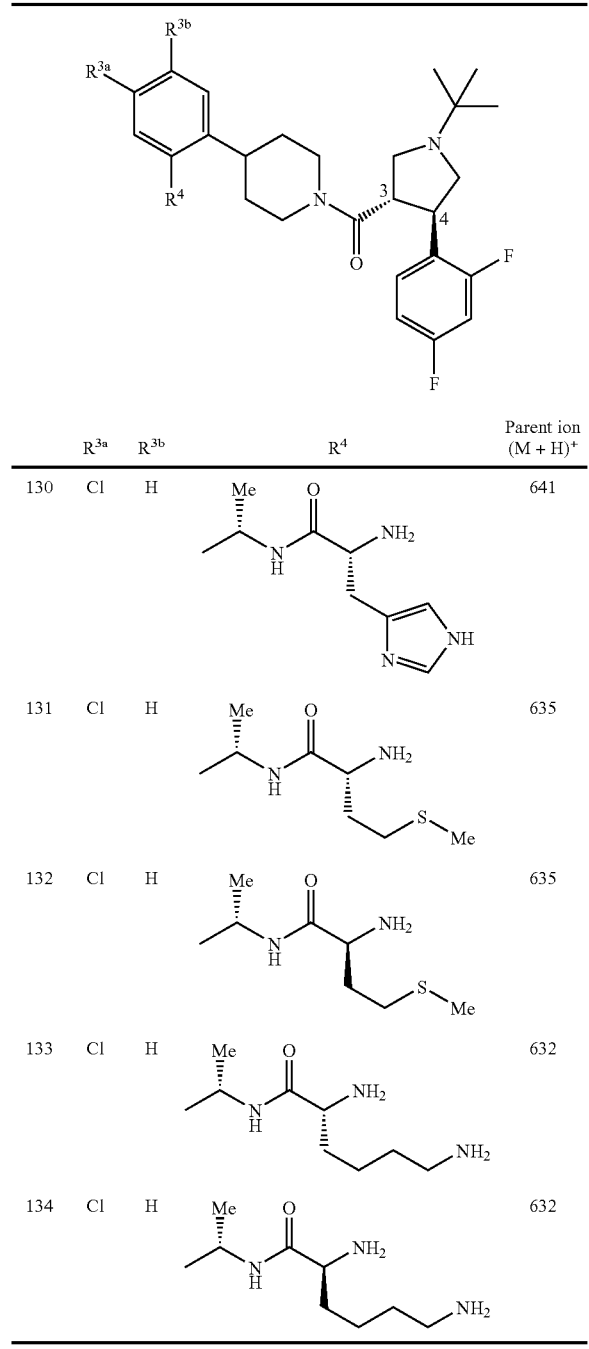

| | $R^{3a}$ | $R^{3b}$ | $R^4$ | Parent ion $(M + H)^+$ |
|---|---|---|---|---|
| 130 | Cl | H | (histidine amide structure) | 641 |
| 131 | Cl | H | (methionine amide structure) | 635 |
| 132 | Cl | H | (methionine amide structure) | 635 |
| 133 | Cl | H | (lysine amide structure) | 632 |
| 134 | Cl | H | (lysine amide structure) | 632 |

Biological Assays

A. Binding Assay

The membrane binding assay was used to identify competitive inhibitors of $^{125}$I-NDP-alpha-MSH binding to cloned human MCRs expressed in mouse L- or Chinese hamster ovary (CHO)-cells.

Cell lines expressing melanocortin receptors were grown in T-180 flasks containing selective medium of the composition: 1 L Dulbecco's modified Eagles Medium (DMEM) with 4.5 g L-glucose, 25 mM Hepes, without sodium pyruvate, (Gibco/BR1); 100 ml 10% heat-inactivated fetal bovine serum (Sigma); 10 mL 10,000 unit/mL penicillin & 10,000 μg/mL streptomycin (Gibco/BR1); 10 ml 200 mM L-glutamine (Gibco/BR1); 1 mg/mL geneticin (G418) (Gibco/BR1). The cells were grown at 37° C. with $CO_2$ and humidity control until the desired cell density and cell number was obtained.

The medium was poured off and 10 mls/monolayer of enzyme-free dissociation media (Specialty Media Inc.) was added. The cells were incubated at 37° C. for 10 min or until cells sloughed off when flask was banged against hand.

The cells were harvested into 200 mL centrifuge tubes and spun at 1000 rpm, 4° C., for 10 min. The supernatant was discarded and the cells were resuspended in 5 mls/monolayer membrane preparation buffer having the composition: 10 mM Tris pH 7.2-7.4; 4 μg/mL Leupeptin (Sigma); 10 μM Phosphoramidon (Boehringer Mannheim); 40 μg/mL Bacitracin (Sigma); 5 μg/mL Aprotinin (Sigma); 10 mM Pefabloc (Boehringer Mannheim). The cells were homogenized with motor-driven dounce (Talboy setting 40), using 10 strokes and the homogenate centrifuged at 6,000 rpm, 4° C., for 15 min.

The pellets were resuspended in 0.2 mls/monolayer membrane prep buffer and aliquots were placed in tubes (500-1000 μL/tube) and quick frozen in liquid nitrogen and then stored at −80° C.

Test compounds or unlabelled NDP-α-MSH was added to 100 μL of membrane binding buffer to a final concentration of 1 μM. The membrane binding buffer had the composition: 50 mM Tris pH 7.2; 2 mM $CaCl_2$; 1 mM $MgCl_2$; 5 mM KCl; 0.2% BSA; 4 μg/mL Leupeptin (SIGMA); 10 μM Phosphoramidon (Boehringer Mannheim); 40 μg/mL Bacitracin (SIGMA); 5 μg/mL Aprotinin (SIGMA); and 10 mM Pefabloc (Boehringer Mannheim). One hundred μL of membrane binding buffer containing 10-40 μg membrane protein was added, followed by 100 μM 125I-NDP-α-MSH to final concentration of 100 pM. The resulting mixture was vortexed briefly and incubated for 90-120 min at room temp while shaking.

The mixture was filtered with Packard Microplate 196 filter apparatus using Packard Unifilter 96-well GF/C filter with 0.1% polyethyleneimine (Sigma). The filter was washed (5 times with a total of 10 mL per well) with room temperature of filter wash having the composition: 50 mM Tris-HCl pH 7.2 and 20 mM NaCl. The filter was dried, and the bottom sealed and 50 μL of Packard Microscint-20 was added to each well. The top was sealed and the radioactivity quantitated in a Packard Topcount Microplate Scintillation counter.

B. Functional Assay

Functional cell based assays were developed to discriminate melanocortin receptor agonists from antagonists.

Cells (for example, CHO- or L-cells or other eukaryotic cells) expressing a human melanocortin receptor (see e.g. Yang-Y K; Ollmann-M M; Wilson-B D; Dickinson-C; Yamada-T; Barsh-GS; Gantz-I; Mol-Endocrinol. 1997 March; 11(3): 274-80) were dissociated from tissue culture flasks by rinsing with Ca and Mg free phosphate buffered saline (14190-136, Life Technologies, Gaithersburg, Md.) and detached following 5 min incubation at 37° C. with enzyme free dissociation buffer (S-014-B, Specialty Media, Lavellette, N.J.). Cells were collected by centrifugation and resuspended in Earle's Balanced Salt Solution (14015-069, Life Technologies, Gaithersburg, Md.) with additions of 10 mM HEPES pH 7.5, 5 mM $MgCl_2$, 1 mM glutamine and 1 mg/ml bovine serum albumin. Cells were counted and diluted to 1 to $5 \times 10^6$/mL. The phosphodiesterase inhibitor 3-isobutyl-1-methylxanthine was added to cells to 0.6 mM.

Test compounds were diluted in dimethylsulfoxide (DMSO) ($10^{-5}$ to $10^{-10}$ M) and 0.1 volume of compound solution was added to 0.9 volumes of cell suspension; the final DMSO concentration was 1%. After room temperature incubation for 45 min, cells were lysed by incubation at 100° C. for 5 min to release accumulated cAMP.

cAMP was measured in an aliquot of the cell lysate with the Amersham (Arlington Heights, Ill.) cAMP detection assay (RPA556). The amount of cAMP production which resulted from an unknown compound was compared to that amount of cAMP produced in response to alpha-MSH which was defined as a 100% agonist. The $EC_{50}$ is defined as the compound concentration which results in half maximal stimulation, when compared to its own maximal level of stimulation.

Antagonist assay: Antagonist activity was defined as the ability of a compound to block cAMP production in response to alpha-MSH. Solution of test compounds and suspension of receptor containing cells were prepared and mixed as described above; the mixture was incubated for 15 min, and an $EC_{50}$ dose (approximately 10 nM alpha-MSH) was added to the cells. The assay was terminated at 45 min and cAMP quantitated as above. Percent inhibition was determined by comparing the amount of cAMP produced in the presence to that produced in the absence of test compound.

C. In vivo Food Intake Models

1) Overnight food intake. Sprague Dawley rats are injected intracerebroventricularly with a test compound in 400 nL of 50% propylene glycol/artificial cerebrospinal fluid one hour prior to onset of dark cycle (12 hours). Food intake is determined using a computerized system in which each rat's food is placed on a computer monitored balance. Cumulative food intake for 16 h post compound administration is measured.

2) Food intake in diet induced obese mice. Male C57/B16J mice maintained on a high fat diet (60% fat calories) for 6.5 months from 4 weeks of age are are dosed intraperitoneally with test compound. Food intake and body weight are measured over an eight day period. Biochemical parameters relating to obesity, including leptin, insulin, triglyceride, free fatty acid, cholesterol and serum glucose levels are determined.

D. Rat Ex Copula Assay

Sexually mature male Caesarian Derived Sprague Dawley (CD) rats (over 60 days old) are used with the suspensory ligament surgically removed to prevent retraction of the penis back into the penile sheath during the ex copula evaluations. Animals receive food and water ad lib and are kept on a normal light/dark cycle. Studies are conducted during the light cycle.

1) Conditioning to Supine Restraint for Ex Copula Reflex Tests. This conditioning takes ~4 days. Day 1, the animals are placed in a darkened restrainer and left for 15-30 minutes. Day 2, the animals are restrained in a supine position in the restrainer for 15-30 minutes. Day 3, the animals are restrained in the supine position with the penile sheath retracted for 15-30 minutes. Day 4, the animals are restrained in the supine position with the penile sheath retracted until penile responses are observed. Some animals require additional days of conditioning before they are completely acclimated to the procedures; non-responders are removed from further evaluation. After any handling or evaluation animals are given a treat to ensure positive reinforcement.

2) Ex Copula Reflex Tests. Rats are gently restrained in a supine position with their anterior torso placed inside a cylinder of adequate size to allow for normal bead and paw grooming. For a 400-500 gram rat, the diameter of the cylinder is approximately 8 cm. The lower torso and hind limbs are restrained with a non-adhesive material (vetrap). An additional piece of vetrap with a hole in it, through which the glans penis will be passed, is fastened over the animal to maintain the preputial sheath in a retracted position. Penile responses will be observed, typically termed ex copula genital reflex tests. Typically, a series of penile erections will occur spontaneously within a few minutes after sheath retraction. The types of normal reflexogenic erectile responses include elongation, engorgement, cup and flip. An elongation is classified as an extension of the penile body. Engorgement is a dilation of the glans penis. A cup is defined as an intense erection where the distal margin of the glans penis momentarily flares open to form a cup. A flip is a dorsiflexion of the penile body.

Baseline and or vehicle evaluations are conducted to determine how and if an animal will respond. Some animals have a long duration until the first response while others are non-responders altogether. During this baseline evaluation latency to first response, number and type of responses are recorded. The testing time frame is 15 minutes after the first response.

After a minimum of 1 day between evaluations, these same animals are administered the test compound at 20 mg/kg and evaluated for penile reflexes. All evaluations are videotaped and scored later. Data are collected and analyzed using paired 2 tailed t-tests to compared baseline and/or vehicle evaluations to drug treated evaluations for individual animals. Groups of a minimum of 4 animals are utilized to reduce variability.

Positive reference controls are included in each study to assure the validity of the study. Animals can be dosed by a number of routes of administration depending on the nature of the study to be performed. The routes of administration includes intravenous (IV), intraperitoneal (IP), subcutaneous (SC) and intracerebral ventricular (ICV).

E. Models of Female Sexual Dysfunction

Rodent assays relevant to female sexual receptivity include the behavioral model of lordosis and direct observations of copulatory activity. There is also a urethrogenital reflex model in anesthetized spinally transected rats for measuring orgasm in both male and female rats. These and other established animal models of female sexual dysfunction are described in McKenna K E et al, *A Model For The Study of Sexual Function In Anesthetized Male And Female Rats*. Am. J. Physiol. (Regulatory Integrative Comp. Physiol 30): R1276-R1285, 1991; McKenna K E et al, *Modulation By Peripheral Serotonin of The Threshold For Sexual Reflexes In Female Rats*. Pharm. Bioch. Behav., 40:151-156, 1991; and Takahashi L K et al, *Dual Estradiol Action In The Diencephalon And The Regulation Of Sociosexual Behavior In Female Golden Hamsters*, Brain Res., 359:194-207, 1985.

Representative compounds of the present invention were tested and found to bind to the melanocortin-4 receptor. These compounds were generally found to have $IC_{50}$ values less than 10 μM. Representative compounds of the present invention were also tested in the functional assay and found generally to activate the melanocortin-4 receptor with $EC_{50}$ values less than 10 μM.

EXAMPLES OF PHARMACEUTICAL COMPOSITIONS

As a specific embodiment of an oral composition of a composition of the present invention, 5 mg of Example 3 is formulated with sufficient finely divided lactose to provide a total amount of 580 to 1000 mg to fill a size O hard gelatin capsule.

As another specific embodiment of an oral composition of a compound of the present invention, 2.5 mg of Example 4 is formulated with sufficient finely divided lactose to provide a total amount of 580 to 1000 mg to fill a size O hard gelatin capsule.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the mammal being treated for severity of bone disorders caused by resorption, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of structural formula I:

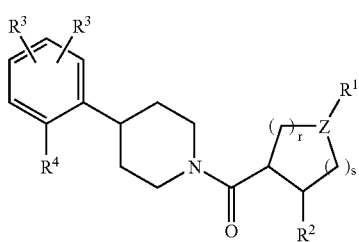

or a pharmaceutically acceptable salt thereof; wherein:
$R^1$ is selected from the group consisting of:
(1) hydrogen,
(2) amidino,
(3) $C_{1-4}$ alkyliminoyl,
(4) $C_{1-10}$ alkyl,
(5) —$(CH_2)_n$—$NR^7R^8$,
(6) —$(CH_2)_n$—$C_{3-7}$ cycloalkyl,
(7) —$(CH_2)_n$-phenyl,
(8) —$(CH_2)_n$-naphthyl, and
(9) —$(CH_2)_n$-heteroaryl,
wherein phenyl, naphthyl, and heteroaryl are unsubstituted or substituted with one to three groups independently selected from $R^3$, and wherein alkyl and cycloalkyl are unsubstituted or substituted with one to three groups independently selected from $R^3$ and oxo;
$R^2$ is selected from the group consisting of:
(1) phenyl,
(2) naphthyl, and
(3) heteroaryl,
wherein phenyl, naphthyl, and heteroaryl are unsubstituted or substituted with one to three groups independently selected from $R^3$;
each $R^3$ is independently selected from the group consisting of:
(1) hydrogen,
(2) $C_{1-6}$ alkyl,
(3) —$(CH_2)_n$-phenyl,
(4) —$(CH_2)_n$-naphthyl,
(5) —$(CH_2)_n$-heteroaryl,
(6) —$(CH_2)_n$-heterocycloalkyl,
(7) —$(CH_2)_n C_{3-7}$ cycloalkyl,
(8) halogen,
(9) $OR^6$,
(10) —$(CH_2)_n N(R^6)_2$,
(11) —$(CH_2)_n C\equiv N$,
(12) —$(CH_2)_n CO_2 R^6$,
(13) $NO_2$,
(14) —$(CH_2)_n NR^6 SO_2 R^6$,
(15) —$(CH_2)_n SO_2 N(R^6)_2$,
(16) —$(CH_2)_n S(O)_p R^6$,
(17) —$(CH_2)_n NR^6 C(O)N(R^6)_2$,
(18) —$(CH_2)_n C(O)N(R^6)_2$,
(19) —$(CH_2)_n NR^6 C(O)R^6$,
(20) —$(CH_2)_n NR^6 CO_2 R^6$,
(21) —$(CH_2)_n NR^6 C(O)$-heteroaryl,
(22) —$(CH_2)_n C(O)NR^6 N(R^6)_2$,
(23) —$(CH_2)_n C(O)NR^6 NR^6 C(O)R^6$,
(24) $O(CH_2)_n C(O)N(R^6)_2$,
(25) $CF_3$,
(26) $CH_2 CF_3$,
(27) $OCF_3$, and
(28) $OCH_2 CF_3$,
wherein phenyl, naphthyl, heteroaryl, cycloalkyl, and heterocycloalkyl are unsubstituted or substituted with one to three substituents independently selected from halogen, hydroxy, oxo, $C_{1-4}$ alkyl, trifluoromethyl, and $C_{1-4}$ alkoxy, and wherein any methylene ($CH_2$) carbon atom in $R^3$ is unsubstituted or substituted with one to two groups independently selected from halogen, hydroxy, and $C_{1-4}$ alkyl, or wherein two substituents when on the same methylene ($CH_2$) group are taken together with the carbon atom to which they are attached to form a cyclopropyl group;
$R^4$ is selected from the group consisting of:
(1) —$(CH_2)_n$—$N(R^5)$—$NR^5R^6$,
(2) —$(CH_2)_n$—$N(R^5)$—$(CH_2)_q$—$NR^5R^6$,
(3) —$(CH_2)_n$—$N(R^5)$—$C(=NR^5)$—$NR^5R^6$,
(4) —$(CH_2)_n$—$N(R^5)$—$(CH_2)_q$—$N(R^5)$—$(C=NR^5)$—$NR^5R^6$,
(5) —$(CH_2)_n$—$N(R^5)$—$(CH_2)_n$—$C(R^5)(N(R^5)_2)$—$(CH_2)_q$—$OR^6$,
(6) —$(CH_2)_n$—$N(R^5)$—$(CH_2)_n$—$C(R^5)(N(R^5)_2)$—$(CH_2)_n$—$R^6$,
(7) —$(CH_2)_n$—$N(R^5)$—$(CH_2)_n$—$C(R^5)(N(R^5)_2)$—$(CH_2)_q$—$S(O)p$—$R^6$,
(8) —$(CH_2)_n$—$N(R^5)$—$(CH_2)_n$—$C(R^5)(N(R^5)_2)$—$(CH_2)_q$—$NR^5R^6$,
(9) —$(CH_2)_n$—$N(R^5)$—$C(O)(CH_2)_n$—$C(R^5)(N(R^5)_2)$—$(CH_2)_n$—$R^6$,
(10) —$(CH_2)_n$—$N(R^5)$—$C(O)(CH_2)_n$—$C(R^5)(N(R^5)_2)$—$(CH_2)_q$—$S(O)p$—$R^6$,
(11) —$(CH_2)_n$—$N(R^5)$—$C(O)(CH_2)_n$—$C(R^5)(N(R^5)_2)$—$(CH_2)_q$—$NR^5R^6$,
(12) —$(CH_2)_n$—$N(R^5)$—$C(O)(CH_2)_n$—$C(R^5)(N(R^5)_2)$—$(CH_2)_q$—$O$—$R^6$, and
wherein $(CH_2)_n$ is unsubstituted or substituted with one to three groups independently selected from halogen, $C_{1-4}$ alkyl, hydroxy, oxo, and $C_{1-4}$ alkoxy;
$R^5$ is selected from the group consisting of:
(1) hydrogen,
(2) $C_{1-6}$ alkyl, and
(3) $C(O)C_{1-6}$ alkyl,
wherein alkyl is unsubstituted or substituted with one to three groups independently selected from halogen, $C_{1-4}$ alkyl, hydroxy, oxo, and $C_{1-4}$ alkoxy;

$R^6$ is selected from the group consisting of:
  (1) hydrogen,
  (2) $C_{1-6}$ alkyl,
  (3) $C(O)C_{1-6}$ alkyl,
  (4) —$(CH_2)_nC_{3-7}$ cycloalkyl,
  (5) —$(CH_2)_nC_{2-7}$ heterocycloalkyl,
  (6) —$(CH_2)_n$-phenyl,
  (7) —$(CH_2)_n$-naphthyl,
  (8) —$(CH_2)_n$-heteroaryl, and
  (9) —$(CH_2)_nC_{3-7}$ bicycloalkyl,
  wherein alkyl, phenyl, heteroaryl, heterocycloalkyl, naphthyl, cycloalkyl, bicycloalkyl and $(CH_2)_n$ are unsubstituted or substituted with one to three groups independently selected from halogen, $C_{1-4}$ alkyl, hydroxy, and $C_{1-4}$ alkoxy, or wherein two $R^6$ groups together with the atom to which they are attached form a 4- to 8-membered mono- or bicyclic ring system optionally containing an additional heteroatom selected from O, S, and —$NC_{1-4}$ alkyl;
each $R^7$ and $R^8$ is independently selected from the group consisting of:
  (1) hydrogen,
  (2) amidino,
  (3) $C_{1-4}$ alkyliminoyl,
  (4) $C_{1-10}$ alkyl,
  (5) —$(CH_2)_n$—$C_{3-7}$ cycloalkyl,
  (6) —$(CH_2)_n$-phenyl,
  (7) —$(CH_2)_n$-naphthyl, and
  (8) —$(CH_2)_n$-heteroaryl,
  wherein phenyl, naphthyl, and heteroaryl are unsubstituted or substituted with one to three groups independently selected from $R^3$, and wherein alkyl and cycloalkyl are unsubstituted or substituted with one to three groups independently selected from $R^3$ and oxo;
$R^9$ is selected from the group consisting of:
Z represents N;
r is 1 or 2;
s is 0, 1, or 2;
n is 0, 1, 2, or 3;
p is 0, 1, or 2; and
q is 1, 2, 3, or 4.

2. The compound of claim 1 wherein $R^1$ is selected from the group consisting of: hydrogen, $C_{1-6}$ alkyl, —$(CH_2)_{0-1}C_{3-6}$ cycloalkyl, and —$(CH_2)_{0-1}$-phenyl, wherein phenyl is unsubstituted or substituted with one to three groups independently selected from $R^3$, and alkyl and cycloalkyl are optionally substituted with one to three groups independently selected from $R^3$ and oxo; and pharmaceutically acceptable salts thereof.

3. The compound of claim 2 wherein $R^2$ is phenyl or thienyl, optionally substituted with one to three groups independently selected from $R^3$; and pharmaceutically acceptable salts thereof.

4. The compound of claim 3 wherein $R^2$ is phenyl optionally substituted with one to three groups independently selected from $R^3$; and pharmaceutically acceptable salts thereof.

5. The compound of claim 1 wherein each $R^3$ is independently selected from the group consisting of: $C_{1-6}$ alkyl, —$(CH_2)_n$-phenyl, -$(CH_2)_n$-heteroaryl, —$(CH_2)_nC_{2-7}$ heterocycloalkyl, —$(CH_2)_nC_{3-7}$ cycloalkyl, halogen, $OR^5$, —$(CH_2)_n N(R^5)_2$, —$(CH_2)_nCO_2R^5$, $NO_2$, and $CF_3$, wherein phenyl, naphthyl, and heteroaryl are unsubstituted or substituted with one to three substituents independently selected from halogen, hydroxy, $C_{1-4}$ alkyl, trifluoromethyl, and $C_{1-4}$ alkoxy, and wherein alkyl, cycloalkyl, heterocycloalkyl, and $(CH_2)_n$ are unsubstituted or substituted with one to three substituents independently selected from halogen, hydroxy, oxo, $C_{1-4}$ alkyl, trifluoromethyl, and $C_{1-4}$ alkoxy, or wherein two substituents when on the same methylene ($CH_2$) group are taken together with the carbon atom to which they are attached to form a cyclopropyl group; and pharmaceutically acceptable salts thereof.

6. The compound of claim 1 wherein $R^4$ is selected from the group consisting of:
  (1) —$(CH_2)_n$—$N(R^5)$—$NH_2$,
  (2) —$(CH_2)_n$—$N(R^5)$—$(CH_2)_q$—$NH_2$,
  (3) —$(CH_2)_n$—$N(R^5)$—$(CH_2)_n$—$NR^5R^6$,
  (4) —$(CH_2)_n$—$N(R^5)$—$(CH_2)_n$—$NHC_{1-6}$ alkyl,
  (5) —$(CH_2)_n$—$N(R^5)$—$(CH_2)_n$—$N(C_{1-6}$ alkyl$)_2$,
  (6) —$(CH_2)_n$—$N(R^5)$—$(CH_2)_n$—$NHC(O)C_{1-6}$ alkyl,
  (7) —$(CH_2)_n$—$N(R^5)$—$(CH_2)_n$—$N(R^5)C(O)C_{1-6}$ alkyl,
  (8) —$(CH_2)_n$—$N(R^5)$—$(CH_2)_n$—$N(C(O)C_{1-6}$ alkyl$)_2$,
  (9) —$(CH_2)_n$—$N(R^5)$—$C(=NH)$—$NH_2$,
  (10) —$(CH_2)_n$—$N(R^5)$—$(CH_2)_q$—$NH(C=NH)$—$NH_2$,
  (11) —$(CH_2)_n$—$N(R^5)$—$(CH_2)_n$—$C(R^5)(NH_2)(CH_2)_q$—OH,
  (12) —$(CH_2)_n$—$N(R^5)$—$(CH_2)_n$—$C(R^5)(NH_2)(CH_2)_q$—$OC_{1-6}$ alkyl,
  (13) —$(CH_2)_n$—$N(R^5)$—$(CH_2)_n$—$C(R^5)(NH_2)(CH_2)_q$—$OR^6$,
  (14) —$(CH_2)_n$—$N(R^5)$—$(CH_2)_n$—$C(R^5)(NH_2)(CH_2)_n$-heteroaryl,
  (15) —$(CH_2)_n$—$N(R^5)$—$(CH_2)_n$—$C(R^5)(NH_2)(CH_2)_n$—$R^6$,
  (16) —$(CH_2)_n$—$N(R^5)$—$(CH_2)_n$—$C(R^5)(NH_2)(CH_2)_q$—SH,
  (17) —$(CH_2)_n$—$N(R^5)$—$(CH_2)_n$—$C(R^5)(NH_2)(CH_2)_q$—S—$C_{1-6}$ alkyl,
  (18) —$(CH_2)_n$—$N(R^5)$—$(CH_2)_n$—$C(R^5)(NH_2)(CH_2)_q$—S—$R^6$,
  (19) —$(CH_2)_n$—$N(R^5)$—$(CH_2)_n$—$C(R^5)(NH_2)(CH_2)_q$—$NH_2$,
  (20) —$(CH_2)_n$—$N(R^5)$—$(CH_2)_n$—$C(R^5)(NH_2)(CH_2)_q$—$NHR^6$,
  (21) —$(CH_2)_n$—$N(R^5)$—$(CH_2)_n$—$C(R^5)(NH_2)(CH_2)_q$—$NR^5R^6$,
  (22) —$(CH_2)_n$—$N(R^5)$—$C(O)(CH_2)_n$—$C(R^5)(NH_2)(CH_2)_n$-heteroaryl,
  (23) —$(CH_2)_n$—$N(R^5)$—$C(O)(CH_2)_n$—$C(R^5)(NH_2)(CH_2)_q$—SH,
  (24) —$(CH_2)_n$—$N(R^5)$—$C(O)(CH_2)_n$—$C(R^5)(NH_2)(CH_2)_q$—S—$C_{1-6}$ alkyl,
  (25) —$(CH_2)_n$—$N(R^5)$—$C(O)(CH_2)_n$—$C(R^5)(NH_2)(CH_2)_q$—$NR^5R^6$, and
wherein alkyl and $(CH_2)_n$ are unsubstituted or substituted with one to three groups independently selected from halogen, $C_{1-4}$ alkyl, hydroxy, oxo, and $C_{1-4}$ alkoxy, and heteroaryl is unsubstituted or substituted with one to three groups independently selected from halogen, $C_{1-4}$ alkyl, hydroxy, and $C_{1-4}$ alkoxy; and pharmaceutically acceptable salts thereof.

7. The compound of claim 1 wherein $R^6$ is selected from the group consisting of: hydrogen, $C_{1-6}$ alkyl, $C(O)C_{1-6}$ alkyl, and —$(CH_2)_n$-heteroaryl; and pharmaceutically acceptable salts thereof.

8. The compound of claim 1 wherein r is 1 and s is 1; and pharmaceutically acceptable salts thereof.

9. The compound of claim 1 wherein r is 2 and s is 1; and pharmaceutically acceptable salts thereof.

10. The compound of claim 1 of structural formula IIa or IIb of the indicated trans relative stereochemical configuration:

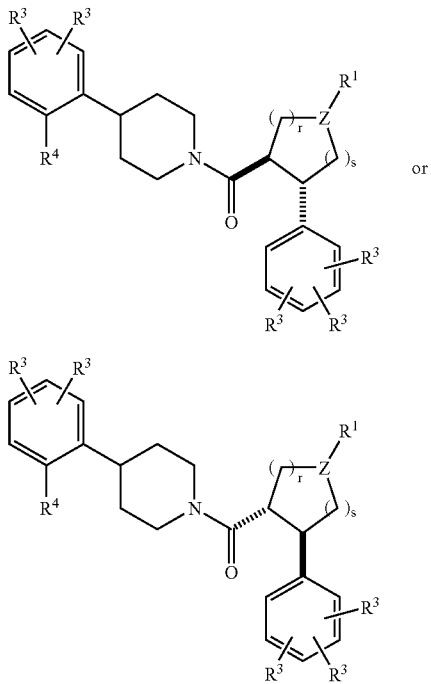

or a pharmaceutically acceptable salt thereof; wherein:
$R^1$ is selected from the group consisting of: hydrogen, amidino, $C_{1-4}$ alkyliminoyl, $C_{1-6}$ alkyl, $C_{5-6}$ cycloalkyl, —$(CH_2)_{0-1}$ phenyl, and —$(CH_2)_{0-1}$ heteroaryl, wherein phenyl and heteroaryl are unsubstituted or substituted with one to three groups independently selected from $R^3$, and wherein alkyl and cycloalkyl are unsubstituted or substituted with one to three groups independently selected from $R^3$ and oxo;

each $R^3$ is independently selected from the group consisting of:
(1) hydrogen,
(2) $C_{1-6}$ alkyl,
(3) —$(CH_2)_n$-phenyl,
(4) —$(CH_2)_n$-naphthyl,
(5) —$(CH_2)_n$-heteroaryl,
(6) —$(CH_2)_n$-heterocycloalkyl,
(7) —$(CH_2)_n C_{3-7}$ cycloalkyl,
(8) halogen,
(9) $OR^{64}$,
(10) —$(CH_2)_n N(R^{64})_2$,
(11) —$(CH_2)_n C\equiv N$,
(12) —$(CH_2)_n CO_2 R^{64}$,
(13) $NO_2$,
(14) —$(CH_2)_n NR^4 SO_2 R^{64}$,
(15) —$(CH_2)_n SO_2 N(R^{64})_2$,
(16) —$(CH_2)_n S(O)_{0-1} R^{64}$,
(17) —$(CH_2)_n NR^{64} C(O)N(R^{64})_2$,
(18) —$(CH_2)_n C(O)N(R^{64})_2$,
(19) —$(CH_2)_n NR^{64} C(O)R^{64}$,
(20) —$(CH_2)_n NR^{64} CO_2 R^{64}$,
(21) —$(CH_2)_n NR^{64} C(O)$-heteroaryl,
(22) —$(CH_2)_n C(O)NR^{64} N(R^{64})_2$,
(23) —$(CH_2)_n C(O)NR^{64} NR^{64} C(O)R^{64}$,
(24) $O(CH_2)_n C(O)N(R^{64})_2$,
(25) $CF_3$,
(26) $CH_2 CF_3$,
(27) $OCF_3$, and
(28) $OCH_2 CF_3$, wherein phenyl, naphthyl, heteroaryl, cycloalkyl, and heterocycloalkyl are unsubstituted or substituted with one to three substituents independently selected from halogen, hydroxy, oxo, $C_{1-4}$ alkyl, trifluoromethyl, and $C_{1-4}$ alkoxy, and wherein any methylene ($CH_2$) carbon atom in $R^3$ is unsubstituted or substituted with one to two groups independently selected from halogen, hydroxy, and $C_{1-4}$ alkyl, or wherein two substituents when on the same methylene ($CH_2$) group are taken together with the carbon atom to which they are attached to form a cyclopropyl group;

$R^4$ is selected from the group consisting of:
(1) —$(CH_2)$—$N(R^5)$—$NR^5 R^6$,
(2) —$(CH_2)$—$N(R^5)$—$(CH_2)_{1-3}$—$NR^5 R^6$,
(3) —$(CH_2)$—$N(R^5)$—$C(=NR^5)$—$NR^5 R^6$,
(4) —$(CH_2)$—$N(R^5)$—$(CH_2)_{1-3}$—$N(R^5)$—$(C=NR^5)$—$NR^5 R^6$,
(5) —$(CH_2)$—$N(R^5)$—$(CH_2)_{0-2}$—$C(R^5)(N(R^5)_2)$—$(CH_2)_{1-2}$—$OR^6$,
(6) —$(CH_2)$—$N(R^5)$—$(CH_2)_{0-2}$—$C(R^5)(N(R^5)_2)$—$(CH_2)_{1-2}$—$R^6$,
(7) —$(CH_2)$—$N(R^5)$—$(CH_2)_{0-2}$—$C(R^5)(N(R^5)_2)$—$(CH_2)_{1-2}$—$S$—$R^6$,
(8) —$(CH_2)$—$N(R^5)$—$(CH_2)_{0-2}$—$C(R^5)(N(R^5)_2)$—$(CH_2)_{1-4}$—$NR^5 R^6$,
(9) —$(CH_2)$—$N(R^5)$—$C(O)(CH_2)_{0-2}$—$C(R^5)(N(R^5)_2)$—$(CH_2)_{1-2}$—$R^6$,
(10) —$(CH_2)$—$N(R^5)$—$C(O)(CH_2)_{0-2}$—$C(R^5)(N(R^5)_2)(CH_2)_{1-2}$—$S$—$R^6$,
(11) —$(CH_2)$—$N(R^5)$—$C(O)(CH_2)_{0-2}$—$C(R^5)(N(R^5)_2)(CH_2)_{1-4}$—$NR^5 R^6$, and wherein $(CH_2)_n$ is unsubstituted or substituted with one to three groups independently selected from halogen, $C_{1-4}$ alkyl, hydroxy, oxo, and $C_{1-4}$ alkoxy;

$R^5$ is selected from the group consisting of:
(1) hydrogen,
(2) $C_{1-6}$ alkyl, and
(3) $C(O)C_{1-6}$ alkyl, wherein alkyl is unsubstituted or substituted with one to three groups independently selected from halogen, $C_{1-4}$ alkyl, hydroxy, oxo, and $C_{1-4}$ alkoxy;

$R^6$ is selected from the group consisting of:
(1) hydrogen,
(2) $C_{1-6}$ alkyl,
(3) $C(O)C_{1-6}$ alkyl,
(4) —$(CH_2)_n C_{3-7}$ cycloalkyl,
(5) —$(CH_2)_n C_{2-7}$ heterocycloalkyl,
(6) —$(CH_2)_n$-phenyl,
(7) —$(CH_2)_n$-naphthyl,
(8) —$(CH_2)_n$-heteroaryl, and
(9) —$(CH_2)_n C_{3-7}$ bicycloalkyl, wherein alkyl, phenyl, heteroaryl, heterocycloalkyl, naphthyl, cycloalkyl, bicycloalkyl and $(CH_2)_n$ are unsubstituted or substituted with one to three groups independently selected from halogen, $C_{1-4}$ alkyl, hydroxy, and $C_{1-4}$ alkoxy, or wherein two $R^6$ groups together with the atom to which they are attached form a 4- to 8-membered mono- or bicyclic ring system optionally containing an additional heteroatom selected from O, S, and —$NC_{1-4}$ alkyl;

each $R^7$ and $R^8$ is independently selected from the group consisting of:
(1) hydrogen,
(2) amidino,
(3) $C_{1-4}$ alkyliminoyl, (4) $C_{1-10}$ alkyl,
(5) —$(CH_2)_n$—$C_{3-7}$ cycloalkyl,
(6) —$(CH_2)_n$-phenyl,
(7) —$(CH_2)_n$-naphthyl, and
(8) —$(CH_2)_n$-heteroaryl,
wherein phenyl, naphthyl, and heteroaryl are unsubstituted or substituted with one to three groups independently selected from $R^3$, and wherein alkyl and cycloalkyl are unsubstituted or substituted with one to three groups independently selected from $R^3$ and oxo;
$R^9$ is selected from the group consisting of:
Z represents N;
r is 1 or 2;
s is 0, 1, or 2; and
n is 0, 1, 2, 3 or 4.

11. The compound of claim 1 of structural formula IIIa or IIIb of the indicated trans relative stereochemical configuration:

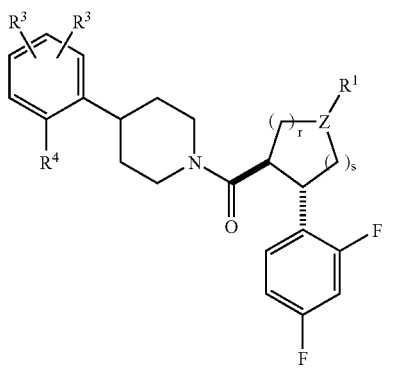

(IIIa)

or

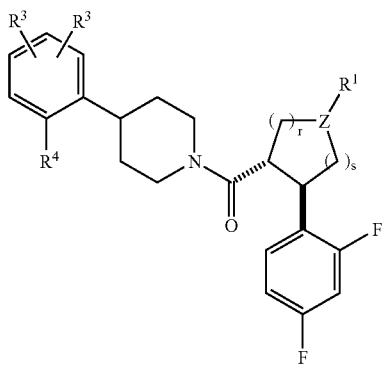

(IIIb)

or a pharmaceutically acceptable salt thereof, wherein:
$R^1$ is selected from the group consisting of: hydrogen, $C_{1-4}$ alkyl, and —$(CH_2)_{0-1}$ phenyl;
each $R^3$ is independently selected from the group consisting of:
(1) hydrogen,
(2) $C_{1-6}$ alkyl,
(3) —$(CH_2)_n$-phenyl,
(4) —$(CH_2)_n$-naphthyl,
(5) —$(CH_2)_n$-heteroaryl,
(6) —$(CH_2)_n$-heterocycloalkyl,
(7) —$(CH_2)_n C_{3-7}$ cycloalkyl,
(8) halogen,
(9) $OR^{64}$,
(10) —$(CH_2)_n N(R^{64})_2$,
(11) —$(CH_2)_n C\equiv N$,
(12) —$(CH_2)_n CO_2 R^{64}$,
(13) $NO_2$,
(14) —$(CH_2)_n NR^{64}SO_2 R^{64}$,
(15) —$(CH_2)_n SO_2 N(R^{64})_2$,
(16) —$(CH_2)_n S(O)_{0-1} R^{64}$,
(17) —$(CH_2)_n NR^{64}C(O)N(R^{64})_2$,
(18) —$(CH_2)_n C(O)N(R^{64})_2$,
(19) —$(CH_2)_n NR^{64}C(O)R^{64}$,
(20) —$(CH_2)_n NR^{64}CO_2 R^{64}$,
(21) —$(CH_2)_n NR^{64}C(O)$-heteroaryl,
(22) —$(CH_2)_n C(O)NR^{64}N(R^{64})_2$,
(23) —$(CH_2)_n C(O)NR^{64}NR^{64}C(O)R^{64}$,
(24) $O(CH_2)_n C(O)N(R^{64})_2$,
(25) $CF_3$,
(26) $CH_2CF_3$,
(27) $OCF_3$, and
(28) $OCH_2CF_3$,
wherein phenyl, naphthyl, heteroaryl, cycloalkyl, and heterocycloalkyl are unsubstituted or substituted with one to three substituents independently selected from halogen, hydroxy, oxo, $C_{1-4}$ alkyl, trifluoromethyl, and $C_{1-4}$ alkoxy, and wherein any methylene ($CH_2$) carbon atom in $R^3$ is unsubstituted or substituted with one to two groups independently selected from halogen, hydroxy, and $C_{1-4}$ alkyl, or wherein two substituents when on the same methylene ($CH_2$) group are taken together with the carbon atom to which they are attached to form a cyclopropyl group;
$R^4$ is selected from the group consisting of:
(1) —$(CH_2)$—$N(R^5)$—$NR^5R^6$,
(2) —$(CH_2)$—$N(R^5)$—$(CH_2)_{1-3}$—$NR^5R^6$,
(3) —$(CH_2)$—$N(R^5)$—$C(=NR^5)$—$NR^5R^6$,
(4) —$(CH_2)$—$N(R^5)$—$(CH_2)_{1-3}$—$N(R^5)$—$(C=NR^5)$—$NR^5R^6$,
(5) —$(CH_2)$—$N(R^5)$—$(CH_2)_{0-2}$—$C(R^5)(N(R^5)_2)$—$(CH_2)_{1-2}$—$OR^6$,
(6) —$(CH_2)$—$N(R^5)$—$(CH_2)_{0-2}$—$C(R^5)(N(R^5)_2)(CH_2)_{1-2}$—$R^6$,
(7) —$(CH_2)$—$N(R^5)$—$(CH_2)_{0-2}$—$C(R^5)(N(R^5)_2)(CH_2)_{1-2}$—$S$—$R^6$,
(8) —$(CH_2)$—$N(R^5)$—$(CH_2)_{0-2}$—$C(R^5)(N(R^5)_2)(CH_2)_{1-4}$—$NR^5R^6$,
(9) —$(CH_2)$—$N(R^5)$—$C(O)(CH_2)_{0-2}$—$C(R^5)(N(R^5)_2)(CH_2)_{1-2}$—$R^6$,
(10) —$(CH_2)$—$N(R^5)$—$C(O)(CH_2)_{0-2}$—$C(R^5)(N(R^5)_2)(CH_2)_{1-2}$—$S$—$R^6$,
(11) —$(CH_2)$—$N(R^5)$—$C(O)(CH_2)_{0-2}$—$C(R^5)(N(R^5)_2)(CH_2)_{1-4}$—$NR^5R^6$, and
wherein $(CH_2)_n$ is unsubstituted or substituted with one to three groups independently selected from halogen, $C_{1-4}$ alkyl, hydroxy, oxo, and $C_{1-4}$ alkoxy;
$R^5$ is selected from the group consisting of:
(1) hydrogen,
(2) $C_{1-6}$ alkyl, and
(3) $C(O)C_{1-6}$ alkyl,
wherein alkyl is unsubstituted or substituted with one to three groups independently selected from halogen, $C_{1-4}$ alkyl, hydroxy, oxo, and $C_{1-4}$ alkoxy;
$R^6$ is selected from the group consisting of:
(1) hydrogen,
(2) $C_{1-6}$ alkyl,
(3) $C(O)C_{1-6}$alkyl,
(4) —$(CH_2)_n C_{3-7}$ cycloalkyl,
(5) —$(CH_2)_n C_{2-7}$ heterocycloalkyl,
(6) —$(CH_2)_n$-phenyl,
(7) —$(CH_2)_n$-naphthyl,
(8) —$(CH_2)_n$-heteroaryl, and
(9) —$(CH_2)_n C_{3-7}$ bicycloalkyl, wherein alkyl, phenyl, heteroaryl, heterocycloalkyl, naphthyl, cycloalkyl, bicycloalkyl and (CH$_2$)$_n$ are unsubstituted or substituted with one to three groups independently selected from halogen, C$_{1-4}$ alkyl, hydroxy, and C$_{1-4}$ alkoxy, or wherein two R$^6$ groups together with the atom to which they are attached form a 4- to 8-membered mono- or bicyclic ring system optionally containing an additional heteroatom selected from O, S, and —NC$_{1-4}$ alkyl;

each R$^7$ and R$^8$ is independently selected from the group consisting of:
(1) hydrogen,
(2) amidino,
(3) C$_{1-4}$ alkyliminoyl,
(4) C$_{1-10}$ alkyl,
(5) —(CH$_2$)$_n$—C$_{3-7}$ cycloalkyl,
(6) —(CH$_2$)$_n$-phenyl,
(7) —(CH$_2$)$_n$-naphthyl, and
(8) —(CH$_2$)$_n$-heteroaryl,
wherein phenyl, naphthyl, and heteroaryl are unsubstituted or substituted with one to three groups independently selected from R$^3$, and wherein alkyl and cycloalkyl are unsubstituted or substituted with one to three groups independently selected from R$^3$ and oxo;

R$^9$ is selected from the group consisting of:
Z represents N;
r is 1 or 2;
s is 0, 1, or 2; and
n is 0, 1, 2, 3, or 4.

12. The compound of claim 11 selected from the group consisting of:

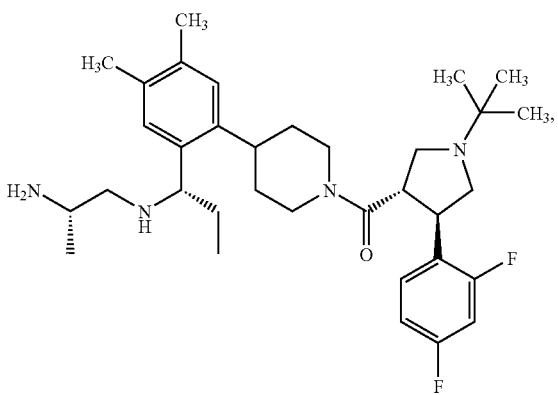

-continued

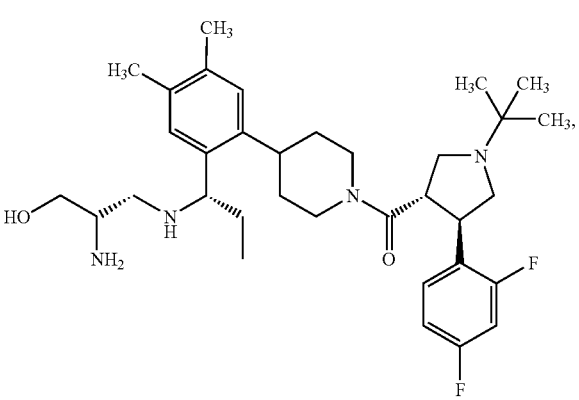

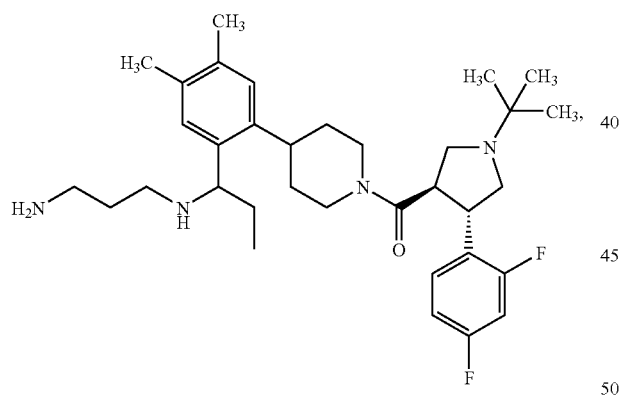

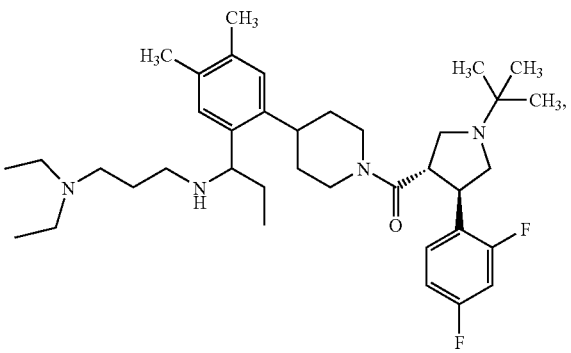

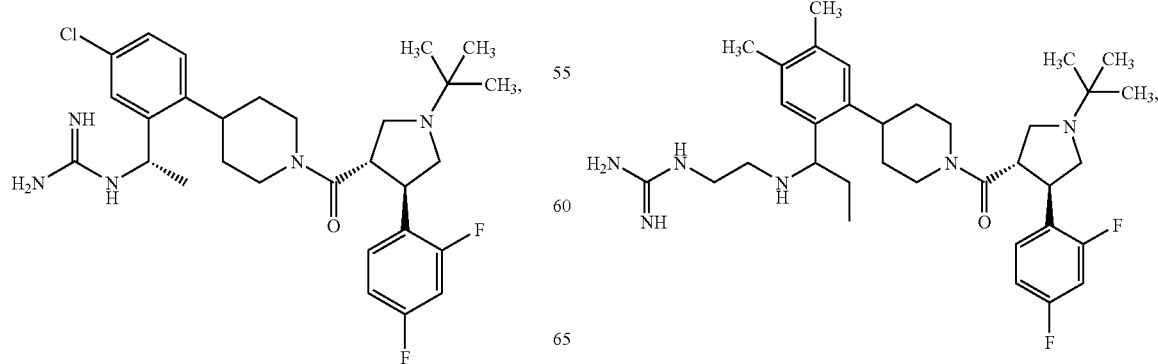

-continued

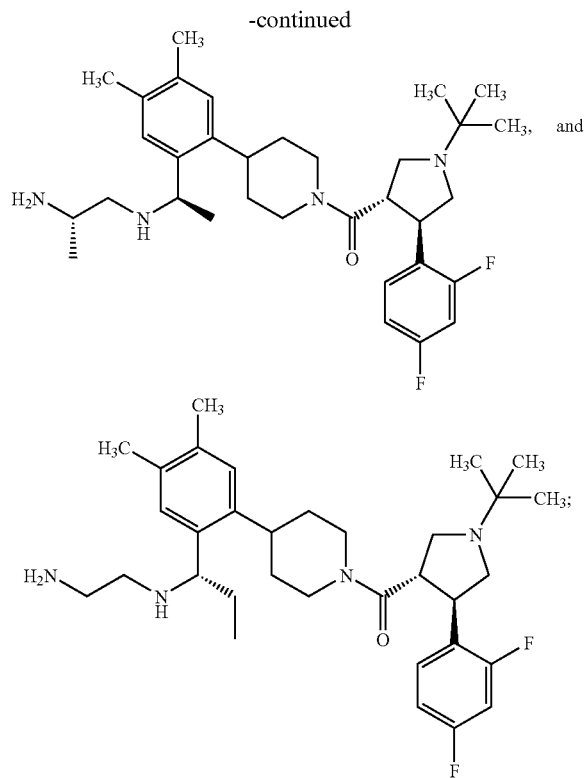

or a pharmaceutically acceptable salt thereof.

13. The compound of claim 12 which is:

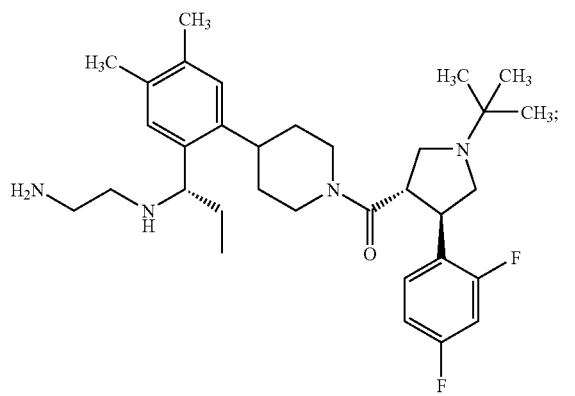

or a pharmaceutically acceptable salt thereof.

14. The compound of claim 12 which is:

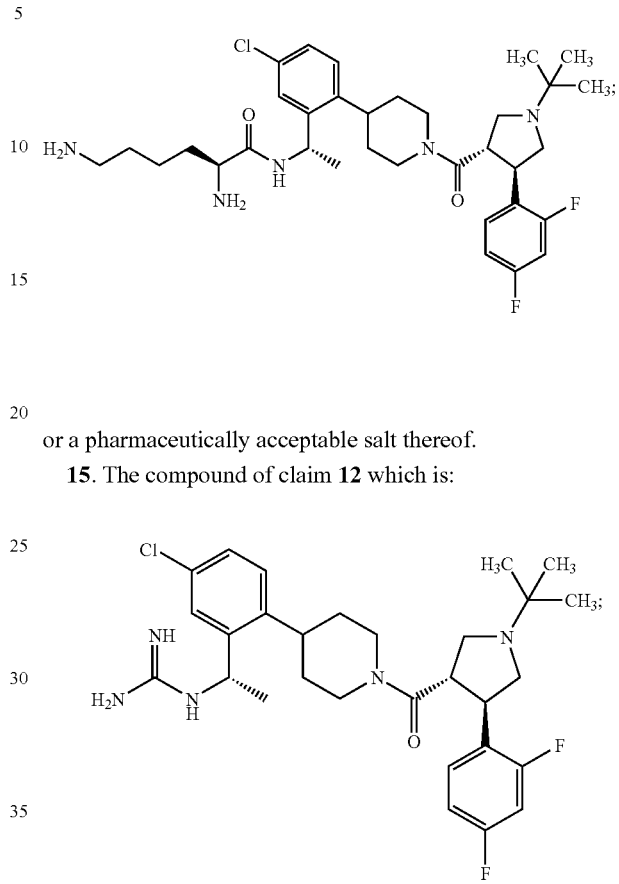

or a pharmaceutically acceptable salt thereof.

15. The compound of claim 12 which is:

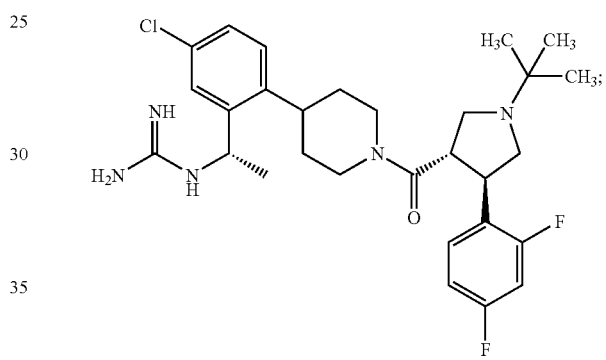

or a pharmaceutically acceptable salt thereof.

16. A pharmaceutical composition which comprises an effective amount of a compound of claim 1 and a pharmaceutically acceptable carrier.

17. A method for the treatment of obesity or diabetes mellitus in a mammal in need thereof which comprises administering to the mammal a therapeutically effective amount of a compound according to claim 1.

* * * * *